(12) United States Patent
Cook et al.

(10) Patent No.: US 10,238,862 B2
(45) Date of Patent: *Mar. 26, 2019

(54) EXTRACRANIAL IMPLANTABLE DEVICES, SYSTEMS AND METHODS FOR THE TREATMENT OF MEDICAL DISORDERS

(71) Applicant: THE REGENTS OF THE UNIVERSITY OF CALIFORNIA, Oakland, CA (US)

(72) Inventors: Ian A. Cook, Los Angeles, CA (US); Christopher M. DeGiorgio, Valencia, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/949,987

(22) Filed: Apr. 10, 2018

(65) Prior Publication Data
US 2018/0229029 A1    Aug. 16, 2018

Related U.S. Application Data

(63) Continuation of application No. 15/624,640, filed on Jun. 15, 2017, now abandoned, which is a
(Continued)

(51) Int. Cl.
*A61N 1/00* (2006.01)
*A61N 1/05* (2006.01)
*A61N 1/36* (2006.01)

(52) U.S. Cl.
CPC ......... *A61N 1/0551* (2013.01); *A61N 1/3606* (2013.01); *A61N 1/36146* (2013.01);
(Continued)

(58) Field of Classification Search
CPC .. A61N 1/0456; A61N 1/0476; A61N 1/0492; A61N 1/0504; A61N 1/0526;
(Continued)

(56) References Cited

U.S. PATENT DOCUMENTS 3,279,468 A    10/1966  Le Vine
3,709,228 A    1/1973   Barker
(Continued)

FOREIGN PATENT DOCUMENTS

AU    2010303586    12/2015
JP    7289649       11/1995
(Continued)

OTHER PUBLICATIONS

Degiorgio, C. et al., Pilot Study of Trigeminal Nerve Stimulation (TNS) for Epilepsy: A Proof-of-Concept Trial, Epilepsia, 47(7): 1213-1215 (2006).
(Continued)

*Primary Examiner* — William J Levicky
(74) *Attorney, Agent, or Firm* — Vista IP Law Group LLP

(57) ABSTRACT

The present disclosure relates to methods, devices and systems used for the treatment of medical disorders via stimulation of the superficial elements of the trigeminal nerve. More specifically, minimally invasive systems, devices and methods of stimulation of the superficial branches of the trigeminal nerve located extracranially in the face, namely the supraorbital, supratrochlear, infraorbital, auriculotemporal, zygomaticotemporal, zygomaticoorbital, zygomaticofacial, nasal and mentalis nerves (also referred to collectively as the superficial trigeminal nerve) are disclosed herein.

8 Claims, 19 Drawing Sheets

Related U.S. Application Data continuation of application No. 13/994,512, filed as application No. PCT/US2011/065003 on Dec. 14, 2011, now abandoned, and a continuation-in-part of application No. 12/898,696, filed on Oct. 5, 2010, now abandoned, and a continuation-in-part of application No. 12/898,685, filed on Oct. 5, 2010, now Pat. No. 8,958,880.

(60) Provisional application No. 61/354,641, filed on Jun. 14, 2010, provisional application No. 61/305,514, filed on Feb. 17, 2010, provisional application No. 61/289,829, filed on Dec. 23, 2009, provisional application No. 61/248,827, filed on Oct. 5, 2009, provisional application No. 61/479,779, filed on Apr. 27, 2011, provisional application No. 61/445,454, filed on Feb. 22, 2011, provisional application No. 61/440,802, filed on Feb. 8, 2011, provisional application No. 61/423,008, filed on Dec. 14, 2010.

(52) U.S. Cl.
CPC .......... *A61N 1/0504* (2013.01); *A61N 1/0526* (2013.01); *A61N 1/361* (2013.01); *A61N 1/3611* (2013.01); *A61N 1/3616* (2013.01); *A61N 1/36053* (2013.01); *A61N 1/36064* (2013.01); *A61N 1/36085* (2013.01); *A61N 1/36089* (2013.01); *A61N 1/36096* (2013.01); *A61N 1/36114* (2013.01); *A61N 1/36171* (2013.01); *A61N 1/36178* (2013.01)

(58) Field of Classification Search
CPC .... A61N 1/0529; A61N 1/36; A61N 1/36025; A61N 1/36146; A61N 1/36114
See application file for complete search history.

(56) References Cited

U.S. PATENT DOCUMENTS

| | | | |
|---|---|---|---|
| 4,233,986 | A | 11/1980 | Tannenbaum |
| 4,305,402 | A | 12/1981 | Katims |
| 4,635,641 | A | 1/1987 | Hoffman |
| 5,514,175 | A | 5/1996 | Kim et al. |
| 5,540,734 | A | 7/1996 | Zabara |
| 5,549,734 | A | 8/1996 | DeGiorgio et al. |
| 5,814,095 | A | 9/1998 | Muller et al. |
| 6,061,593 | A | 5/2000 | Fischell et al. |
| 6,405,079 | B1 | 6/2002 | Ansarinia |
| 6,549,808 | B1 | 4/2003 | Gisel et al. |
| 6,567,702 | B1 | 5/2003 | Nekhendzy et al. |
| 6,735,475 | B1 | 5/2004 | Whitehurst et al. |
| 6,950,707 | B2 | 9/2005 | Whitehurst |
| 6,954,668 | B1 | 10/2005 | Cuozzo |
| 7,003,352 | B1 | 2/2006 | Whitehurst |
| 7,171,276 | B2 | 1/2007 | Giuntoli et al. |
| 7,502,652 | B2 | 3/2009 | Gaunt et al. |
| 7,734,340 | B2 | 6/2010 | De Ridder |
| 7,769,461 | B2 | 8/2010 | Whitehurst et al. |
| 7,801,601 | B2 | 9/2010 | Maschino et al. |
| 8,315,704 | B2 | 11/2012 | Jaax et al. |
| 8,380,315 | B2 | 2/2013 | DeGiorgio et al. |
| 8,428,734 | B2 | 4/2013 | Rigaux et al. |
| 8,494,641 | B2 | 7/2013 | Boling et al. |
| 8,512,715 | B2 | 8/2013 | Papay |
| 8,554,324 | B2 | 10/2013 | Brooke |
| 8,565,896 | B2 | 10/2013 | Ben-David et al. |
| 8,591,419 | B2 | 11/2013 | Tyler |
| 8,666,498 | B2 | 3/2014 | Newman |
| 8,688,220 | B2 | 4/2014 | DeGiorgio et al. |
| 8,700,164 | B2 | 4/2014 | DeGiorgio et al. |
| 8,849,407 | B1 | 9/2014 | Danilov |
| 8,958,880 | B2 | 2/2015 | DeGiorgio et al. |
| 9,186,510 | B2 | 11/2015 | Gliner et al. |
| 9,238,139 | B2 | 1/2016 | DeGiorgio et al. |
| 9,364,674 | B2 | 6/2016 | Cook et al. |
| 9,504,827 | B2 | 11/2016 | DeGiorgio et al. |
| 9,511,223 | B2 | 12/2016 | DeGiorgio et al. |
| 9,682,236 | B2 | 6/2017 | DeGiorgio |
| 10,016,601 | B2 | 7/2018 | Cook et al. |
| 10,058,704 | B2 | 8/2018 | GeGiorgio et al. |
| 2002/0077670 | A1 | 6/2002 | Archer et al. |
| 2003/0045922 | A1 | 3/2003 | Northrop |
| 2003/0195588 | A1 | 10/2003 | Fischell et al. |
| 2004/0127965 | A1 | 7/2004 | Borkan |
| 2004/0138097 | A1 | 7/2004 | Guyuron |
| 2004/0172089 | A1 | 9/2004 | Whitehurst et al. |
| 2004/0176820 | A1 | 9/2004 | Paul |
| 2004/0243207 | A1 | 12/2004 | Olson et al. |
| 2005/0222657 | A1 | 10/2005 | Wahlstrand et al. |
| 2005/0283198 | A1 | 12/2005 | Haubrich |
| 2006/0015153 | A1 | 1/2006 | Gliner et al. |
| 2006/0050912 | A1 | 3/2006 | Kidd et al. |
| 2006/0064140 | A1 | 3/2006 | Whitehurst et al. |
| 2006/0167500 | A1 | 7/2006 | Towe et al. |
| 2006/0173510 | A1 | 8/2006 | Besio et al. |
| 2006/0190053 | A1 | 8/2006 | Dobak, III |
| 2006/0200208 | A1 | 9/2006 | Terry, Jr. et al. |
| 2006/0206165 | A1 | 9/2006 | Jaax et al. |
| 2006/0235484 | A1 | 10/2006 | Jaax et al. |
| 2006/0293723 | A1 | 12/2006 | Whitehurst et al. |
| 2007/0049988 | A1 | 3/2007 | Carbunaru et al. |
| 2007/0060975 | A1 | 3/2007 | Mannheimer et al. |
| 2007/0142874 | A1 | 6/2007 | John |
| 2007/0150025 | A1 | 6/2007 | Dilorenzo et al. |
| 2007/0150027 | A1 | 6/2007 | Rogers |
| 2007/0173908 | A1 | 7/2007 | Begnaud |
| 2007/0179557 | A1 | 8/2007 | Maschino et al. |
| 2007/0233194 | A1 | 10/2007 | Craig |
| 2007/0250145 | A1 | 10/2007 | Kraus et al. |
| 2007/0276451 | A1 | 11/2007 | Rigaux |
| 2008/0046013 | A1 | 2/2008 | Lozano |
| 2008/0103547 | A1 | 5/2008 | Okun et al. |
| 2008/0128215 | A1 | 6/2008 | Nowitz |
| 2008/0132980 | A1 | 6/2008 | Gerber |
| 2008/0140151 | A1 | 6/2008 | Brodkey |
| 2008/0147141 | A1 | 6/2008 | Testerman et al. |
| 2008/0161713 | A1 | 7/2008 | Leyde et al. |
| 2008/0171929 | A1 | 7/2008 | Katims |
| 2008/0172101 | A1 | 7/2008 | Bolea et al. |
| 2008/0262566 | A1 | 10/2008 | Jaax |
| 2008/0269716 | A1 | 10/2008 | Bonde et al. |
| 2008/0275327 | A1 | 11/2008 | Faarbaek et al. |
| 2009/0048642 | A1 | 2/2009 | Goroszeniuk |
| 2009/0210028 | A1 | 8/2009 | Rigaux et al. |
| 2009/0287035 | A1 | 11/2009 | Dietrich et al. |
| 2010/0030227 | A1 | 2/2010 | Kast et al. |
| 2010/0114240 | A1 | 5/2010 | Guntinas-Lichius et al. |
| 2010/0198044 | A1 | 8/2010 | Gehman et al. |
| 2010/0198282 | A1 | 8/2010 | Rogers |
| 2010/0222847 | A1 | 9/2010 | Goetz |
| 2010/0228105 | A1 | 9/2010 | Policker et al. |
| 2010/0228113 | A1 | 9/2010 | Solosko et al. |
| 2010/0262205 | A1 | 10/2010 | De Ridder |
| 2011/0093033 | A1 | 4/2011 | Nekhendzy |
| 2011/0106220 | A1 | 5/2011 | DeGiorgio et al. |
| 2011/0112603 | A1 | 5/2011 | DeGiorgio et al. |
| 2011/0184489 | A1 | 7/2011 | Nicolelis et al. |
| 2011/0218589 | A1 | 9/2011 | DeGiorgio et al. |
| 2011/0218590 | A1 | 9/2011 | DeGiorgio et al. |
| 2011/0270361 | A1 | 11/2011 | Borsody |
| 2011/0282129 | A1 | 11/2011 | Rigaux |
| 2011/0282412 | A1 | 11/2011 | Glukhovsky et al. |
| 2011/0288610 | A1 | 11/2011 | Brocke |
| 2012/0203301 | A1 | 8/2012 | Cameron et al. |
| 2012/0330380 | A1 | 12/2012 | Corndorf |
| 2013/0158626 | A1 | 6/2013 | DeGiorgio et al. |
| 2014/0039572 | A1 | 2/2014 | Bradley |
| 2014/0046407 | A1 | 2/2014 | Ben-Ezra et al. |
| 2014/0081353 | A1 | 3/2014 | Cook et al. |
| 2014/0081369 | A1 | 3/2014 | Sosa et al. |
| 2014/0135886 | A1 | 5/2014 | Cook et al. |
| 2014/0142669 | A1 | 5/2014 | Cook et al. |

(56) References Cited

U.S. PATENT DOCUMENTS

| | | |
|---|---|---|
| 2014/0148872 A1 | 5/2014 | Goldwasser et al. |
| 2014/0188200 A1 | 7/2014 | DeGiorgio et al. |
| 2014/0206945 A1 | 7/2014 | Liao |
| 2015/0151128 A1 | 6/2015 | DeGiorgio et al. |
| 2016/0106979 A1 | 4/2016 | DeGiorgio |
| 2016/0129254 A1 | 5/2016 | DeGiorgio et al. |
| 2016/0317814 A1 | 11/2016 | DeGiorgio et al. |
| 2016/0339242 A1 | 11/2016 | Cook et al. |
| 2017/0028198 A1 | 2/2017 | DeGiorgio et al. |
| 2017/0056660 A1 | 3/2017 | DeGiorgio et al. |
| 2017/0259063 A1 | 9/2017 | DeGiorgio et al. |
| 2017/0348521 A1 | 12/2017 | Cook et al. |
| 2018/0001077 A1 | 1/2018 | Cook et al. |

FOREIGN PATENT DOCUMENTS

| | | |
|---|---|---|
| JP | 7289649 A | 11/1995 |
| JP | 8-229141 A | 10/1996 |
| JP | 8-299141 A | 10/1996 |
| JP | 2007-061267 A | 3/2007 |
| JP | 2007061267 A | 3/2007 |
| JP | 2007-54299 A | 8/2007 |
| JP | 2008-506464 T | 3/2008 |
| JP | 2008506464 A | 3/2008 |
| JP | 2008-516696 A | 5/2008 |
| JP | 2008-246040 A | 10/2008 |
| JP | 2009-502315 A | 1/2009 |
| JP | 2009-505689 A | 2/2009 |
| JP | 2009-531154 A | 9/2009 |
| JP | 4961558 B2 | 6/2012 |
| JP | 2003-339884 A | 12/2013 |
| RU | 2086227 C1 | 8/1997 |
| RU | 2185092 C1 | 7/2002 |
| SU | 1718976 A1 | 3/1992 |
| WO | 2005/062829 A2 | 7/2005 |
| WO | 2006/044792 A2 | 4/2006 |
| WO | 2006/044792 A3 | 4/2006 |
| WO | 2006/044793 A2 | 4/2006 |
| WO | 2006044793 A2 | 4/2006 |
| WO | 2006/051370 | 5/2006 |
| WO | 2006051370 A1 | 5/2006 |
| WO | 2007/018793 A1 | 2/2007 |
| WO | 2007/018797 A1 | 2/2007 |
| WO | 2007/136726 | 11/2007 |
| WO | 2007136726 | 11/2007 |
| WO | 2008/128215 A1 | 10/2008 |
| WO | 2008128215 A1 | 10/2008 |
| WO | 2009/158389 | 12/2009 |
| WO | 2009158389 | 12/2009 |
| WO | 2010/057998 A1 | 5/2010 |
| WO | 2010057998 A1 | 5/2010 |
| WO | 2011/044173 | 4/2011 |
| WO | 2011/044176 | 4/2011 |
| WO | 2011/044178 | 4/2011 |
| WO | 2011/044179 | 4/2011 |
| WO | 2011044173 | 4/2011 |
| WO | 2011044176 | 4/2011 |
| WO | 2011044178 | 4/2011 |
| WO | 2011044179 | 4/2011 |
| WO | 2012/075192 A2 | 6/2012 |
| WO | 2012/082960 | 6/2012 |
| WO | 2012/082961 | 6/2012 |
| WO | 2012075192 A2 | 6/2012 |
| WO | 2012082960 | 6/2012 |
| WO | 2012082961 | 6/2012 |
| WO | 2013/104552 A1 | 7/2013 |
| WO | 2013104552 A1 | 7/2013 |
| WO | 2013/152316 A1 | 10/2013 |
| WO | 2013152316 A1 | 10/2013 |

OTHER PUBLICATIONS

Ahmed, H.E. et al., Use of Percutaneous Electrical Nerve Stimulation (PENS) in the Short-term Management of Headache, Headache, 40:311-315 (2000).

Allais, G. et al., Non-pharmacological approaches to chronic headaches: transcutaneous electrical nerve stimulation, lasertherapy and acupuncture in transformed migraine treatment, Neuro Sci, 24:S138-S142 (2003).

Degiorgio, C. et al., Trigeminal nerve stimulation for epilepsy, Neurology, 61:421-422 (2003).

Moseley, B.D. et al., Refractory status epilepticus treated with trigeminal nerve stimulation, Epilepsy Research, 108:600-603 (2014).

Degiorgio, C.et al., "Pilot Study of TrigeminalNerve Stimulation (TNS) for Epilepsy: A Proof-of-Concept Trial". Epilepsia, 47(7):1213-1215 (2006).

Moseley, B.D. and Degiorgio,C., "Refractory status epilepticus treated with trigeminal nerve stimulation." Epilepsy Research, 108: 600-603 (2014).

Cherkasova, Mariya V et al., Neuroimaging in Attention-Deficit Hyperactivity Disorder: Beyond the Frontostriatal Circuity, The Canadian Journal of Psychiatry, vol. 54, No. 10, Oct. 2009, 651-664.

Dickstein, Steven G. et al., The neural correlates of attention deficit hyperactivity disorder: an ALE meta-analysis, Journal of Child Psychology and Psychiatry, 47:10(2006), pp. 1051-1062.

Hall, Goeffrey B.C. et al., Enhanced Salience and Emotion Recognition in Autism: A PET Study, Am J Psychiatry, 160:8, Aug. 2003, http://ajp.psychiatryonline.org., 1439-1441.

Konrad, Kerstin et al., Dysfunctional Attentional Networks in Children with Attention Deficit/Hyperactivity Disorder: Evidence from an Event-Related Functional Magnetic Resonance Imaging Study, Biol Psychiatry, 2006, 59:643-651.

McAlonan, Grainne M. et al., Mapping the brain in autism. A voxel-based MRI study of volumetric differences and intercorrelations in autism, Brain (2005), 128, 268-276.

Makris, Nikos et al., Anterior Cingulate Volumetric Alterations in Treatment-Naive Adults with ADHD, J Atten Disord. Jan. 2010; 13(4): 407-413. doi:10.1177/1087054709351671.

Office Action dated Jan. 10, 2018 in U.S. Appl. No. 15/650,707, filed Jul. 14, 2017, (42pages).

Degiorgio Christopher M. et al., Trigeminal Nerve Stimulation for Epilepsy: Long-Term Feasibility and Efficacy, Neurology, Mar. 10, 2009, vol. 72, No. 10, 936-938.

Narouze et al., Supraorbital Nerve Electric Stimulation for the Treatment of Intractable Chronic Cluster Headache: A Case Report, Jul. 2007.

Reed et al., Combined occipital and supraorbital neurostimulation for the treatment of chronic migraine headaches: Initial experience, published online Feb. 15, 2010.

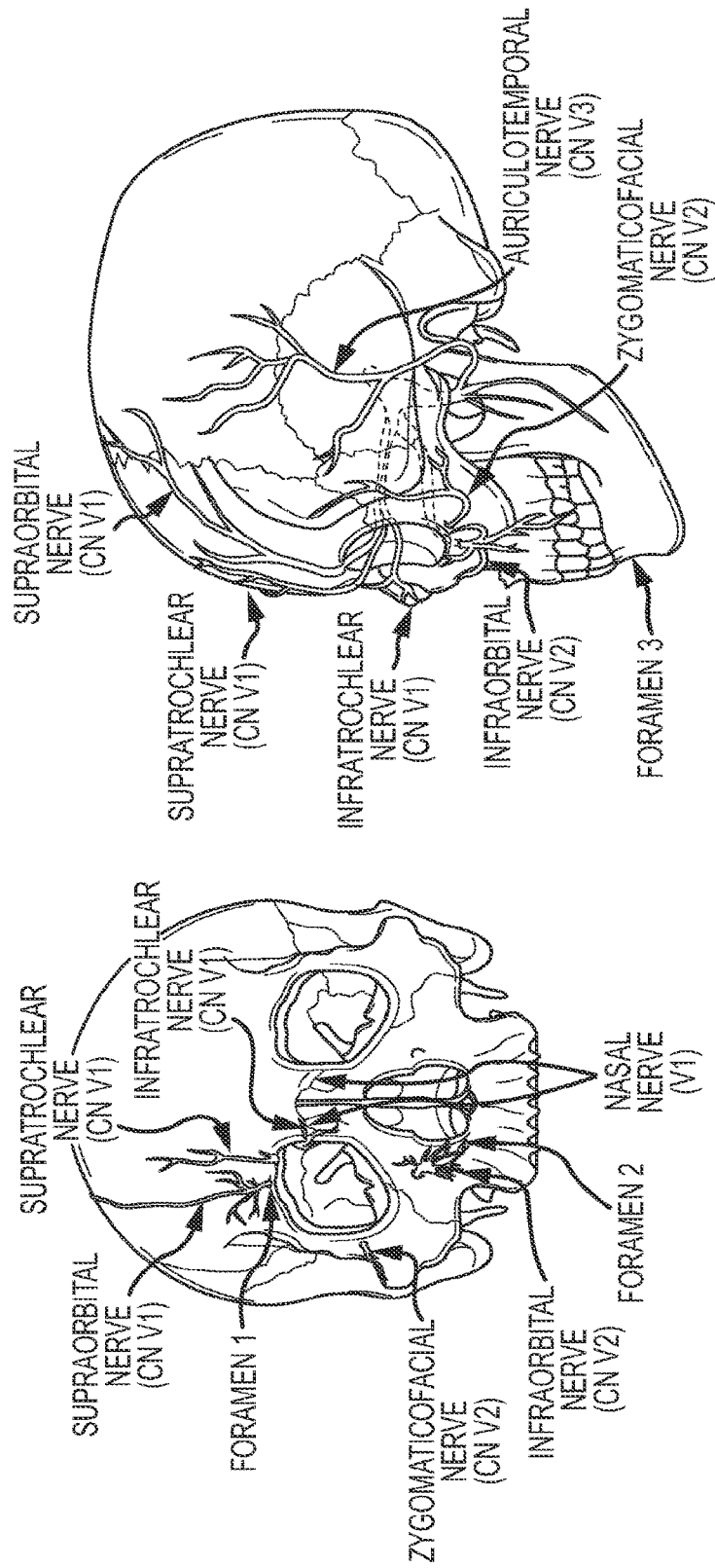

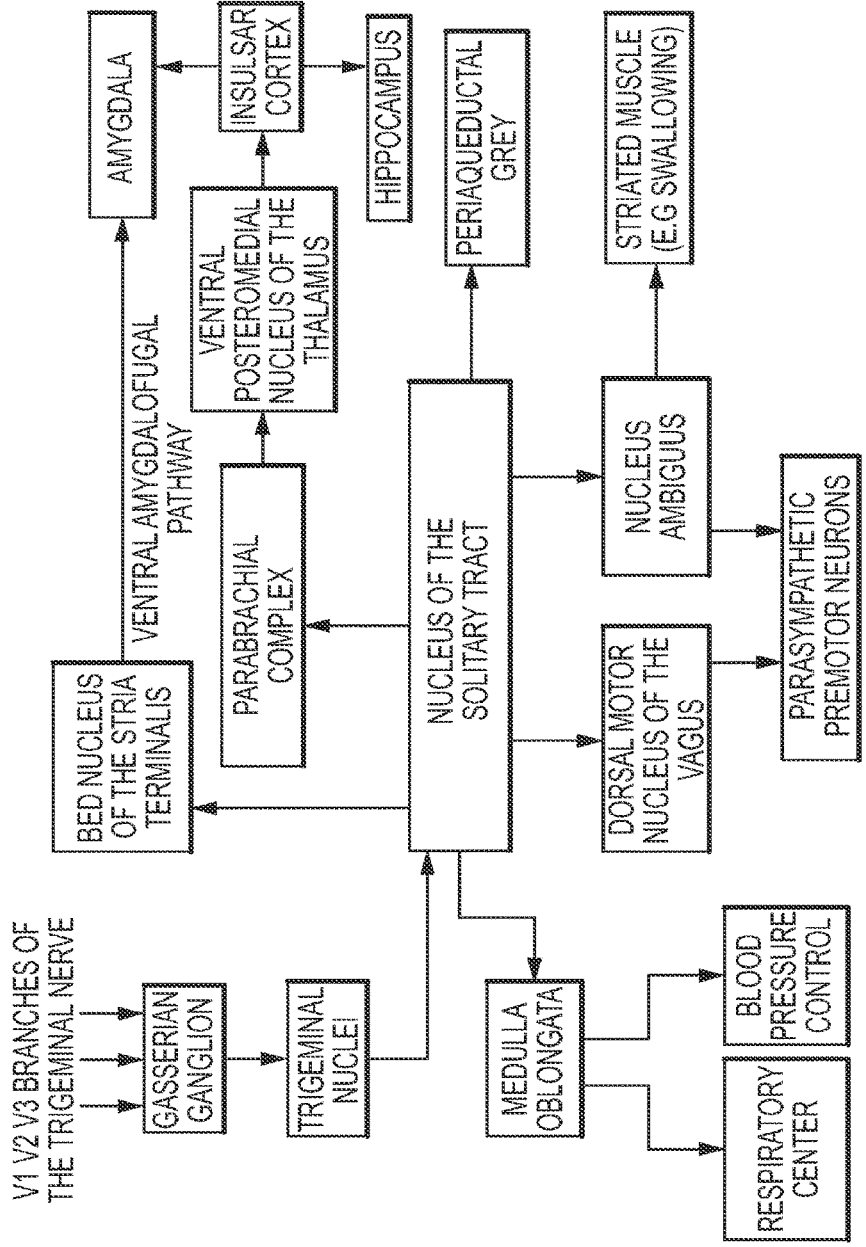

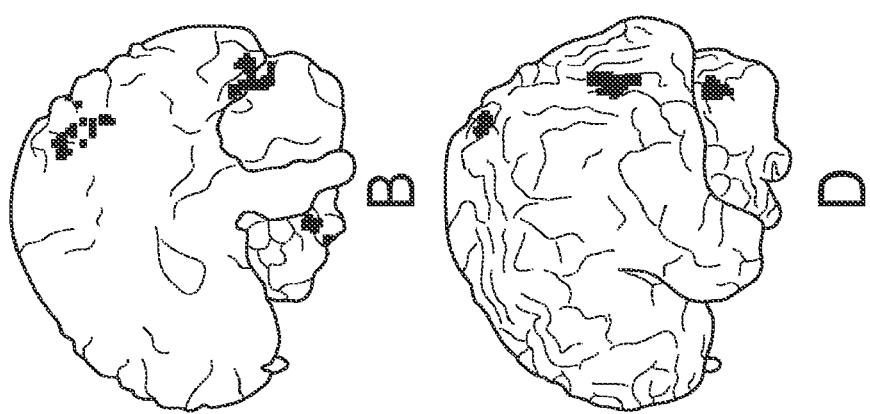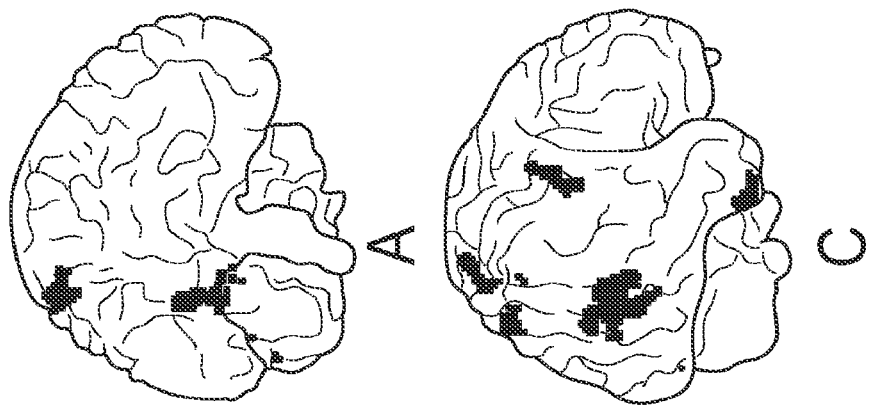
FIG. 3

PRE- TO POST-TREATMENT COMPARISON

| | BDI | HDRS$_{28}$ | HDRS$_{17}$ | QIDS$_{16}$ |
|---|---|---|---|---|
| BASELINE | 26.8 (8.1) | 25.4 (3.9) | 16.2 (3.3) | 10.8 (2.8) |
| FINAL | 8.4 (4.9) | 12.6 (6.4) | 8.8 (4.4) | 5.4 (3.8) |
| 2-TAIL P-VALUE | 0.0004 | 0.006 | 0.005 | 0.01 |
| % CHANGE | 70.2% | 51.1% | 45.6% | 58.1% |
| COHEN'S d E.S | 2.7 | 2.4 | 1.9 | 1.3 |

| PULSE DURATION (Usec) | 150us | 200us | 250us |
|---|---|---|---|
| mA'S RECORDED (MAX TOLERATED SETTINGS) | 7.92 | 5.94 | 5.72 |
| ELECTRODE RADIUS(cm) (1.25" DIAMETER ROUND ELECTRODES) | 1.59cm | 1.59cm | 1.59cm |
| SURFACE AREA cm | 7.92cm$^2$ | 7.92cm$^2$ | 7.92cm$^2$ |
| CURRENT DENSITY mA/cm$^2$ | 1 | .75 | .72 |
| MAXIMUM SAFE CURRENT DENSITY AT STIMULATING ELECTRODE mA/cm$^2$ | 25 | 25 | 25 |
| CHARGE DENSITY (A)(pulse)/cm$^2$ =uC/cm$^2$ AT STIMULATING ELECTRODE | .15 | .15 | 0.18 |
| MAXIMUM SAFE CHARGE DENSITY (uC/cm$^2$) AT BRAIN | 10 | 10 | 10 |

FIG.11

| MINUTES | ON TIME | OFF TIME | DUTY CYCLE |
| --- | --- | --- | --- |
| 10 | 10 SECONDS | 60 SECONDS | 12.50% |
| 20 | 20 SECONDS | 60 SECONDS | 25% |
| 30 | 30 SECONDS | 60 SECONDS | 33% |
| 40 | 30 SECONDS | 60 SECONDS | 33% |
| 50 | 20 SECONDS | 60 SECONDS | 25% |
| 60 | 10 SECONDS | 60 SECONDS | 12.50% |
| 70 | 20 SECONDS | 30 SECONDS | 40% |
| 80 | 30 SECONDS | 30 SECONDS | 50% |
| 90 | 30 SECONDS | 30 SECONDS | 50% |
| 100 | 20 SECONDS | 30 SECONDS | 40% |
| 120 | 10 SECONDS | 30 SECONDS | 25% |
| 130 | 10 SECONDS | 60 SECONDS | 12.50% |
| 140 | 20 SECONDS | 60 SECONDS | 25% |
| 150 | 30 SECONDS | 60 SECONDS | 33% |
| 160 | 30 SECONDS | 60 SECONDS | 33% |
| 170 | 20 SECONDS | 60 SECONDS | 25% |
| 180 | 10 SECONDS | 60 SECONDS | 12.50% |

FIG.14A

EXTRACRANIAL IMPLANTABLE DEVICES, SYSTEMS AND METHODS FOR THE TREATMENT OF MEDICAL DISORDERS

CROSS REFERENCE TO RELATED APPLICATIONS

This application is a continuation of U.S. application Ser. No. 15/624,640, filed Jun. 15, 2017, which is a continuation of U.S. application Ser. No. 13/994,512, filed Jan. 24, 2014, which is a U.S. National Stage filing under 35 U.S.C. § 371 of PCT Patent Application No. PCT/US2011/065003, filed Dec. 14, 2011, which itself claims the benefit of priority under 35 U.S.C. § 119(e) to the following applications: U.S. Application No. 61/423,008 entitled "Extracranial Implantable Devices, Systems and Methods for Treatment of Neuropsychiatric Disorders," filed Dec. 14, 2010; U.S. Application No. 61/440,802 entitled "Extracranial Implantable Devices, Systems and Methods for the Treatment of Cardiac Related Disorders" filed on Feb. 8, 2011; U.S. Application No. 61/445,454 entitled "Extracranial Implantable Devices, Systems and Methods for the Treatment of Fatigue and other Medical Disorders" filed Feb. 22, 2011; and U.S. Application No. 61/479,779 entitled "Extracranial Implantable Devices, Systems and Methods for the Treatment of Medical Disorders," filed Apr. 27, 2011, and each of the above applications is hereby incorporated by reference as though fully set forth herein.

U.S. application Ser. No. 13/994,512 is a continuation-in-part of U.S. application Ser. No. 12/898,685 entitled "Extracranial Implantable Devices, Systems and Methods for Treatment of Neuropsychiatric Disorders," filed Oct. 5, 2010, now issued as U.S. Pat. No. 8,958,880, which claims the benefit of priority under 35 U.S.C. § 119(e) to the following applications: U.S. Application No. 61/248,827, entitled "Devices and Methods for Treatment of Psychiatric Disorders," filed Oct. 5, 2009; U.S. Application No. 61/289,829, entitled "Extracranial Implantable Devices, Systems and Methods for Treatment of Neuropsychiatric Disorders," filed Dec. 23, 2009; U.S. Application No. 61/305,514, entitled "Systems, Devices and Methods for Treatment of Neurological Disorders and Conditions," filed Feb. 17, 2010; and U.S. Application No. 61/354,641, entitled "Extracranial Implantable Devices, Systems and Methods for Treatment of Neurological Disorders," filed Jun. 14, 2010, and each of the above applications is hereby incorporated by reference as though fully set forth herein.

U.S. application Ser. No. 13/994,512 is a continuation in part of U.S. application Ser. No. 12/898,696, entitled "Extracranial Implantable Devices, Systems and Methods for Treatment of Neurological Disorders" filed on Oct. 5, 2010, which claims the benefit of priority under 35 U.S.C. § 119(e) to the following applications: U.S. Application No. 61/248,827, entitled "Devices and Methods for Treatment of Psychiatric Disorders," filed Oct. 5, 2009; U.S. Application No. 61/289,829, entitled "Extracranial Implantable Devices, Systems and Methods for Treatment of Neuropsychiatric Disorders," filed Dec. 23, 2009; U.S. Application No. 61/305,514, entitled "Systems, Devices and Methods for Treatment of Neurological Disorders and Conditions," filed Feb. 17, 2010; and U.S. Application No. 61/354,641, entitled "Extracranial Implantable Devices, Systems and Methods for Treatment of Neurological Disorders," filed Jun. 14, 2010, and each of the above applications is hereby incorporated by reference as though fully set forth herein.

This application is related to copending U.S. Published Patent Application No. 2014/0135886, entitled "Devices, Systems and Methods for the Treatment of Medical Disorders," filed on Dec. 14, 2011, which is hereby incorporated by reference as though fully set forth herein.

FIELD

The present disclosure generally relates to implantable neurostimulator systems, devices and methods of using the same and more particularly relates to implantable neurostimulator systems, devices and methods including at least one implantable electrode for the treatment of medical disorders, such as neuropsychiatric disorders including mood, cognitive and behavioral disorders, heart disease and other cardiac related disorders, and fatigue, by stimulating superficial, cutaneous elements of cranial nerve(s).

BACKGROUND

Many medical disorders, including neuropsychiatric disorders, cardiac related disorders and fatigue are traditionally treated with pharmacotherapy and/or psychotherapy. However, a substantial percentage of patients with these and other conditions do not recover despite multiple trials of treatment and there may be significant and long term side effects to the traditional treatment methods.

For example, interventions for fatigue commonly employ medications, particularly psychostimulant medications. Such medications include methylphenidate, amantadine, pemoline, and modafinil (reviewed by Peuckmann et al., Cochrane Database Syst Rev 2010, 11:CD006788). These medications carry potential for side effects, such as blurred vision, depression or anxiety, liver failure, psychosis, suicidal thinking, swelling of the hands/leg/feet, shortness of breath, palpitations, elevated blood pressure, anorexia and addiction.

For some medical disorders, brain stimulation has been a primary treatment alternative, and electroconvulsive therapy (ECT, or "electroshock" therapy) has been the dominant brain stimulation approach since the first part of the 20th century. ECT carries risks of memory and other cognitive side effects, considerable cost, and risks of anesthesia. Two implantable approaches have also been described: deep brain stimulation (DBS), in which electrodes are implanted directly within the brain, and vagus nerve stimulation (VNS) in which stimulating electrodes are implanted on the vagus nerve in the neck. While the U.S. Food and Drug Administration (FDA) have approved systems for deep brain stimulation for the treatment of essential tremor, Parkinson's disease, dystonia and obsessive compulsive disorder, DBS is presently an experimental intervention for other neuropsychiatric conditions. The risks of DBS include infection, hemorrhage, and injury to deep brain structures. In reports of clinical studies with VNS, many of the patients who undergo VNS treatments do not achieve remission, and there is no reliable predictor of good outcomes from the implanted VNS device.

Against this backdrop, the present disclosure is provided. The information included in this Background section of the specification, including any references cited herein and any description or discussion thereof, is included for technical reference purposes only and is not to be regarded as subject matter by which the scope of the invention is to be bound.

SUMMARY

One aspect of the subject matter of the present disclosure addresses the aforementioned needs by providing a method of treating medical disorders and systems and devices configured to stimulate the ophthalmic (supra-orbital), infraorbital, and mentalis branches of the trigeminal nerve to treat medical disorders with minimally invasive, implantable and easy-to-use devices and systems.

In another aspect of the present disclosure, an implantable electrode assembly configured for trigeminal nerve stimulation is provided.

In yet another aspect of the present disclosure, a method of treating medical disorders using the disclosed implantable electrode assembly is provided.

In one aspect, a system for trigeminal nerve stimulation for treatment of a medical disorder is provided. The system includes a pulse generator and a implantable electrode assembly in electrical communication with the pulse generator. In one aspect, a first electrode comprising at least one contact configured for subcutaneous or percutaneous placement at a first region of the patient's face to be implanted in proximity to, adjacent to or in contact with at least one branch of the trigeminal nerve selected from the group consisting of: ophthalmic nerve, supraorbital nerve, infraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve, thereby stimulating the trigeminal nerve to modulate at least one body system for treatment of a medical disorder selected from the group consisting of: cardiac related disorders, fatigue, tinnitus, obesity, diabetes, dyslipidemia, metabolic syndrome, obstructive sleep apnea, arthritis, cachexia/anorexia, inflammation, asthma, inflammatory bowel disease, atopic dermatitis, sepsis, hepatitis, disorders of regulation of breathing, disorders of gastrointestinal function, gastroesophageal reflux, diarrhea and constipation, dysphagia and other disturbances of swallowing, gastroparesis, functional bowel syndromes, post-operative ileus, dyspepsia, motion sickness, chemotherapy-related nausea and emesis, autonomic regulation in menopausal hot flashes, regulation of hemostasis, sleep/insomnia and a neuropsychiatric disorder selected from the group consisting of attention deficit disorder (ADD), attention deficit hyperactivity disorder (ADHD), autism and autism spectrum disorders (ASD), substance use disorders and related behavioral addictions, eating disorders and obsessive compulsive disorder (OCD), psychotic disorders, dementing disorders, or a combination thereof.

In one aspect, the medical disorder is a cardiac related disorder selected from the group consisting of heart disease, cardiac arrhythmias, myocardial infarction, sudden cardiac death after myocardial infarction, heart failure, cerebral ischemia, sudden infant death syndrome (SIDS), impaired blood flow conditions, atrial fibrillation or sudden death in epilepsy. The at least one branch of the trigeminal nerve is an ophthalmic nerve or an infraorbital nerve, wherein the body system is a trigeminal nerve cardiac reflex and wherein stimulation of the ophthalmic nerve or the infraorbital nerve modulates or activates the trigeminal nerve cardiac reflex to treat or prevent a cardiac related disorder. In one aspect, the system of claim 2, wherein the body system is a vagus nerve circuit, and wherein stimulation of the at least one branch of the trigeminal nerve modulates the vagus nerve circuit to treat a cardiac related disorder. In one aspect, the medical disorder is fatigue, wherein the body system is a locus coeruleus or a reticular activating system, and wherein stimulation of the at least one branch of the trigeminal nerve modulates the locus coeruleus or modulates the reticular activating system to treat fatigue. In one aspect, the medical disorder is selected from the group consisting of obesity and other disorders related to weight and feeding, inflammation, disorders of regulation of breathing, disorders of gastrointestinal function, autonomic regulation in menopausal hot flashes, regulation of hemostasis and sleep/insomnia, wherein the body system is a vagus nerve circuit, and wherein stimulation of the at least one branch of the trigeminal nerve modulates the vagus nerve circuit to treat said medical disorder. In one aspect, the medical disorder is a dementing disorder wherein the body system is a vagus nerve circuit or a trigeminal nerve cardiac reflex, and wherein stimulation of the at least one branch of the trigeminal nerve modulates the vagus nerve circuit or the trigeminal nerve cardiac reflex to treat said medical disorder.

In one aspect, the assembly further comprises a second electrode comprising at least one contact configured for cutaneous placement at a second region of the patient's face, wherein the second electrode is configured to contact a portion of the patient's face overlying the cutaneous distribution of at least one branch of the trigeminal nerve, wherein the at least one branch of the trigeminal nerve is selected from the group consisting of: ophthalmic nerve, infraorbital nerve, supraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve. In one embodiment, first electrode and the second electrode are configured to contact a portion of the patient's face overlying the cutaneous distribution of a same branch of the trigeminal nerve. In another embodiment, the first electrode and the second electrode are configured to contact a portion of the patient's face overlying the cutaneous distribution of a different branch of the trigeminal nerve. The stimulation may be provided uni- or bilaterally.

In one aspect, the system is configured for minimal current penetration into a brain of a patient. The system may further include a closed loop device configured to provide self-tuning adaptive feedback control to the system. In one embodiment, stimulation of the at least one branch of the trigeminal nerve is determined based on measurement of activity in a brain region to detect an acute biological change. In one embodiment, the at least one branch of the trigeminal nerve is stimulated at a first set of stimulation parameters for a first time period, at a second set of stimulation parameters for a second time period, and at a third set of stimulation parameters for a third time period. In one embodiment, the at least one branch of the trigeminal nerve is stimulated at the first, second and third set of parameters in a cycle at least twice. In one embodiment, the pulse generator is configured to apply electrical signals at a frequency between approximately 1 and 300 Hertz, at a pulse duration between approximately 50 and 500 microseconds, at an output current density of not greater than approximately 10 mA/cm$^2$ and an output charge density of not greater than approximately 10 microCoulomb/cm$^2$ at the cerebral cortex.

In one aspect, an implantable electrode assembly for trigeminal nerve stimulation for treatment of a medical disorder is provided. a first electrode comprising at least one contact configured for subcutaneous or percutaneous placement at a first region of the patient's face to be implanted in proximity to, adjacent to or in contact with at least one branch of the trigeminal nerve selected from the group consisting of: ophthalmic nerve, supraorbital nerve, infraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve, thereby stimulating the trigeminal nerve to modulate at least one body system for treatment of a medical disorder selected from the group consisting of: cardiac related disorders, fatigue, tinnitus, obesity, diabetes, dyslipidemia, metabolic syndrome, obstructive sleep apnea, arthritis, cachexia/anorexia, inflammation, asthma, inflammatory bowel disease, atopic dermatitis, sepsis, hepatitis, disorders of regulation of breathing, disorders of gastrointestinal function, gastroesophageal reflux, diarrhea and constipation, dysphagia and other disturbances of swallowing, gastroparesis, functional bowel syndromes, post-operative ileus, dyspepsia, motion sickness, chemotherapy-related nausea and emesis, autonomic regulation in menopausal hot flashes, regulation of hemostasis, sleep/insomnia and a neuropsychiatric disorder selected from the group consisting of attention deficit disorder (ADD), attention deficit hyperactivity disorder (ADHD), autism and autism spectrum disorders (ASD), substance use disorders and related behavioral addictions, eating disorders and obsessive compulsive disorder (OCD), psychotic disorders, dementing disorders or a combination thereof. In one embodiment, the assembly may further include a second electrode comprising at least one contact configured for cutaneous placement at a second region of the patient's face, wherein the second electrode is configured to contact a portion of the patient's face overlying the cutaneous distribution of at least one branch of the trigeminal nerve, wherein the at least one branch of the trigeminal nerve is selected from the group consisting of: ophthalmic nerve, supraorbital nerve, infraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve. In some embodiments, the first electrode and the second electrode are configured to contact a portion of the patient's face overlying the cutaneous distribution of a same branch of the trigeminal nerve. In some embodiments, the first electrode and the second electrode are configured to contact a portion of the patient's face overlying the cutaneous distribution of a different branch of the trigeminal nerve. In one embodiment, the medical disorder is a cardiac related disorder selected from the group consisting of heart disease, cardiac arrhythmias, myocardial infarction, sudden cardiac death after myocardial infarction, heart failure, cerebral ischemia, sudden infant death syndrome (SIDS), impaired blood flow conditions, atrial fibrillation or sudden death in epilepsy. In one embodiment, the body system is a vagus nerve circuit, and wherein stimulation of the at least one branch of the trigeminal nerve modulates the vagus nerve circuit to treat a cardiac related disorder. In one embodiment, the medical disorder is fatigue, wherein the body system is a locus coeruleus or a reticular activating system, and wherein stimulation of the at least one branch of the trigeminal nerve modulates the locus coeruleus or modulates the reticular activating system to treat fatigue. In one embodiment, the medical disorder is selected from the group consisting of obesity and other disorders related to weight and feeding, inflammation, disorders of regulation of breathing, disorders of gastrointestinal function, autonomic regulation in menopausal hot flashes, regulation of hemostasis and sleep/insomnia, wherein the body system is a vagus nerve circuit, and wherein stimulation of the at least one branch of the trigeminal nerve modulates the vagus nerve circuit to treat said medical disorder. In one embodiment, the medical disorder is a dementing disorder wherein the body system is a vagus nerve circuit or a trigeminal nerve cardiac reflex, and wherein stimulation of the at least one branch of the trigeminal nerve modulates the vagus nerve circuit or the trigeminal nerve cardiac reflex to treat said medical disorder.

In one embodiment, the assembly produces minimal current penetration into a brain of a patient.

In one aspect, a method for treating a medical disorder by trigeminal nerve stimulation is provided. The method includes implanting an implantable electrode assembly in proximity to, adjacent to or in contact with at least one branch of the trigeminal nerve to stimulate the trigeminal nerve for treatment of a medical disorder, the electrode assembly comprising: a first electrode comprising at least one contact for subcutaneous or percutaneous placement at a first region of a patient's face in proximity to, adjacent to or in contact with at least one branch of the trigeminal nerve selected from the group consisting of ophthalmic nerve, supraorbital nerve, infraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve; and applying electrical signals to the electrode assembly to stimulate the at least one branch of the trigeminal nerve to modulate a system of the patient's body for treatment of a medical disorder selected from the group consisting of: cardiac related disorders, fatigue, tinnitus, obesity, diabetes, dyslipidemia, metabolic syndrome, obstructive sleep apnea, arthritis, cachexia/anorexia, inflammation, asthma, inflammatory bowel disease, atopic dermatitis, sepsis, hepatitis, disorders of regulation of breathing, disorders of gastrointestinal function, gastroesophageal reflux, diarrhea and constipation, dysphagia and other disturbances of swallowing, gastroparesis, functional bowel syndromes, post-operative ileus, dyspepsia, motion sickness, chemotherapy-related nausea and emesis, autonomic regulation in menopausal hot flashes, regulation of hemostasis, sleep/insomnia and a neuropsychiatric disorder selected from the group consisting of attention deficit disorder (ADD), attention deficit hyperactivity disorder (ADHD), autism and autism spectrum disorders (ASD), substance use disorders and related behavioral addictions, eating disorders and obsessive compulsive disorder (OCD), psychotic disorders, dementing disorders or a combination thereof.

In one embodiment, the method may further include a second electrode comprising at least one contact configured for cutaneous placement at a second region of the patient's face, wherein the second electrode is configured to contact a portion of the patient's face overlying the cutaneous distribution of at least one branch of the trigeminal nerve, wherein the at least one branch of the trigeminal nerve is selected from the group consisting of: ophthalmic nerve, supraorbital nerve, infraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve. In one embodiment, step of applying electrical signals comprises applying electrical signals at a frequency between approximately 20 and 300 Hertz, at a current of 0.05 to 5 milliamperes (mA) and at a pulse duration of less than or equal to 500 microseconds. In one embodiment, the step of applying electrical signals comprises applying electrical signals at a frequency between approximately 20 and 300 Hertz, at a pulse duration between approximately 50 and 500 microseconds, at an output current density of not greater than approximately 10 $mA/cm^2$ and a charge density of not greater than approximately 10 $microCoulomb/cm^2$ at the cerebral cortex. In one embodiment, the step of applying electrical signals comprises applying electrical signals at an output current density of not greater than approximately 10 $mA/cm^2$. In one embodiment, the step of applying electrical signals comprises applying electrical signals at an output current density of between approximately 2.5 and 5 mA/cm². In one embodiment, the step of applying electrical signals comprises applying electrical signals at an output current density of not greater than approximately 7 mA/cm². In one embodiment, the step of applying electrical signals comprises applying electrical signals at an output current density of not greater than approximately 5 mA/cm². In one embodiment, the step of applying electrical signals comprises applying electrical signals to minimize current penetration into a brain of a patient. In one embodiment, the medical disorder is a cardiac related disorder selected from the group consisting of heart disease, cardiac arrhythmias, myocardial infarction, sudden cardiac death after myocardial infarction, heart failure, cerebral ischemia, sudden infant death syndrome (SIDS), impaired blood flow conditions, atrial fibrillation or sudden death in epilepsy. In one embodiment, the body system is a vagus nerve circuit, and wherein stimulation of the at least one branch of the trigeminal nerve modulates the vagus nerve circuit to treat a cardiac related disorder. In one embodiment, the medical disorder is fatigue, wherein the body system is a locus coeruleus or a reticular activating system, and wherein stimulation of the at least one branch of the trigeminal nerve modulates the locus coeruleus or modulates the reticular activating system to treat fatigue. In one embodiment, the medical disorder is selected from the group consisting of obesity and other disorders related to weight and feeding, inflammation, disorders of regulation of breathing, disorders of gastrointestinal function, autonomic regulation in menopausal hot flashes, regulation of hemostasis and sleep/insomnia, wherein the body system is a vagus nerve circuit, and wherein stimulation of the at least one branch of the trigeminal nerve modulates the vagus nerve circuit to treat said medical disorder. In one embodiment, the medical disorder is a dementing disorder wherein the body system is a vagus nerve circuit or a trigeminal nerve cardiac reflex, and wherein stimulation of the at least one branch of the trigeminal nerve modulates the vagus nerve circuit or the trigeminal nerve cardiac reflex to treat said medical disorder.

In one aspect, a kit for trigeminal nerve stimulation for treatment of a medical disorder. In one embodiment, the kit includes an implantable electrode assembly as disclosed elsewhere herein and instructions for applying the electrode assembly to a patient for treatment of a medical disorder, wherein the medical disorder is selected from the group consisting of: cardiac related disorders, fatigue, tinnitus, obesity, diabetes, dyslipidemia, metabolic syndrome, obstructive sleep apnea, arthritis, cachexia/anorexia, inflammation, asthma, inflammatory bowel disease, atopic dermatitis, sepsis, hepatitis, disorders of regulation of breathing, disorders of gastrointestinal function, gastroesophageal reflux, diarrhea and constipation, dysphagia and other disturbances of swallowing, gastroparesis, functional bowel syndromes, post-operative ileus, dyspepsia, motion sickness, chemotherapy-related nausea and emesis, autonomic regulation in menopausal hot flashes, regulation of hemostasis, sleep/insomnia and a neuropsychiatric disorder selected from the group consisting of attention deficit disorder (ADD), attention deficit hyperactivity disorder (ADHD), autism and autism spectrum disorders (ASD), substance use disorders and related behavioral addictions, eating disorders and obsessive compulsive disorder (OCD), psychotic disorders, dementing disorders or a combination thereof. The kit may also include a pulse generator and instructions for applying electrical signals to the electrode assembly for treatment of a medical disorder.

In one aspect, a method for initiation, activation or stimulation of a vagus nerve circuit by trigeminal nerve stimulation for treatment of a medical disorder is provided. The method may include implanting an implantable electrode assembly in a patient, the electrode assembly comprising: a first electrode comprising at least one contact configured for subcutaneous or percutaneous placement at a first region of the patient's face and configured to be implanted in proximity to, adjacent to or in contact with at least one branch of the trigeminal nerve, which is an ophthalmic nerve, supraorbital nerve, or an infraorbital nerve; and applying electrical signals to the electrode assembly to stimulate the at least one branch of the trigeminal nerve to modulate the vagus nerve circuit for treatment of a medical disorder which may benefit from vagus nerve stimulation via the trigeminal nerve. The at least one branch of the trigeminal nerve is an ophthalmic nerve or an infraorbital nerve. In one embodiment, the medical disorder is a cardiac related disorder selected from the group consisting of heart disease, cardiac arrhythmias, myocardial infarction, sudden cardiac death after myocardial infarction, heart failure, cerebral ischemia, sudden infant death syndrome (SIDS), impaired blood flow conditions, atrial fibrillation or sudden death in epilepsy. In one embodiment, the medical disorder is selected from the group consisting of obesity and other disorders related to weight and feeding, inflammation, disorders of regulation of breathing, disorders of gastrointestinal function, autonomic regulation in menopausal hot flashes, regulation of hemostasis and sleep/insomnia, and wherein stimulation of the at least one branch of the trigeminal nerve modulates the vagus nerve circuit to treat said medical disorder. In one embodiment, the medical disorder is a dementing disorder and wherein stimulation of the at least one branch of the trigeminal nerve modulates the vagus nerve circuit to treat said medical disorder.

In one aspect, an implantable device for polycranial nerve stimulation for treatment of a medical disorder is provided. The device includes a pulse generator; and an implantable electrode assembly in electrical communication with the pulse generator. The assembly includes at least one electrode for subcutaneous or percutaneous placement at a first region of the patient's ear and configured to be implanted in proximity to, adjacent to or in contact with at least one branch of the trigeminal nerve, and wherein stimulation of the at least one branch of the trigeminal nerve modulates a system in the body to treat a medical disorder.

In one embodiment, the at least one branch of the trigeminal nerve is selected from the group consisting of: ophthalmic nerve, infraorbital nerve, supraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve. In one embodiment, the device further includes a second electrode comprising at least one contact configured for subcutaneous or percutaneous placement at a second region of the patient's face, wherein the second electrode is configured to be implanted in proximity to, adjacent to or in contact with at least one branch of the trigeminal nerve, wherein the at least one branch of the trigeminal nerve is selected from the group consisting of: ophthalmic nerve, infraorbital nerve, supraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve. In one embodiment, the first electrode and the second electrode are configured for implantation in proximity to, adjacent to or in contact with a same branch of the trigeminal nerve. In one embodiment, the first electrode and the second electrode are configured for implantation in proximity to, adjacent to or in contact with a different branch of the trigeminal nerve. The device produces minimal current penetration into a brain of a patient. The device may further include a closed loop device configured to provide self-tuning adaptive feedback control to the system. Stimulation of the at least one branch of the trigeminal nerve is determined based on measurement of activity in a brain region to detect an acute biological change. In one embodiment, the at least one branch of the trigeminal nerve is stimulated at a first set of stimulation parameters for a first time period, at a second set of stimulation parameters for a second time period, and at a third set of stimulation parameters for a third time period. In one embodiment, the at least one branch of the trigeminal nerve is stimulated at the first, second and third set of parameters in a cycle at least twice. In one embodiment, the pulse generator is configured to apply electrical signals at a frequency between approximately 1 and 300 Hertz, at a pulse duration between approximately 50 and 500 microseconds, at an output current density of not greater than approximately 10 mA/cm$^2$ and an output charge density of not greater than approximately 10 microCoulomb/cm$^2$ at the cerebral cortex. In one embodiment, the pulse generator is configured to apply electrical signals at an output current density of not greater than approximately 10 mA/cm$^2$. In one embodiment, the pulse generator is configured to apply electrical signals at an output current density of between approximately 2.5 and 5 mA/cm$^2$. In one embodiment, the pulse generator is configured to apply electrical signals at an output current density of not greater than approximately 7 mA/cm$^2$. In one embodiment, the pulse generator is configured to apply electrical signals at an output current density of not greater than approximately 5 mA/cm$^2$. In one embodiment, the medical disorder is selected from the group consisting of: neurological disorders, cardiac related disorders, fatigue, tinnitus, obesity, diabetes, dyslipidemia, metabolic syndrome, obstructive sleep apnea, arthritis, cachexia/anorexia, inflammation, asthma, inflammatory bowel disease, atopic dermatitis, sepsis, hepatitis, disorders of regulation of breathing, disorders of gastrointestinal function, gastroesophageal reflux, diarrhea and constipation, dysphagia and other disturbances of swallowing, gastroparesis, functional bowel syndromes, post-operative ileus, dyspepsia, motion sickness, chemotherapy-related nausea and emesis, autonomic regulation in menopausal hot flashes, regulation of hemostasis, sleep/insomnia and a neuropsychiatric disorder selected from the group consisting of depression, attention deficit disorder (ADD), attention deficit hyperactivity disorder (ADHD), autism and autism spectrum disorders (ASD), substance use disorders and related behavioral addictions, eating disorders and obsessive compulsive disorder (OCD), psychotic disorders, dementing disorders, or a combination thereof. In one embodiment, the medical disorder is a cardiac related disorder selected from the group consisting of heart disease, cardiac arrhythmias, myocardial infarction, sudden cardiac death after myocardial infarction, heart failure, cerebral ischemia, sudden infant death syndrome (SIDS), impaired blood flow conditions, atrial fibrillation or sudden death in epilepsy. In one embodiment, the at least one branch of the trigeminal nerve is an ophthalmic nerve or an infraorbital nerve, wherein the body system is a trigeminal nerve cardiac reflex and wherein stimulation of the ophthalmic nerve or the infraorbital nerve modulates or activates the trigeminal nerve cardiac reflex to treat or prevent a cardiac related disorder. In one embodiment, the body system is a vagus nerve circuit, and wherein stimulation of the at least one branch of the trigeminal nerve modulates the vagus nerve circuit to treat a cardiac related disorder. In one embodiment, the medical disorder is fatigue, wherein the body system is a locus coeruleus or a reticular activating system, and wherein stimulation of the at least one branch of the trigeminal nerve modulates the locus coeruleus or modulates the reticular activating system to treat fatigue. In one embodiment, the medical disorder is selected from the group consisting of obesity and other disorders related to weight and feeding, inflammation, disorders of regulation of breathing, disorders of gastrointestinal function, autonomic regulation in menopausal hot flashes, regulation of hemostasis and sleep/insomnia, wherein the body system is a vagus nerve circuit, and wherein stimulation of the at least one branch of the trigeminal nerve modulates the vagus nerve circuit to treat said medical disorder. In one embodiment, the medical disorder is a dementing disorder wherein the body system is a vagus nerve circuit or a trigeminal nerve cardiac reflex, and wherein stimulation of the at least one branch of the trigeminal nerve modulates the vagus nerve circuit or the trigeminal nerve cardiac reflex to treat said medical disorder.

In one aspect, use of the device for polycranial stimulation as disclosed herein for treatment of a medical disorder is provided. The medical disorder is selected from the group consisting of: cardiac related disorders, fatigue, tinnitus, obesity, diabetes, dyslipidemia, metabolic syndrome, obstructive sleep apnea, arthritis, cachexia/anorexia, inflammation, asthma, inflammatory bowel disease, atopic dermatitis, sepsis, hepatitis, disorders of regulation of breathing, disorders of gastrointestinal function, gastroesophageal reflux, diarrhea and constipation, dysphagia and other disturbances of swallowing, gastroparesis, functional bowel syndromes, post-operative ileus, dyspepsia, motion sickness, chemotherapy-related nausea and emesis, autonomic regulation in menopausal hot flashes, regulation of hemostasis, sleep/insomnia and a neuropsychiatric disorder selected from the group consisting of attention deficit disorder (ADD), attention deficit hyperactivity disorder (ADHD), autism and autism spectrum disorders (ASD), substance use disorders and related behavioral addictions, eating disorders and obsessive compulsive disorder (OCD), psychotic disorders, dementing disorders, or a combination thereof. In one embodiment, the medical disorder is a cardiac related disorder selected from the group consisting of heart disease, cardiac arrhythmias, myocardial infarction, sudden cardiac death after myocardial infarction, heart failure, cerebral ischemia, sudden infant death syndrome (SIDS), impaired blood flow conditions, atrial fibrillation or sudden death in epilepsy. In one embodiment, the at least one branch of the trigeminal nerve is an ophthalmic nerve or an infraorbital nerve, wherein the body system is a trigeminal nerve cardiac reflex and wherein stimulation of the ophthalmic nerve or the infraorbital nerve modulates or activates the trigeminal nerve cardiac reflex to treat or prevent a cardiac related disorder. In one embodiment, the body system is a vagus nerve circuit, and wherein stimulation of the at least one branch of the trigeminal nerve modulates the vagus nerve circuit to treat a cardiac related disorder. In one embodiment, the medical disorder is fatigue, wherein the body system is a locus coeruleus or a reticular activating system, and wherein stimulation of the at least one branch of the trigeminal nerve modulates the locus coeruleus or modulates the reticular activating system to treat fatigue. In one embodiment, the medical disorder is selected from the group consisting of obesity and other disorders related to weight and feeding, inflammation, disorders of regulation of breathing, disorders of gastrointestinal function, autonomic regulation in menopausal hot flashes, regulation of hemostasis and sleep/insomnia, wherein the body system is a vagus nerve circuit, and wherein stimulation of the at least one branch of the trigeminal nerve modulates the vagus nerve circuit to treat said medical disorder. In one embodiment, the medical disorder is a dementing disorder wherein the body system is a vagus nerve circuit or a trigeminal nerve cardiac reflex, and wherein stimulation of the at least one branch of the trigeminal nerve modulates the vagus nerve circuit or the trigeminal nerve cardiac reflex to treat said medical disorder.

In one aspect use of the system as disclosed elsewhere herein for treatment of a medical disorder is provided. The medical disorder is selected from the group consisting of: cardiac related disorders, fatigue, tinnitus, obesity, diabetes, dyslipidemia, metabolic syndrome, obstructive sleep apnea, arthritis, cachexia/anorexia, inflammation, asthma, inflammatory bowel disease, atopic dermatitis, sepsis, hepatitis, disorders of regulation of breathing, disorders of gastrointestinal function, gastroesophageal reflux, diarrhea and constipation, dysphagia and other disturbances of swallowing, gastroparesis, functional bowel syndromes, post-operative ileus, dyspepsia, motion sickness, chemotherapy-related nausea and emesis, autonomic regulation in menopausal hot flashes, regulation of hemostasis, sleep/insomnia and a neuropsychiatric disorder selected from the group consisting of attention deficit disorder (ADD), attention deficit hyperactivity disorder (ADHD), autism and autism spectrum disorders (ASD), substance use disorders and related behavioral addictions, eating disorders and obsessive compulsive disorder (OCD), psychotic disorders, dementing disorders, or a combination thereof. In one embodiment, the medical disorder is a cardiac related disorder selected from the group consisting of heart disease, cardiac arrhythmias, myocardial infarction, sudden cardiac death after myocardial infarction, heart failure, cerebral ischemia, sudden infant death syndrome (SIDS), impaired blood flow conditions, atrial fibrillation or sudden death in epilepsy. In one embodiment, the at least one branch of the trigeminal nerve is an ophthalmic nerve or an infraorbital nerve, wherein the body system is a trigeminal nerve cardiac reflex and wherein stimulation of the ophthalmic nerve or the infraorbital nerve modulates or activates the trigeminal nerve cardiac reflex to treat or prevent a cardiac related disorder. In one embodiment, the body system is a vagus nerve circuit, and wherein stimulation of the at least one branch of the trigeminal nerve modulates the vagus nerve circuit to treat a cardiac related disorder. In one embodiment, the medical disorder is fatigue, wherein the body system is a locus coeruleus or a reticular activating system, and wherein stimulation of the at least one branch of the trigeminal nerve modulates the locus coeruleus or modulates the reticular activating system to treat fatigue. In one embodiment, the medical disorder is selected from the group consisting of obesity and other disorders related to weight and feeding, inflammation, disorders of regulation of breathing, disorders of gastrointestinal function, autonomic regulation in menopausal hot flashes, regulation of hemostasis and sleep/insomnia, wherein the body system is a vagus nerve circuit, and wherein stimulation of the at least one branch of the trigeminal nerve modulates the vagus nerve circuit to treat said medical disorder.

In one aspect, use of the assembly as disclosed elsewhere herein for treatment of a medical disorder is provided. The medical disorder is selected from the group consisting of: cardiac related disorders, fatigue, tinnitus, obesity, diabetes, dyslipidemia, metabolic syndrome, obstructive sleep apnea, arthritis, cachexia/anorexia, inflammation, asthma, inflammatory bowel disease, atopic dermatitis, sepsis, hepatitis, disorders of regulation of breathing, disorders of gastrointestinal function, gastroesophageal reflux, diarrhea and constipation, dysphagia and other disturbances of swallowing, gastroparesis, functional bowel syndromes, post-operative ileus, dyspepsia, motion sickness, chemotherapy-related nausea and emesis, autonomic regulation in menopausal hot flashes, regulation of hemostasis, sleep/insomnia and a neuropsychiatric disorder selected from the group consisting of attention deficit disorder (ADD), attention deficit hyperactivity disorder (ADHD), autism and autism spectrum disorders (ASD), substance use disorders and related behavioral addictions, eating disorders and obsessive compulsive disorder (OCD), psychotic disorders, dementing disorders, or a combination thereof. In one embodiment, the medical disorder is a cardiac related disorder selected from the group consisting of heart disease, cardiac arrhythmias, myocardial infarction, sudden cardiac death after myocardial infarction, heart failure, cerebral ischemia, sudden infant death syndrome (SIDS), impaired blood flow conditions, atrial fibrillation or sudden death in epilepsy. In one embodiment, the at least one branch of the trigeminal nerve is an ophthalmic nerve or an infraorbital nerve, wherein the body system is a trigeminal nerve cardiac reflex and wherein stimulation of the ophthalmic nerve or the infraorbital nerve modulates or activates the trigeminal nerve cardiac reflex to treat or prevent a cardiac related disorder. In one embodiment, the body system is a vagus nerve circuit, and wherein stimulation of the at least one branch of the trigeminal nerve modulates the vagus nerve circuit to treat a cardiac related disorder. In one embodiment, the medical disorder is fatigue, wherein the body system is a locus coeruleus or a reticular activating system, and wherein stimulation of the at least one branch of the trigeminal nerve modulates the locus coeruleus or modulates the reticular activating system to treat fatigue. In one embodiment, the medical disorder is selected from the group consisting of obesity and other disorders related to weight and feeding, inflammation, disorders of regulation of breathing, disorders of gastrointestinal function, autonomic regulation in menopausal hot flashes, regulation of hemostasis and sleep/insomnia, wherein the body system is a vagus nerve circuit, and wherein stimulation of the at least one branch of the trigeminal nerve modulates the vagus nerve circuit to treat said medical disorder. In one embodiment, the medical disorder is a dementing disorder wherein the body system is a vagus nerve circuit or a trigeminal nerve cardiac reflex, and wherein stimulation of the at least one branch of the trigeminal nerve modulates the vagus nerve circuit or the trigeminal nerve cardiac reflex to treat said medical disorder.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention is provided in the following written description of various embodiments of the invention, illustrated in the accompanying drawings, and defined in the appended claims.

BRIEF DESCRIPTION OF THE DRAWINGS

The present disclosure, both as to its organization and manner of operation, may be understood by reference to the following description, taken in connection with the accompanying drawings, in which:

FIGS. 1A and 1B illustrate the location of several branches (nerves) of the trigeminal nerve and the location of the major foramina for the superficial branches of the trigeminal nerve;

FIG. 1C is a diagram of the principal afferent and efferent projections of the nucleus of the solitary tract;

FIG. 3 shows average PET scanning data from a pair of adults being treated using aspects of the present disclosure and demonstrating brain regions with decreased regional blood flow;

FIG. 11 summarizes one embodiment of current, charge, current density and charge density parameters for a subject exposed to cutaneous stimulation of the supraorbital nerve;

FIGS. 14A-14B illustrates one embodiment of a protocol for mitigating potential accommodation.

DETAILED DESCRIPTION

Figure 1D:
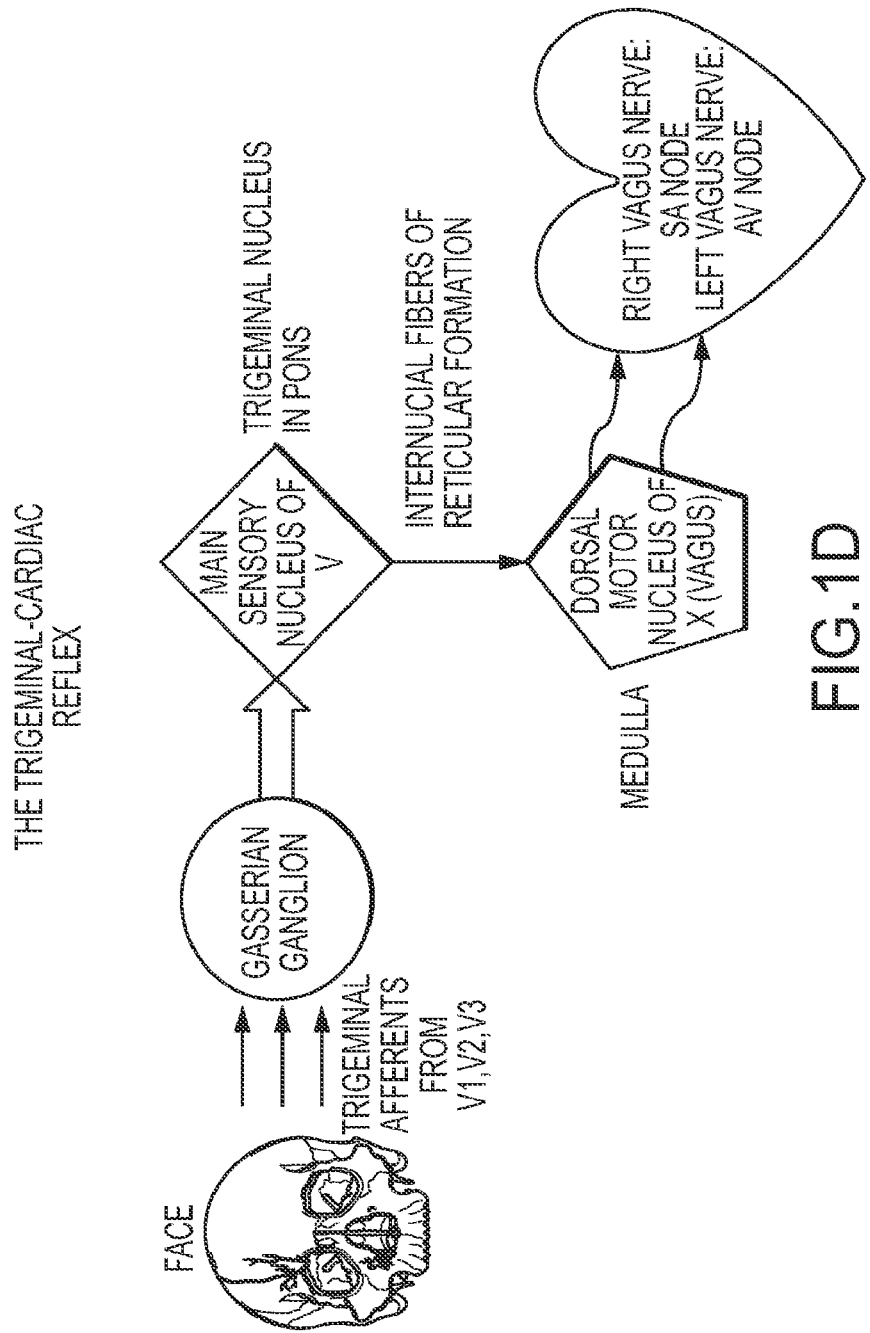
FIG. 1D illustrates the connection between the trigeminal nerve and the vagus nerve.

The present disclosure relates to methods, devices and systems used for the treatment of various medical disorders via stimulation of the superficial elements of the trigeminal nerve. The medical disorders may include, but are not limited to, neuropsychiatric disorders, neurological disorders, cardiac related disorders, fatigue, tinnitus, obesity, diabetes, dyslipidemia, metabolic syndrome, obstructive sleep apnea, arthritis, cachexia/anorexia, inflammation, asthma, inflammatory bowel disease, atopic dermatitis, sepsis, hepatitis, disorders of regulation of breathing, disorders of gastrointestinal function, gastroesophageal reflux, diarrhea and constipation, dysphagia and other disturbances of swallowing, gastroparesis, functional bowel syndromes, post-operative ileus, dyspepsia, motion sickness, chemotherapy-related nausea and emesis, autonomic regulation in menopausal hot flashes, regulation of hemostasis and sleep/insomnia. For example, aspects of the present disclosure may be used for the treatment of fatigue via stimulation of the superficial elements of the trigeminal nerve to modulate the locus coeruleus or modulate the reticular activating system. The present disclosure also relates to methods, devices and systems used for the treatment of various medical disorders via stimulation of the superficial elements of the trigeminal nerve to modulate the activity of the vagus nerve. More specifically, minimally invasive systems, devices and methods of stimulation of the superficial branches of the trigeminal nerve located extracranially in the face, namely the supraorbital, supratrochlear, infraorbital, auriculotemporal, zygomaticotemporal, zygomaticoorbital, zygomaticofacial, nasal and mentalis nerves (also referred to collectively as the superficial trigeminal nerve) are disclosed herein. Methods for the treatment various medical disorders, including neuropsychiatric disorders, neurological disorders, heart disease and other cardiac related disorders and fatigue, by sTNS (subcutaneous trigeminal nerve stimulation) and pTNS (percutaneous trigeminal nerve stimulation) are also provided. Systems and devices configured for therapeutic stimulation of the branches of the trigeminal nerves, such as the superficial trigeminal nerve, and their methods of application are also described.

As described in more detail herein, when the peripheral branches of the trigeminal nerve are carefully stimulated at frequencies of 1-300 Hz, at pulse durations of 50-500 usec, at output currents generally between 1 and 25 mA, or other parameters as disclosed elsewhere herein, our studies have shown selective activation or inhibition of brain structures involved in the control of the medical disorders disclosed herein. Thus, measured stimulation of branches of the trigeminal nerve at safe frequencies, pulse durations, and currents can be used to treat these medical disorders.

In addition, the unique anatomy of the trigeminal nerve, and its direct and indirect connections with key areas of the brainstem (including pons and medulla) and other structures of the nervous system involved with the vagus nerve may allow the use of subcutaneous or percutaneous stimulation of the trigeminal nerve as a method to modulate the vagus nerve to treat various medical disorders, including, but not limited to, obesity and other disorders related to weight and feeding, inflammation, disorders of regulation of breathing, disorders of gastrointestinal function, autonomic regulation in menopausal hot flashes, regulation of hemostasis and sleep/insomnia. Because the trigeminal nerve projects to the dorsal motor nucleus of the vagus nerve, trigeminal nerve stimulation can be used as a safe and non-invasive method to deliver stimulation of vagus nerve circuits in the brain, without implanting a vagus nerve stimulator, and without direct stimulation of the cervical vagus nerve or its branches. The methods, systems and devices described herein are minimally invasive.

The systems, devices and methods disclosed herein provide a less invasive form of neurostimulation to treat various medical disorders including, but not limited to, neuropsychiatric disorders, neurological disorders, cardiac related disorders, fatigue, obesity, diabetes, dyslipidemia, metabolic syndrome, obstructive sleep apnea, arthritis, cachexia/anorexia, inflammation, asthma, inflammatory bowel disease, atopic dermatitis, sepsis, hepatitis, disorders of regulation of breathing, disorders of gastrointestinal function, gastroesophageal reflux, diarrhea and constipation, dysphagia and other disturbances of swallowing, gastroparesis, functional bowel syndromes, post-operative ileus, dyspepsia, motion sickness, chemotherapy-related nausea and emesis, autonomic regulation in menopausal hot flashes, regulation of hemostasis and sleep/insomnia. More specifically, a subcutaneous or percutaneous (collectively, implantable) electrode assembly and a system comprising the same configured for trigeminal nerve stimulation are disclosed herein. As described in more detail herein, electrodes are not placed within the brain or near critical structures like the carotid artery or jugular vein. The electrodes are also not directly or physically attached or anchored to the nerve (e.g. by suturing), which requires intracranial invasion and may cause a spinal fluid leak, infection, nerve damage and/or severe pain. Instead, percutaneous or subcutaneous electrodes (or an electrode assembly) are placed (implanted) at or near a region of a patient's face or cranium that is in proximity to, adjacent to, in contact with, or distal to the trigeminal nerve (or the relevant branch(es) thereof) by attaching to subcutaneous or connective tissues above the periosteum or pericranium (a membrane that lines the outer surface of the skull) and below the epidermis (the outermost layer of skin). The nerve is stimulated at operational parameters within a predefined range and that may be further refined by factors such as patient history, disorder to be treated, or individual sensitivity to the stimulation. The electrode assembly placement as described herein does not require intracranial invasion (i.e. implantation below the skull) thereby reducing the risks of a spinal fluid leak and infection. In some embodiments, the electrode assembly may be placed or otherwise configured to stimulate the smaller branches of the trigeminal nerve. That is, the assembly is placed further away from the brain and the main branch of the nerve. Surprisingly, placement of the assembly further away from the brain and the main branch of the nerve is believed to be as efficacious as direct attachment to the main branch of the nerve and may provide increased safety for the patient.

Some brain stimulation methods aim to generate currents in large volumes of the cortex and treat the brain as a bulk conductor, for example, ECT (electroconvulsive therapy) at the whole-lobe level and rTMS (repetitive transcranial magnetic stimulation) at the large regional level (i.e. dorsolateral prefrontal cortex). Additionally, deep brain stimulation is generally predicated on stimulation of small but regional volumes that lead to discharges in a very large number of cells. The systems, devices and methods of the present disclosure send minimal, if any, current into the brain; instead, signals are sent into the brain in order to modulate the activity of relevant neuroanatomical structures. Without wishing to be bound by any particular theory, the electrical pulses generate signals in the cutaneous branches of the trigeminal nerve and the electric fields are generally confined to the skin tissue and there is minimal, if any, leakage into the brain. These electrical pulses traveling through the trigeminal pathways in the brain trigger a cascade of change in neuronal signaling events that involve very limited and precise recruitment of specific networks of neurons identified on figures attached that effect long lasting effects capable to modulate the diseases herein claimed. The neuroanatomic pathways allow targeted modulation of activity of the trigeminal nerve and the vagus nerve and further networks. Thus, the systems, devices and methods as disclosed herein utilize the brain's existing infrastructure to transmit signals to the targets of interest. In the context of this disclosure minimal current penetration means (1) a charge density of approximately 0 uC/cm2 at the cerebral cortex, or (2) calculated, measured, or modeled charge densities below the following thresholds at the cerebral cortex: at currents, charge densities, or charge per phase not likely to cause activation of pyramidal neurons and axons, and unlikely to cause brain injury. In some embodiments, a lower charge density may be used when the central nervous system of an individual patient is sufficiently sensitive to lower levels of stimulation that the lower level will still permit clinical benefit to accrue.

The following description is provided to enable any person skilled in the art to make and use the subject matter of this disclosure. Various modifications, however, will remain readily apparent to those skilled in the art, since the general principles of the disclosed subject matter have been defined herein specifically to describe: (1) methods of treating medical disorders by trigeminal nerve stimulation, (2) a system and an implantable electrode assembly configured for trigeminal nerve stimulation; and (3) methods of treating medical disorders using such system and electrode assembly.

To provide context for the disclosure, a brief description of the trigeminal nerve and its connection to the vagus nerve is now provided. With reference to FIGS. 1A and 1B, the trigeminal nerve is the largest cranial nerve, and has extensive connections with the brainstem and other brain structures. It is the fifth (of twelve) cranial nerves, and is often designated as Cranial Nerve V (CN V). The trigeminal nerve has three major sensory branches over the face, all of which are bilateral, and highly accessible. The supraorbital nerve, or ophthalmic nerve, is frequently referred to as the $V_1$ division. The infraorbital branch or maxillary nerve is commonly referred to as the $V_2$ division. The mentalis branch of the mandibular nerve is referred to as the $V_3$ division. The supraorbital nerve supplies sensory information about pain, temperature, and light touch to the skin of the forehead, the upper eyelid, the anterior part of the nose, and the eye. The infraorbital branch supplies sensory information about pain, temperature, and light touch sensation to the lower eyelid, cheek, and upper lip. The mentalis branch supplies similar sensory modalities to the skin of the lower face (e.g. jaw and tongue) and lips.

These branches exit the skull through three foramina, as shown in FIGS. 1A and 1B. The supraorbital nerve or ophthalmic nerve exits at foramen 1, approximately 2.1-2.6 cm from the nasal midline (in adults), and is located immediately above the orbital ridge that is located below the eyebrow. The infraorbital branch or maxillary nerve exits at foramen 2, approximately 2.4-3.0 cm from the nasal midline (in adults) and the mentalis nerve exits at foramen 3, approximately 2.0-2.3 cm from the nasal midline (in adults). Other sensory branches, including the zygomaticofacial, zygomaticoorbital, zygomaticotemporal, and auriculotemporal, arise from other foramina.

Fibers from the three major branches join together to form the trigeminal ganglion (also called the Gasserian ganglion). From there, fibers ascend into the brainstem at the level of the pons to synapse with the main sensory nucleus of the pons, the mesencephalic nucleus of V, and the spinal nucleus and tract of V. Pain fibers descend in the spinal nucleus and tract of V, and then ascend to the ventral posterior medial nucleus (VPM) of the thalamus, and then project to the cerebral cortex. Light touch sensory fibers are large myelinated fibers, which ascend to the ventral posterior lateral (VPL) nucleus of the thalamus, and also project to the cerebral cortex. Afferent sensory fibers project from the trigeminal nuclei to the thalamus and the cerebral cortex.

The trigeminal nucleus has reciprocal projections to the nucleus tractus solitarius or nucleus of the solitary tract (NTS), the locus coeruleus, the cerebral cortex and the vagus nerve. The NTS receives afferents from the vagus nerve and trigeminal nerve. As can be understood from FIG. 1C, the NTS integrates input from multiple sources, and projects to structures in the brainstem and forebrain, including the locus coeruleus. FIG. 1C, which is a modified reproduction from Ruffoli, R. et al, is a diagram of the principal afferent and efferent projections of the nucleus of the solitary tract. (see Ruffoli, R. et al., The chemical neuroanatomy of vagus nerve stimulation, J. Chem. Neuroanat. (2011), doi:10.1016/j.jchemneu.2010.12.002). The NTS connects to the medulla oblongata to control blood pressure and the respiratory center. The NTS projects to the dorsal motor nucleus of the vagus and the nucleus ambiguus parasympathetic pregangliar neurons and influences cardiac activity. The NTS connection to the nucleus ambiguus results in innervation the striate muscles involved in swallowing and heart rate. The NTS also projects to the periaqueductal grey and visceral nuclei of the spinal cord, mediating visceral sensation. Efferent pathways reach the BNTS, from which they are relayed to the amygdala. Inputs from NTS reach the cerebral cortex via the parabrachial complex and the VPM. (see generally, Ruffoli et al. 2011). Additionally it also has connections to other nuclei in the brain, for example the dorsal cochlear nucleus which affects tinnitus. (Soleymani et al Surgical approaches to tinnitus treatment: A review and novel approaches, Surg Neurol Int 2011, 2:154.)

The locus coeruleus is a paired nuclear structure in the dorsal pons, and is located just beneath the floor of the fourth ventricle. The locus coeruleus has extensive axonal projections to a broad number of brainstem, sub-cortical and cortical structures, and is an important part of the reticular activating system. The locus coeruleus is a core part of the brainstem noradrenergic pathway, and produces the neurotransmitter norepinephrine. Norepinephrine plays a key role in attention, alertness, blood pressure and heart rate regulation, anxiety, and mood.

Turning now to FIG. 1D, and with continued reference to FIG. 1C, the trigeminal nerve is connected to the vagus nerve. Afferent sensory fibers from the three trigeminal divisions ($V_1$, $V_2$, $V_3$) project to the Gasserian ganglion, synapse there, and then project to the main sensory nucleus of the trigeminal nerve. Axons from the sensory nucleus then project via the Internucial fibers of the Reticular Formation to the Dorsal Motor Nucleus of the vagus nerve (the tenth cranial nerve, also designated as Cranial Nerve X or CN X) in the dorsal medulla. Efferent fibers from each right and left vagus nerve nuclei then form the main trunk of the vagus nerve. Thus, because of the underlying anatomy, and projections from the trigeminal nerve nuclei to the vagus nerve nuclei, stimulation of the peripheral branches of the trigeminal nerve can be utilized to activate the vagus nerve. This results in vagus nerve stimulation from peripheral trigeminal nerve stimulation. Since trigeminal nerve activation of the vagus nerve can be performed in a minimally invasive fashion, activating the vagus nerve via activation of the peripheral branches of the trigeminal nerve has advantages over direct vagus nerve stimulation, which is currently performed using a surgically implantable electrode and pulse generator attached to the vagus nerve. This engagement of the vagus nerve via trigeminal nerve stimulation has direct clinical application to treating medical disorders as disclosed herein, which may benefit from increased vagus nerve or parasympathetic activity. Without wishing to be bound by any particular theory, the systems and methods disclosed herein for stimulation of the trigeminal nerve to activate the vagus nerve may also be relevant for neurological, psychiatric, cardiac or other medical disorders where vagus nerve stimulation is activated or provided via stimulation of the trigeminal nerve and its branches. Thus, trigeminal nerve stimulation is a potential method to initiate, activate and provide stimulation to vagus nerve circuits.

In one aspect, the disclosure describes the application of trigeminal nerve stimulation to treat medical disorders including: neuropsychiatric and neurological disorders, cardiac related disorders, fatigue, tinnitus and other medical disorders. Stimulation of peripheral and cutaneous branches of the trigeminal nerve in the face, ear or scalp can be applied and stimulated at safe frequencies, pulse durations and amplitudes. Such treatment and prevention is advantageous over the currently used pharmacological approaches which often have undesirable side effects or lack specificity in their actions.

In another aspect, the disclosure describes the application of trigeminal nerve stimulation as a method to stimulate the vagus nerve to treat medical disorders including: neuropsychiatric and neurological disorders, cardiac related disorders, fatigue, tinnitus, obesity and other disorders related to weight and feeding, inflammation, disorders of regulation of breathing, disorders of gastrointestinal function, autonomic regulation in menopausal hot flashes, regulation of hemostasis and sleep/insomnia and disturbances of sleep. Since the trigeminal nerve projects to the dorsal motor nucleus of the vagus nerve, trigeminal nerve stimulation can be used as a safe and minimally invasive method to deliver stimulation to vagus nerve circuits, without implanting a vagus nerve stimulator, and without direct stimulation of the cervical vagus nerve or its branches.

Psychiatric and Neuropsychiatric Disorders

The unique anatomy of the trigeminal nerve, and its direct and indirect connections with key areas of the brainstem, thalamus, amygdala, insula, anterior cingulate and other cortical and subcortical areas involved with sensory processing, attention, emotion, cognition, and autonomic function, may allow the use of external stimulation for a variety of neuropsychiatric conditions in which stimulation may be desirable.

The present disclosure relates to methods, devices and systems used for the treatment of mood, anxiety, post traumatic stress disorder, neuropsychiatric disorders, including mood (such as depression), anxiety (such as post-traumatic stress disorder) and psychotic disorders (e.g. schizophrenia), and cognitive and behavioral disorders as well as well as attention deficit disorder (ADD), attention deficit hyperactivity disorder (ADHD), autism and autism spectrum disorders (ASD), substance use disorders and related behavioral addictions, eating disorders, psychotic disorders and obsessive compulsive disorder (OCD) (collectively, neuropsychiatric disorders) via stimulation of the superficial elements of the trigeminal nerve ("TNS"). More specifically, subcutaneous and percutaneous methods of stimulation of the superficial branches of the trigeminal nerve located extracranially in the face, namely the supraorbital, supratrochlear, infraorbital, auriculotemporal, zygomaticotemporal, zygomaticoorbital, zygomaticofacial, infratrochlear, nasal and mentalis nerves (also referred to collectively as the superficial trigeminal nerve) are disclosed herein. Methods for the treatment of mood and other neuropsychiatric disorders including but not limited to attention deficit disorder (ADD), attention deficit hyperactivity disorder (ADHD), autism and autism spectrum disorders (ASD), substance use disorders and related behavioral addictions, eating disorders and obsessive compulsive disorder (OCD) by sTNS (subcutaneous trigeminal nerve stimulation) and pTNS (percutaneous trigeminal nerve stimulation) are also provided. Systems and devices configured for therapeutic stimulation of the trigeminal nerve or branches thereof, such as the superficial trigeminal nerve, and their methods of application are also described.

While not wishing to be bound by any particular theory, in certain embodiments, the connections between the trigeminal nerve and the locus coeruleus, thalamus, amygdala, anterior cingulate, and other central nervous system structures as described above may be relevant to a potential role of the trigeminal nerve in neuropsychiatric disorders, including mood (such as depression), anxiety (such as post-traumatic stress disorder), psychosis (such as schizophrenia) and other cognitive and behavioral disorders. Thus, subcutaneous and/or percutaneous stimulation of the trigeminal nerve can be effective in the treatment of these neuropsychiatric disorders.

Figure 2:
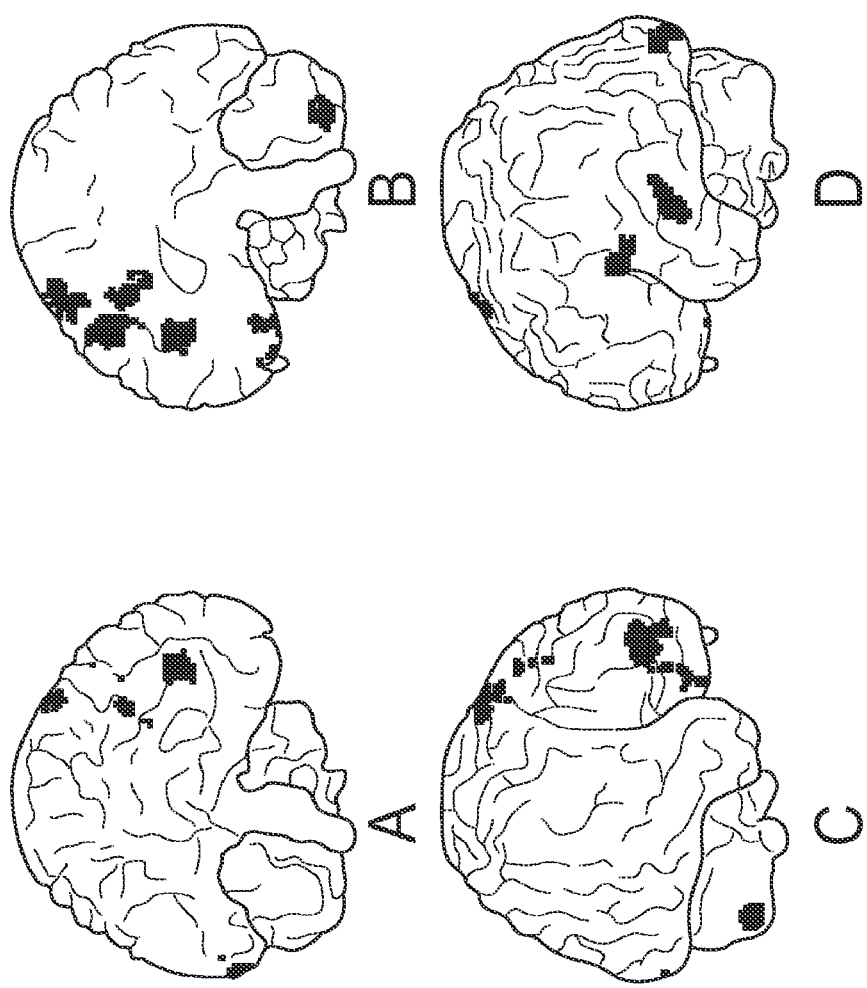
FIG. 2 shows average Positron Emission Tomography (PET) scanning data from a pair of adults being treated using aspects of the present disclosure and demonstrating brain regions with increased regional blood flow.

The PET scan data of FIGS. 2 and 3 support the use of TNS in humans for treatment of neuropsychiatric disorders, namely depression and anxiety disorders, such as PTSD. As discussed in more detail below, the PET scans show sections of the brain with increased activity (FIG. 3) and decreased activity (FIG. 3). For example, increased activity is seen in the medial prefrontal cortex, including the ACC, (see FIG. 2, which is indicated by the color (darker) pixels in panels (a) and (b)). Increased activity of the dorsolateral prefrontal cortex is also shown in FIG. 2, panel c as the large colored (darker) area in the lower right of the image. Increased activity is also seen in the orbitofrontal cortex, as shown in FIG. 2 in panel b as the small region at the lower left of the image. Modulation of the activity in these and other brain structures, which are shown to be affected by trigeminal nerve stimulation, assist in improving the symptoms of depression and anxiety disorders, such as PTSD, and other medical disorders disclosed elsewhere herein.

Other medical disorders may also be treated according to aspects of the present disclosure, as indicated by PET scan data (see FIGS. 2 and 3) obtained from two adults that were treated according to aspects of the present disclosure. FIG. 2 shows an increased activity in the medial prefrontal cortex, including the ACC, which is indicated by the color (darker) pixels in panels (a) and (b). Increased activity in the superior frontal gyrus is seen in panels (c) and (d), on the upper (superior) surface of the brain, while the increased activity in the lateral frontal cortex is seen most clearly in panel (c), in the lower-right part of that image. FIG. 3 shows a decreased activity in the superior parietal cortex which is seen in panel (a) as the colored (darker) region in the upper left of that image, panel (b) as the colored (darker) pixels in the upper right, panel (c) as the upper two regions of color (darker) pixels, and in panel (d) as the colored (darker) region near the top of the brain. The decreased activity in the cortex is consistent with the antiepileptic effects of TNS. The temporal-occipital cortex is seen in panel (c) as the largest colored (darker) region, and in panel (d) as the middle of the three colored areas. Modulation of the activity in these and other brain structures, which are shown to be affected by trigeminal nerve stimulation, assist in improving the symptoms of attention deficit disorder (ADD), attention deficit hyperactivity disorder (ADHD), autism and autism spectrum disorders (ASD), substance use disorders and related behavioral addictions, eating disorders, psychotic disorders and obsessive compulsive disorder (OCD).

Attention Deficit Disorder (ADD), Attention Deficit Hyperactivity Disorder (ADHD), Autism, and Autism Spectrum Disorders (ASD)

Without wishing to be bound by any particular theory, neuroimaging studies have implicated dysfunction in several brain regions in the pathophysiology and treatment response of these disorders, which commonly arise early in life. As defined by the American Psychiatric Association's Diagnostic and Statistical Manual of Mental Disorders (American Psychiatric Association, 4th edition, 2000), attention deficit/hyperactivity disorder (ADHD) is marked by symptoms of inattention, hyperactivity, and impulsivity, while the diagnosis of ADD (now formally ADHD/inattentive type) lacks the hyperactivity and impulsivity features. In ADD and ADHD, prior research has found abnormalities in multiple regions, including the anterior cingulate cortex (ACC) and parietal cortex (e.g., Makris et al., 2010, *J Atten Disord* 13(4):407-13; Dickstein S G, et al. 2006 *J Child Psychol Psychiatry.* 47(10):1051-62). As defined by the American Psychiatric Association's Diagnostic and Statistical Manual of Mental Disorders (American Psychiatric Association, 4th edition, 2000), autism (also termed autistic disorder) is characterized by pervasive deficits in development in areas such as reciprocal social interaction skills, communication skills, or the presence of stereotyped behavior, interests, and activities. ASD includes related diagnoses such as Asperger's Syndrome, in which most features are present but not a delay in language development. Regions implicated in Autism and ASD include ACC, frontal cortex, temporal cortex, and parietal cortex (e.g., Hall G B, Szechtman H, Nahmias C. 2003. *Am J Psychiatry.* 160(8):1439-41; McAlonan G M, et al. 2005. *Brain.* 128(Pt 2):268-76; Cherkasova M V, Hechtman L. 2009. *Can J Psychiatry.* 54(10):651-64; Konrad K, et al. 2006. *Biol Psychiatry.* 59(7):643-51.)

Regional activation with trigeminal nerve stimulation was examined using Positron Emission Tomographic (PET) scanning in two adults. FIG. 2 shows areas of increased blood flow emerging after acute exposure to TNS; regions of statistically significant differences between epochs of exposure and non-exposure are indicated. Areas that exhibited significant increases in regional activation with TNS included the medial prefrontal cortex (including ACC), the superior frontal gyms, the lateral frontal cortex, and the middle temporal gyrus. FIG. 3 shows areas of decreased blood flow under the same conditions; significant regional inhibition was found in the superior parietal cortex temporal-occipital cortex. Modulation of the activity in these and other brain structures, which are shown to be affected by trigeminal nerve stimulation, could assist in improving the cognitive and behavioral symptoms of ADD, ADHD, Autism, and ASD.

Substance Use Disorders and Related Behavioral Addictions.

Disorders of substance abuse and dependence (e.g., of alcohol, cocaine, marijuana, tobacco, etc.) are defined as disorders of maladaptive patterns of behavior, as defined by the American Psychiatric Association's Diagnostic and Statistical Manual of Mental Disorders (American Psychiatric Association, 4th edition, 2000), and include criteria such as tolerance to a substance, withdrawal upon discontinuing use, an inability to cut down or control use of the substance, and giving up important social, occupational, or recreational activities because of using the substance. Behavioral addictions (e.g., internet addiction, sexual addiction, pathological gambling) share clinical features similar to those maladaptive patterns of behavior which are centered on chemical substances, but with engagement in the problem behavior rather than consuming a substance. Without wishing to be bound by any particular theory, neuroimaging studies have implicated dysfunction in several brain regions in the pathophysiology and treatment response in these disorders, particularly the anterior cingulate cortex (ACC), frontal cortex, and parietal cortex (Goldstein R Z and Volkow N D. 2011. *Neuropsychopharmacology.* 36(1):366-7; Vollstädt-Klein S, et al., 2010. *Alcohol Clin Exp Res.* 34(5):771-6; Fineberg N A, et al., 2010. *Neuropsychopharmacology.* 35(3):591-604; Dannon P N, et al. 2011. *Brain Imaging Behav.* 5(1):45-51, published online Nov. 16, 2010.). As noted above, PET scan data showed acute alterations in regional brain activity with exposure to TNS; these areas include those regions implicated in substance use disorders and in behavioral addictions. Modulation of activity in these and other brain structures, which are shown to be affected by trigeminal nerve stimulation, could assist in improving the cognitive and behavioral symptoms of substance use and behavioral addiction disorders.

Eating Disorders

Eating disorders include illnesses such as anorexia nervosa, bulimia nervosa, and other disorders related to eating (e.g., binge eating), as defined by the American Psychiatric Association's Diagnostic and Statistical Manual of Mental Disorders (American Psychiatric Association, 4th edition, 2000); in all, problems center disorders of eating behaviors, predominantly related to perceived body image, consumption of food, and/or expenditure of energy (e.g. excessive exercise); these behaviors can lead to abnormal weight and potentially life-threatening states of malnutrition or metabolic abnormalities. Without wishing to be bound by any particular theory, neuroimaging studies have implicated several brain regions in these disorders, including ACC and prefrontal cortex, and abnormal afferent inputs to the brain via the vagus nerve (Joos A, et al., 2010 *Psychiatry Res.* 182(2):146-51; Miyake et al., 2010. *Psychiatry Res.* 181(3): 183-92; Faris P L, et al., 2006 *J Affect Disord* 92(1):79-90.) As noted above, PET scan data showed acute alterations in regional brain activity with exposure to TNS; these areas include those regions implicated in eating disorders. Modulation of activity in these and other brain structures, which are shown to be affected by trigeminal nerve stimulation, could assist in improving the symptoms of eating disorders.

Obsessive Compulsive Disorder.

Obsessive Compulsive Disorder (OCD), as defined by the American Psychiatric Association's Diagnostic and Statistical Manual of Mental Disorders (American Psychiatric Association, 4th edition, 2000), is marked by the presence of obsessive, ruminative thoughts (e.g. fears of contamination with dirt or germs), and compulsive behaviors (e.g., ritualized handwashing). Without wishing to be bound by any particular theory, neuroimaging studies have implicated several brain regions in these disorders, including ACC, caudate nucleus, striatum, prefrontal cortex, and parietal cortex (e.g., Huyser C, et al., 2010. *J Am Acad Child Adolesc Psychiatry.* 49(12):1238-48; Matsumoto R, et al., 2010. *Psychiatry Clin Neurosci.* 64(5):541-7). As noted above, PET scan data showed acute alterations in regional brain activity with exposure to TNS; these areas include some of those regions implicated in OCD. Modulation of activity in these and other brain structures, which are shown to be affected by trigeminal nerve stimulation, could assist in improving the symptoms of OCD Surprisingly, our data show that TNS affects heart rate and cardiac function, physiologic measures under vagal control. (Pop et al, Epilepsy & Behavior 2011 and FIG. 13). Trigeminal nerve stimulation thus provides minimally invasive modulation of, and access to, the autonomic nervous system, including the parasympathetic pathways of the vagus system. While not wishing to be bound by any particular theory, some clinical effects of TNS may be mediated by trigeminal modulation of the vagus nerve system, while other clinical effects of TNS are independent of vagal circuit modulation, and yet others may reflect a combination of direct trigeminal effects and indirect effects mediated by the vagus nerve system. For example, with regard to the antiepileptic effects of TNS, our human PET data show decreased activity in cortical areas related to seizure initiation, propagation and inhibition, which are independent of known vagal inputs. (FIGS. 2 and 3) There is also data from pre-clinical animal models showing that TNS inhibits neocortical neuronal firing via a direct mechanism independent of vagal synapses as evidenced by the rapid onset of the effect. (Fanselow et al, Abstract 2.220, Annual Meeting of the American Epilepsy Society, San Antonio, Tex. 2010) Surprisingly, the clinical response to TNS can arise directly from trigeminal effects independent of the vagus nerve or mediated through, and in combination with, the vagus nerve and its circuits. In addition, since the trigeminal nerve projects to the dorsal motor nucleus of the vagus nerve, trigeminal nerve stimulation can be used as a safe and non-invasive method to deliver stimulation to vagus nerve circuits, without implanting a vagus nerve stimulator, and without direct stimulation of the cervical vagus nerve or its branches. Stimulation of the vagus nerve circuits via trigeminal nerve reduces seizure activity. As described elsewhere herein, our data demonstrates a 4% reduction in heart rate via acute stimulation of the trigeminal nerve (e.g. modulation of the vagus nerve via trigeminal nerve stimulation activates the trigeminal-cardiac reflex.) In addition, since the trigeminal nerve projects to the dorsal motor nucleus of the vagus nerve, trigeminal nerve stimulation can be used as a safe and minimally invasive method to deliver vagus nerve stimulation, without implanting a vagus nerve stimulator, and without direct stimulation of the cervical vagus nerve or its branches.

Psychotic Disorders Including Schizophrenia

Without wishing to be bound by any particular theory, the cause(s) of psychotic illnesses, such as schizophrenia, remain to be fully understood, but findings from neuroimaging studies implicate specific brain regions in the development of symptoms, such as hallucinations, delusions, impaired reality testing, and disorganized thought processes. Areas such as the temporo-parietal cortex, bilateral prefrontal cortical regions, and the anterior cingulate cortex have been linked to psychosis (e.g., Fusar-Poli P, et al. Neuroanatomy of vulnerability to psychosis: a voxel-based meta-analysis. Neurosci Biobehav Rev. 2011. 35(5):1175-85). Data from our PET scan study (above) showed acute alterations in regional brain activity with exposure to TNS; these areas include those regions implicated in schizophrenia and other psychotic disorders. Modulation of activity in these and other brain structures, which are shown to be affected by trigeminal nerve stimulation, could assist in improving the symptoms of schizophrenia and other psychotic disorders and can be treated according to the systems, devices and methods disclosed herein.

Dementing Disorders Including Alzheimer's Disease

Dementing disorders are marked by cognitive impairments, particularly problems with memory and behavior, and include specific illnesses such as Alzheimer's Disease, Vacular Dementia, and Fronto-temporal Dementia. Multiple cortical and subcortical structures may be disrupted in these disorders. Activity in many of these structures may be modulated by inputs from the locus coeruleus (e.g., Samuels E R, Szabadi E. Functional neuroanatomy of the noradrenergic locus coeruleus: its roles in the regulation of arousal and autonomic function part II: physiological and pharmacological manipulations and pathological alterations of locus coeruleus activity in humans. *Curr Neuropharmacol.* 2008 September; 6(3):254-85). Without wishing to be bound by any particular theory, the circuitry of the trigeminal nerve system is able to send signals to the locus coeruleus, so that TNS-driven modulation of the locus coeruleus impacts these disorders. In addition, stimulation of the vagus nerve has been used to treat symptoms of Alzheimer's disease (e.g., Merrill C A, et al. Vagus nerve stimulation in patients with Alzheimer's disease: Additional follow-up results of a pilot study through 1 year. *J Clin Psychiatry.* 2006. 67(8):1171-8). Modulation of activity in these and other brain structures can be used to treat the medical disorders as disclosed herein according to the systems, devices and methods disclosed herein.

Heart Disease and Other Cardiac Related Disorders

The trigeminal-cardiac reflex or trigemino-cardiac reflex (TCR) is a central nervous system reflex which functions to increase cerebral blood flow and provide neuroprotection when the brain is exposed to hypoxia or diminished blood flow. An exaggerated form of this reflex can occur during neurosurgical, eye, or sinus procedures as the result of traction or manipulation of branches of the trigeminal nerve. Under these conditions, significant reductions in heart rate, heart block, or complete asystole have been reported. (See generally, Schaller et al., J Neurosurgical Anesthesiology, 2009; 21:187-95)

In the past, the TCR had been used to clinical benefit to reduce the heart rate in the setting of life threatening or severe arrhythmias. For example, physicians have utilized the TCR to slow the heart rate through application of ocular pressure during supraventricular tachycardia. This primitive, poorly-controlled technique could be associated with adverse events such as excessive reductions in heart rate, and with the advent of improved drug therapy for arrhythmias, this technique is no longer in common use.

Reflex bradycardia, hypotension and occasionally asystole as a result of the TCR have been reported for many years as a complication encountered during ophthalmologic and neurosurgical procedures. These adverse events arise from stimulation of the TCR in an uncontrolled and nonspecific fashion. Through stimulation of the peripheral branches of the trigeminal nerve, employing particular frequencies, pulse durations and current outputs, the TCR can be activated (or utilized) in a controlled fashion to provide therapeutic ends including protection of the brain and the heart, as well as modulation of the activity of these organs.

The unique anatomy of the trigeminal nerve, and its direct and indirect connections with key areas of the brainstem (including pons and medulla) and other structures of the nervous system involved with the vagus nerve and/or the TCR allow the use of subcutaneous and/or percutaneous stimulation of the TNS as a method to activate the TCR to prevent and/or treat cardiac related disorders, including, but not limited to, preventing and/or treating cardiac arrhythmias, arrhythmias and sudden cardiac death after myocardial infarction, heart failure, SIDS, cerebral ischemia, impaired blood flow conditions, atrial fibrillation and reducing the risk of sudden death in epilepsy. In addition, since the trigeminal nerve projects to the dorsal motor nucleus of the vagus nerve, trigeminal nerve stimulation can be used as a safe and minimally invasive method to deliver vagus nerve stimulation, without implanting a vagus nerve stimulator, and without direct stimulation of the cervical vagus nerve or its branches.

Turning back to FIG. 1D, and with reference to FIG. 1C, the TCR is the result of connections between divisions of the trigeminal nerve, the internuncial fibers of the reticular formation and the vagus nerve nuclei, including the motor nucleus of the vagus nerve. Projections from the vagus nerve innervate the heart. Stimulation of this pathway and reflex arc can cause selective reduction in heart rate. Afferent sensory fibers from the three trigeminal divisions ($V_1$, $V_2$, $V_3$) project to the Gasserian ganglion, synapse there, and then project to the main sensory nucleus of the trigeminal nerve. Axons from the sensory nucleus then project via the Internucial fibers of the Reticular Formation to the Dorsal Motor Nucleus of the vagus nerve (Cranial Nerve X) in the dorsal medulla. Efferent fibers from each right and left vagus nerve nuclei then form the main trunk of the vagus nerve. Branches from the cervical portion of the vagus nerve then form the left and right cardiac nerves (both superior and inferior branches). These branches innervate the heart: the left vagus nerve projects primarily to the Atrioventricular Node (AV node), and the right vagus nerve projects to the Sinoatrial Node (SA node). Via these branches, the vagus nerve acts to reduce the heart rate, modify conduction, and stabilize the myocardium in response to stress and ischemia. The TCR reflex is protective. It lowers heart rate in the presence of ischemia by protecting the heart from fast cardiac arrhythmias (tachyarrhythmias), and by increasing cerebral blood flow in the setting of hypoxia. Without wishing to be bound by any particular theory, stimulation of the trigeminal nerve, particularly via the ophthalmic, supraorbital, supratrochlear or infraorbital branches, can be performed safely to modulate the TCR and prevent and/or treat heart disease and related cardiac disorders. Proper, controlled activation of this reflex arc, using a range of parameters, through cutaneous trigeminal nerve stimulation, can be used to protect the heart by reducing heart rate, reducing heart rate variability, and preventing or treating tachyarrhythmias and preventing sudden cardiac death. When properly applied, utilization of this reflex arc through trigeminal nerve stimulation can also protect the brain by conserving oxygen and reducing the adverse effects of ischemia and seizures. Conditions benefiting by measured activation of the TCR include heart failure, SIDS, supraventricular and ventricular tachycardia, acute myocardial infarction, impaired blood flow conditions, atrial fibrillation prevention of sudden cardiac death and sudden death in epilepsy, and neuroprotection.

As a result, because of the anatomy underlying the TCR, and projections from the trigeminal nerve nuclei to the vagus nerve nuclei, stimulation of the peripheral branches of the trigeminal nerve can be utilized to activate the vagus nerve. This results in vagus nerve stimulation from peripheral trigeminal nerve stimulation. Since trigeminal nerve activation of the vagus nerve can be performed in minimally invasive fashion, activating the vagus nerve via activation of the peripheral branches of the trigeminal nerve has surprising advantages over direct vagus nerve stimulation, which is currently performed using a surgically implantable electrode and pulse generator attached to the vagus nerve. This engagement of the vagus nerve via trigeminal nerve stimulation has direct clinical application to preventing and/or treating and/or preventing cardiac related disorders (and other disorders as disclosed herein), which may benefit from increased vagus nerve or parasympathetic activity. Without wishing to be bound by any particular theory, the system disclosed herein for stimulation of the trigeminal nerve to activate the TCR may also be relevant for other neurological, psychiatric, cardiac or other disorders where vagus nerve stimulation is activated or provided via stimulation of the trigeminal nerve and its branches. Since the TCR reflects vagus nerve activation via stimulation of the trigeminal nerve, trigeminal nerve stimulation is a potential method to initiate, activate and provide vagus nerve stimulation.

Stimulation of peripheral and cutaneous branches of the trigeminal nerve in the face, ear or scalp and the vagus nerves can be applied and stimulated at safe frequencies, pulse durations and amplitudes. An external device can be applied in, for example, the ambulance, emergency room, intensive care unit or other setting, to activate the TCR (or the allied oculo-cardiac reflex in the setting of ophthalmic nerve stimulation). Controlled stimulation may activate the TCR to safely reduce heart rate and heart rate variability in acute myocardial infarction and heart failure, prevent and/or treat cardiac arrhythmias, protect the heart and brain from injury and ischemia, and reduce the risk of sudden death from heart disease, SIDS and epilepsy, help stabilize cardiac rhythm and prevent sudden cardiac death and treatment of impaired blood flow conditions and atrial fibrillation. Such treatment may be used to reduce mortality in heart disease. Such treatment and prevention is advantageous over the currently used pharmacological approaches which often have undesirable side effects or lack specificity in their actions. The ability to peripherally and bilaterally stimulate the vagal nerve circuits through the trigeminal pathways connection in the brainstem provides possibility of strong effects, not obtained with unilateral stimulation of the vagal nerve.

In one aspect, the disclosure describes the application of trigeminal nerve stimulation as a method to activate the trigeminal cardiac reflex (TCR) to prevent and treat cardiac arrhythmias; prevent arrhythmias and sudden cardiac death after myocardial infarction; treat heart failure; treat cerebral ischemia; treat impaired blood flow conditions and atrial fibrillation; and reduce the risk of sudden death in epilepsy and SIDS. In addition, since the trigeminal nerve projects to the dorsal motor nucleus of the vagus nerve, trigeminal nerve stimulation can be used as a safe and minimally invasive method to deliver stimulation of vagus nerve circuits, without implanting a vagus nerve stimulator, and without direct stimulation of the cervical vagus nerve or its branches.

Heart Failure

Heart Failure is characterized by an increase in heart rate in response to diminished ventricular function. The increased heart rate results in increased energy demands upon an injured and dysfunctional myocardium. Further, there is abnormal parasympathetic control of the heart, as measured by a depressed baro-receptor reflex, which can lead to arrhythmias, and is associated with increased mortality. (De Ferrari et al. 2010 Schwartz et al., Heart Rhythm 2009; 6:S76-S81). Vagus nerve stimulation, using implantable electrodes attached to the cervical portion of the vagus nerve, reduces heart rate and improves left ventricular function in animals and humans. (Schwartz et al. 2009; Annegers et al., Epilepsia 2000; 41:549-53). In a rat model of chronic heart failure, vagus nerve stimulation was evaluated to determine its effects on heart rate and outcome. (Annegers et al., 2000) Using this model, a 10-15% reduction in heart rate was associated with significant improvement in survival from heart failure. (Annegers et al., 2000) Rats that underwent vagus nerve stimulation had a mortality of only 14%, versus 50% mortality among untreated rats: a 73% relative reduction in death rate. (Annegers et al., 2000) Pilot human studies of vagus nerve stimulation for heart failure are promising; preliminary data from a multi-center study of vagus nerve stimulation shows improved cardiac function (as measured by left ventricular systolic volumes and ejection fractions) when the heart rate was reduced by 5-10 beats per minute by vagus nerve stimulation. (De Ferrari et al. 2010, Schwartz et al., 2009).

Myocardial Infarction and Sudden Cardiac Death

Vagus nerve activity, as measured by baroreflex sensitivity, is significantly reduced and impaired after myocardial infarction. (Schwartz et al., 2009) As a result, there is reduced protection against severe life threatening arrhythmias and an increased risk of sudden death. Immediately after myocardial infarction, there is a surge in sympathetic activity, resulting in an increased heart rate, and increased stress on the myocardium. (Schwartz et al., 2009) Unopposed sympathetic activity can result in worsening of the infarction, and the propensity for lethal arrhythmias. In a dog model of cardiac ischemia and sudden death, implanted vagus nerve stimulation significantly reduced the risk of lethal arrhythmias (e.g. ventricular fibrillation). (Schwartz et al., 2009) Dogs treated with vagus nerve stimulation after the induction of myocardial ischemia experienced ventricular fibrillation in only 12%, versus 92% in dogs who did not undergo vagus nerve stimulation.

In the setting of acute myocardial infarction, trigeminal nerve stimulation represents a novel method of increasing vagus nerve activity, reducing heart rate, and counteracting the undesired effects of sympathetic activity on the heart. Paramedics, emergency room, and intensive care staff can apply trigeminal nerve stimulation using external electrodes, reducing the heart rate via controlled engagement of the trigeminal-cardiac reflex, and protect the heart from excessive sympathetic activity. This may improve outcome after myocardial infarction and reduce the risk of sudden cardiac death and lethal arrhythmias. (Schwartz et al., 2009).

Sudden Death in Epilepsy

Sudden unexpected death in epilepsy (SUDEP) is a major cause of death in people with epilepsy, accounting for 20-30% of the mortality associated with epilepsy. Sudden Unexpected Death in Epilepsy is generally defined as: "sudden, unexpected, witnessed, or unwitnessed, non-traumatic, and non-drowning death in an individual with epilepsy, with or without evidence of a seizure . . . in which the postmortem examination does not reveal a cause for death." (Li M et al., Circulation 2004; 109:120-124) The mechanisms of SUDEP are not completely understood, but two causes have been proposed: asphyxia/hypoxia and lethal arrhythmias related to deranged vagus-mediated autonomic control of the heart. There is evidence that vagus nerve stimulation may lower the risk of SUDEP after two years of stimulation, a finding requiring further investigation. (Li M et al., 2004) However, since current commercial forms of vagus nerve stimulation require surgical implantation to stimulate the cervical trunk of the vagus nerve in the neck, trigeminal nerve stimulation represents a novel and less invasive method to improve parasympathetic autonomic function, reduce heart rate variability and protect the brain and heart. Therefore, trigeminal nerve stimulation can be utilized to improve the degree of vagus nerve-mediated autonomic control of the heart, and help to prevent sudden death in epilepsy. Further, since the TCR is a cerebral protective reflex, which protects the brain during hypoxia, utilizing it in patients at risk for sudden death in epilepsy may protect brain and heart function during and after seizures, when hypoxia may commonly occur.

Atrial Fibrillation

Some related cardiac related conditions are characterized by an onset event which, if left unrecognized and untreated, could lead to serious injury, such as the onset of atrial fibrillation, a cardiac rhythm disturbance that is a recognized risk factor for ischemic stroke. In one embodiment of the system, individuals who are at risk for developing atrial fibrillation could be instructed to self-apply and activate the TNS system to engage the TCR. In another embodiment, and as described in more detail below with respect to a closed loop device, a sensing element may detect a change in the condition of a patient (e.g., an electrocardiographic monitor would detect the onset of a potentially-dangerous heart rhythm) and automatically initiate trigeminal nerve stimulation.

Impaired Blood Flow Conditions

Because of the neuroprotective effects of the TCR, the use of trigeminal nerve stimulation may also include conditions in which impairment of blood flow to the brain may cause and/or worsen the progression of these conditions (collectively, "impaired blood flow conditions"). For example, many forms of dementia (e.g., Alzheimer's Disease, Vascular Dementia, Frontotemporal Dementia) are associated with impairments in blood flow to the brain, and interventions which may enhance delivery of blood to the brain may be clinically useful. Similarly, other conditions of the brain, such as multiple sclerosis, Pick's disease, the transient hypoxia produced by sleep apnea, or infectious disease of the brain (e.g. Lyme Disease, HIV/AIDS) may also have a course which may be worsened by impairments in blood flow and may be improved through the neuroprotective actions of the TCR, and therefore could benefit from TNS.

Other Medical Conditions and Disorders

Stimulation of a specific cranial nerve, the trigeminal nerve, has been found to reduce symptoms of fatigue in patients with major depressive disorder or with epilepsy. Stimulation of the trigeminal nerve to modulate activity of the vagus nerve has also been found to treat other medical disorders. This non-pharmacological treatment for fatigue and other medical disorders may reduce the disability experienced by individuals with fatigue or other medical disorders, by addressing impairments from the medical condition while reducing or minimizing the side effects (including interaction with other medications and risk of addiction) posed by psychostimulants or other medications conventionally used to treat these conditions.

The unique anatomy of the trigeminal nerve, and its direct and indirect connections with key areas of the brainstem (including pons and medulla) and other structures of the nervous system involved with the vagus nerve may allow the use of cutaneous stimulation of the TNS as a method to modulate the vagus nerve or vagus nerve circuits to, surprisingly, treat various medical disorders, including, but not limited to, neurological disorders such as epilepsy, seizure related disorders, acute brain injury, chronic brain injury, chronic daily headache, migraine, disorders related to migraine and headache and movement disorders, and neuropsychiatric disorders, such as depression, mood disorders, cognitive disorders, behavioral disorders and anxiety disorders and others as disclosed elsewhere herein, obesity and other disorders related to weight and feeding, inflammation, disorders of regulation of breathing, disorders of gastrointestinal function, autonomic regulation in menopausal hot flashes, regulation of hemostasis and sleep/insomnia. Because the trigeminal nerve projects to the dorsal motor nucleus of the vagus nerve, trigeminal nerve stimulation can be used as a safe and minimally invasive method to deliver stimulation to vagus nerve circuits, without implanting a vagus nerve stimulator, and without direct stimulation of the cervical vagus nerve or its branches.

Fatigue

In another aspect, the present disclosure relates to methods, devices and systems used for the treatment of fatigue via stimulation of the superficial elements of the trigeminal nerve ("TNS") to modulate the locus coeruleus or modulate the reticular activating system.

Without wishing to be bound by any particular theory, mechanisms of action by which TNS may counter fatigue include, but are not limited to: (a) influence on the activity of the locus coeruleus, a brain center involved in the production and regulation of the neurotransmitter norepinephrine, and (b) influence on the activity of the reticular activating system (RAS), a brain system involved in regulating levels of consciousness, arousal, wakefulness and attention, and (c) influence on activity of the vagus nerve, which allows for signaling between the brain and multiple internal organs and body systems (e.g. immune), as detailed below.

Tinnitus

Tinnitus, sometimes called "ringing in the ears," is a condition in which a person has the experience of hearing a sound in the absence of corresponding external sound. Tinnitus is common, affecting 20% of the population above the age of 55. It is commonly associated with injury to the auditory system and it can arise in many contexts, including exposure to abnormally loud sounds, ear infections, foreign objects in the ear, nose allergies that prevent (or induce) fluid drain, as a side effect of some medications, as a part of aging, or as a part of a congenital hearing loss. Without wishing to be bound by any particular theory, stimulation of the trigeminal nerve may be able to treat the symptoms of tinnitus.

The cochlear nuclei are the principal brainstem structures responsible for hearing. The paired cochlear nuclei are located in the dorsal and lateral portions of the right and left medulla. The cochlear nuclei are divided into two predominant regions, the dorsal cochlear nucleus (DCN) and the ventral cochlear nucleus (VCN). The cochlear nuclei receive auditory (hearing) input from the cochlear nerves, which receives its input from the ear, specifically the cochlea. Fibers from the cochlear nuclei project to the central auditory pathways, including the lateral lemniscus, inferior colliculus, medical geniculate body, and finally to the primary auditory cortex.

The cochlear nuclei receive input from both the cochlear (auditory) nerve, and other pathways, including the trigeminal nerve, which provides somatosensory information from the face. There are fibers of the trigeminal nerve located over the anterior portion of the external ear canal, and the input from these and other trigeminal branches may help serve to help localizing the source of sound to the listener. Trigeminal nerve input serves to modulate the response of the two cochlear nuclei, and can inhibit or increase the response of the cochlear nuclei to auditory input (sound). (Shore et al., "Dorsal cochlear nucleus responses to somatosensory stimulation are enhanced after noise-induced hearing loss." Eur J Neurosci 2008; 27:155-168)

When the cochlear nerve is injured, the cochlear nuclei (especially the DCN) exhibit enhanced sensitivity to trigeminal input, and increased inhibition of the cochlear nuclei. (Shore et al. 2008) This enhanced sensitivity may play a role in the pathogenesis of tinnitus. (Shore et al. 2008)

Without wishing to be bound by any particular theory, stimulation of the trigeminal nerve may result in reducing tinnitus by modulating trigeminal input to the cochlear nuclei. Since the cochlea exhibit heightened sensitivity to trigeminal input, stimulation of the trigeminal nerve can be performed to reduce or modulate trigeminal enhanced inhibition of the cochlear nuclei after injury, or increase or modulate trigeminal activation of the cochlear nuclei after cochlear nerve injury.

In some embodiments, trigeminal nerve stimulation can be delivered via stimulation of auricular branches located over the anterior auditory canal, or by stimulating cutaneous branches including the auriculotemporal, zygomatic-temporal, mentalis, infraorbital, or supraorbital branches via cutaneous (or transcutaneous) stimulation of these branches. In some embodiments, frequencies may range from 1-5000 Hz, at amplitudes of 0.1-40 mA. In some embodiments, frequencies may range from 1-10000 Hz, at amplitudes of 0.1-40 mA. TNS may be used to calm the dorsal cochlear nucleus (or other relevant structure) with a feedback control loop that may allow the patient in real-time to provide an audiologist with information on which stimulation parameters (such as frequency, pulse width, duty cycle) best mitigate the ringing in the patient's ears. In addition, self-tuning control algorithms can adjust the stimulation parameters to mitigate accommodation effects and changes in the ringing frequency spectrum.

Obesity and Other Disorders Related to Weight and Feeding and Related Conditions Without wishing to be bound by any particular theory, TNS can be used to modulate vagus nerve activity to treat obesity. Conditions related to obesity that may also be treated by modulating vagus nerve activity include: diabetes (worsened in obesity), metabolic syndrome (worsened in obesity), dyslipidemia (worsened in obesity), obstructive sleep apnea (precipitated by excessive soft tissue which may obstruct the airway, in obesity), arthritis (both osteoarthritis, tied to weight load on the joint, and rheumatoid arthritis, where excess weight accelerates joint destruction), and cachexia/anorexia (arising either from cancer or from a psychiatric disorder). The following journal articles may include studies that show an effect on obesity by modulating vagus nerve activity: See e.g. Val-Laillet D, et al., Slower eating rate is independent to gastric emptying in obese minipigs, Physiol Behav., 2010 Nov. 2; 101(4): 462-8, Epub 2010 Aug. 5; Tome D, et al., Protein, amino acids, vagus nerve signaling, and the brain, Am J Clin Nutr., 2009 September; 90(3):838S-843S, Epub 2009 Jul. 29; Kral J G, et al., Vagal nerve function in obesity: therapeutic implications, World J Surg, 2009 October; 33(10):1995-2006.; Green M A, et al., An association between eating disorder behaviors and autonomic dysfunction in a nonclinical population. A pilot study, Appetite, 2009 August; 53(1):139-42, Epub 2009 May 13; Song C K, et al., Anterograde transneuronal viral tract tracing reveals central sensory circuits from white adipose tissue, Am J Physiol Regul Integr Comp Physiol, 2009 March; 296(3):R501-11, Epub 2008 Dec. 24; Acampa M, et al., Sympathetic overactivity and plasma leptin levels in Rett syndrome, Neurosci Lett, 2008 Feb. 13; 432(1):69-72, Epub 2007 Dec. 23; Kapica M, et al., Obestatin stimulates the secretion of pancreatic juice enzymes through a vagal pathway in anaesthetized rats—preliminary results, J Physiol Pharmacol, 2007 August; 58 Suppl 3:123-30; The following journal articles which may include studies that show an effect on cachexia/anorexia by modulating vagus nerve activity: Suneja M, et al., Hormonal regulation of energy-protein homeostasis in hemodialysis patients: an anorexigenic profile that may predispose to adverse cardiovascular outcomes, Am J Physiol Endocrinol Metab, 2011 January; 300(1):E55-64, Epub 2010 Oct. 19; Laviano A, et al., Neural control of the anorexia-cachexia syndrome, Am J Physiol Endocrinol Metab, 2008 November; 295(5): E1000-8, Epub 2008 Aug. 19; Plata-Salaman C R, Central nervous system mechanisms contributing to the cachexia-anorexia syndrome, Nutrition, 2000 October; 16(10):1009-12.

Inflammatory Processes

Without wishing to be bound by any particular theory, TNS can be used to modulate vagus nerve activity to treat inflammatory processes in the body. Conditions related to these inflammatory processes that may also be treated by modulating vagus nerve activity include: asthma, inflammatory bowel disease, atopic dermatitis, sepsis and hepatitis. The following journal articles may include studies that show an effect on inflammatory processes and other conditions in which inflammation plays a role, by modulating vagus nerve activity: inflammatory processes: Minutoli L, et al., Melanocortin 4 receptor stimulation decreases pancreatitis severity in rats by activation of the cholinergic anti-inflammatory pathway, Crit Care Med, 2011 May; 39(5):1089-96; Lehrer P, et al., Voluntarily produced increases in heart rate variability modulate autonomic effects of endotoxin induced systemic inflammation: an exploratory study, Appl Psychophysiol Biofeedback, 2010 December; 35(4):303-15; Ottani A, et al., Melanocortins counteract inflammatory and apoptotic responses to prolonged myocardial ischemia/reperfusion through a vagus nerve-mediated mechanism, Eur J Pharmacol, 2010 Jul. 10; 637(1-3):124-30, Epub 2010 Apr. 10; Thayer J F, Vagal tone and the inflammatory reflex, Cleve Clin J Med, 2009 April; 76 Suppl 2:S23-6; Haensel A, et al., The relationship between heart rate variability and inflammatory markers in cardiovascular diseases, Psychoneuroendocrinology, 2008 November; 33(10):1305-12, Epub 2008 Sep. 25; Thayer J F and Sternberg E M, Neural aspects of immunomodulation: focus on the vagus nerve, Behav Immun, 2010 November; 24(8):1223-8, Epub 2010 Jul. 30; Balbo S L, et al., Fat storage is partially dependent on vagal activity and insulin secretion of hypothalamic obese rat, Endocrine, 2007 April; 31(2):142-8; Pavlov V A, et al., Brain acetylcholinesterase activity controls systemic cytokine levels through the cholinergic anti-inflammatory pathway, Brain Behav Immun, 2009 January; 23(1):41-5, Epub 2008 Jun. 27; Kox M, et al., Increased vagal tone accounts for the observed immune paralysis in patients with traumatic brain injury, Neurology, 2008 Feb. 5; 70(6):480-5; Marsland A L, et al., Stimulated production of proinflammatory cytokines covaries inversely with heart rate variability, Psychosom Med, 2007 November; 69(8):709-16, Epub 2007 Oct. 17; asthma: Li H F and Yu J., Airway chemosensitive receptors in vagus nerve perform neuro-immune interaction for lung-brain communication, Adv Exp Med Biol, 2009; 648:421-6; inflammatory bowel disease: Meregnani J, et al., Anti-inflammatory effect of vagus nerve stimulation in a rat model of inflammatory bowel disease, Auton Neurosci, 2011 Feb. 24; 160(1-2):82-9, Epub 2010 Nov. 11; Van Der Zanden E P, et al., The vagus nerve as a modulator of intestinal inflammation, Neurogastroenterol Motil, 2009 January; 21(1):6-17; atopic dermatitis Boettger M K, et al., Increased vagal modulation in atopic dermatitis., J Dermatol Sci, 2009 January; 53(1):55-9, Epub 2008 Sep. 13; sepsis: Huston J M, et al., Transcutaneous vagus nerve stimulation reduces serum high mobility group box 1 levels and improves survival in murine sepsis, Crit Care Med, 2007 December; 35(12):2762-8; hepatitis: Hiramoto T, et al., The hepatic vagus nerve attenuates Fas-induced apoptosis in the mouse liver via alpha7 nicotinic acetylcholine receptor, Gastroenterology, 2008 June; 134(7):2122-31, Epub 2008 Mar. 8.)

Disorders of the Regulation of Breathing

Without wishing to be bound by any particular theory, TNS can be used to modulate vagus nerve activity to treat disorders of the regulation of breathing. The following link provides a journal article which may include studies that show an effect on disorders of the regulation of breathing by modulating vagus nerve activity: Tadjalli A, et al., Identification of a novel form of noradrenergic-dependent respiratory motor plasticity triggered by vagal feedback, J Neurosci, 2010 Dec. 15; 30(50):16886-95).

Disorders of Gastrointestinal Function

Without wishing to be bound by any particular theory, TNS can be used to modulate vagus nerve activity to treat disorders of gastrointestinal function. These disorders may include: gastroesophageal reflux, diarrhea and constipation, gastrointestinal pain syndromes ("functional bowel syndromes"), post-operative ileus, dyspepsia, motion sickness, and chemotherapy-related nausea and emesis. The following journal articles may include studies that show an effect on disorders of gastrointestinal function by modulating vagus nerve activity: gastroesophageal reflux: Niedringhaus M, et al., "Dorsal motor nucleus of the vagus: a site for evoking simultaneous changes in crural diaphragm activity, lower esophageal sphincter pressure, and fundus tone," Am J Physiol Regul Integr Comp Physiol. (2008) 294(1):R121-31; diarrhea and constipation; dysphagia and other disturbances of swallowing (e.g. following a stroke or traumatic brain injury (TBI)):Bansal V, et al., "Stimulating the central nervous system to prevent intestinal dysfunction after traumatic brain injury," J. Trauma (2010) 68(5):1059-64; gastroparesis: Hasler W L. "Methods of gastric electrical stimulation and pacing: a review of their benefits and mechanisms of action in gastroparesis and obesity," Neurogastroenterol Motil. (2009) 21(3):229-43; gastrointestinal pain syndromes ("functional bowel syndromes"); post-operative ileus: Lubbers T, et al., "Controlling postoperative ileus by vagal activation," World J Gastroenterol (2010) 16(14):1683-87; The F O, et al., "Activation of the cholinergic anti-inflammatory pathway ameliorates postoperative ileus in mice," Gastroenterology (2007) 133(4):1219-28; dyspepsia: Hjelland I E, et al., "Breathing exercises with vagal biofeedback may benefit patients with functional dyspepsia," Scand J Gastroenterol. (2007) 42(9):1054-62; motion sickness: Percie du Sert N, et al., "Telemetry in a motion-sickness model implicates the abdominal vagus in motion-induced gastric dysrhythmia," Exp Physiol. (2010) 95(7):768-73; chemotherapy-related nausea and emesis: Urayama Y, et al., "Electrical and chemical stimulation of the nucleus raphe magnus inhibits induction of retching by afferent vagal fibers," Auton Neurosci. (2010) 152(1-2):35-40; Ray A P, et al., "Receptor-selective agonists induce emesis and Fos expression in the brain and enteric nervous system of the least shrew (Cryptotis parva)," Pharmacol Biochem Behav. (2009) 94(1):211-18; Wang J J, et al., "Electro-acupuncture of Tsusanli and Shangchuhsu regulates gastric activity possibly through mediation of the vagus-solotary complex," Hepatogastroenterology (2007)54(78):1862-67.

Autonomic Instability of Menopausal Hot Flashes

Without wishing to be bound by any particular theory, TNS can be used to modulate vagus nerve activity to treat autonomic instability of menopausal hot flashes. The following journal article may include studies that show an effect on autonomic instability of menopausal hot flashes by modulating vagus nerve activity: Thurston R C, et al., "Hot flashes and cardiac vagal control: a link to cardiovascular risk?," Menopause (2010) 17(3):456-61.

Regulation of Hemostasis (Blood Clotting)

Without wishing to be bound by any particular theory, TNS can be used to modulate vagus nerve activity to regulation hemostasis (blood clotting). The following journal articles may include studies that show an effect on hemostasis by modulating vagus nerve activity: Czura C J, et al., "Vagus nerve stimulation regulates hemostasis in swine," Shock (2010) 33(6):608-13; Kraemer M, et al., "The influence of vasovagal response on the coagulation system," Clin Auton Res. (2010) 20(2):105-11.

Insomnia and Disturbances of Sleep

Sleep disturbances can arise in a range of conditions, including sleep apnea, hyperthyroidism, depression, and primary insomnia. Stimulation of the trigeminal nerve may be able to treat sleep disturbances by means of its influences on brain systems related to wake/sleep cycles and arousal. Without wishing to be bound by any particular theory, projections from the trigeminal nerve to the nucleus of the tractus solitarius (NTS) convey signals to the NTS and then to other brain regions involved in the regulation of sleep and wakefulness, for example, via the parabrachial nucleus, to the hypothalamus, amygdala, insula, lateral prefrontal cortex, and other regions of relevance (A. Jean. *Arch Int Physiol Biochim Biophys.* 1991 99:A3-52; T. R. Henry *Neurology* 2002 59(6 Suppl 4):S3-14; R. Ruffoli et al., *J Chem Neuroanat*, in press). Other projections to the locus coeruleus (LC), the brain's major source of the neurotransmitter norepinephrine, and to the reticular activating system (RAS) may also play a role in sleep/wake regulation.

As supporting experimental data of the beneficial effects of TNS on insomnia, we examined the scores on the insomnia items of the Quick Inventory of Depressive Symptomatology (www.ids-qids.org), for ten adults with major depression who participated in a clinical trial of TNS. On this well-established rating scale, the first three questions assess (a) sleep onset insomnia (i.e., delay in falling asleep), (b) nocturnal insomnia (awakening during the night), and (c) early morning insomnia (awakening earlier than intended and being unable to return to sleep). Summing the responses to these three items gives an index of severity of insomnia in these subjects, ranging from zero (no symptoms) to six (maximal disturbance across all three types of insomnia symptom). Over the course of this 8 week trial, this measure of insomnia severity fell from an average of 2.5 (1.8 s.d.) to 1.2 (1.0 s.d.), a decrease of over 50% which achieved statistical significance (2-tail paired t-test p<0.05).

Neurological Disorders

The neuroanatomic pathways allow targeted modulation of activity in areas involved in epilepsy and other neurological conditions and disorders (e.g. locus coeruleus, anterior cingulate, insular cortex). Thus, the systems, devices and methods as disclosed herein utilize the brain's existing infrastructure to transmit signals to the targets of interest. Example conditions and disorders include: coma and vegetative State, headache and migraine, movement disorders, include, but are not limited to, tremors, twitches, and spasms, involuntary increases in tone of muscles, such as dystonias, and complex movements, such as dyskinesias and choreas, tardive and other dyskinesias.

For a discussion of certain embodiments of methods, systems and devices using implantable electrodes according to aspects of the present disclosure, reference is now made to FIGS. 4A-7, which show various embodiments of the systems and devices that may be used for the percutaneous or subcutaneous stimulation of the superficial branches of the trigeminal nerve and methods of using the same.

According to one aspect of the present disclosure, a method of treating medical disorders using trigeminal nerve stimulation ("TNS") is provided. In some embodiments, the method of treating medical disorders by stimulating superficial branches of the trigeminal nerve comprises implanting electrodes adjacent to, in proximity to, or distal to at least one of the three paired foramina or superficial branches of the trigeminal nerve in the face (FIGS. 1A and 1B), and stimulating the electrodes using a neurostimulator for a fixed time at specified operational parameters. The electrode assembly placement does not require intracranial invasion (i.e. implantation below the skull) because the electrode assembly is attached or otherwise anchored to subcutaneous or connective tissues located above the periosteum or pericranium and below the epidermis in order to place the electrode assembly in proximity to, adjacent to, in contact with or distal to the target nerve branch. In some embodiments, the electrode assembly may be configured to stimulate the smaller branches of the trigeminal nerve. Surprisingly, placement of the assembly further away from the brain and the main branch of the nerve is believed to be as efficacious as direct attachment or other contact with the main branch of the nerve and may provide increased safety for the patient. It should be appreciated that the operations/steps of the methods described herein may be performed in the order illustrated, in another suitable order and/or one or more operations may be performed simultaneously. Moreover, in some embodiments, the methods may include more or fewer operations/steps than those illustrated/described elsewhere herein.

Figure 4A:
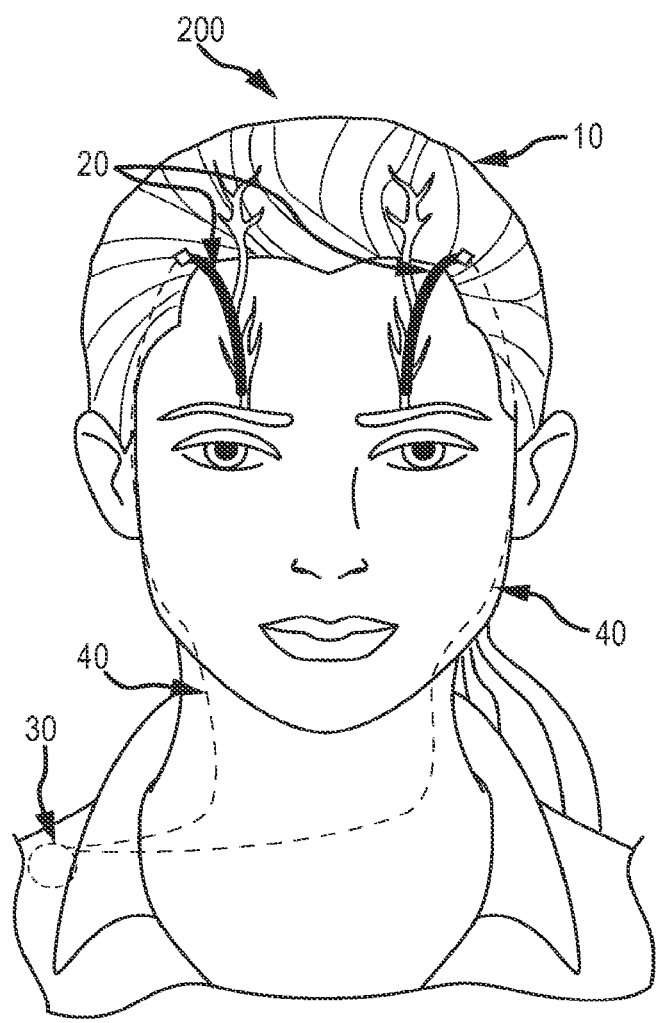
FIG. 4A shows a subject wearing an embodiment of a system for trigeminal nerve stimulation including a subcutaneous electrode assembly provided according to aspects of the present disclosure.

In one embodiment, the implanted electrodes are positioned adjacent to the foramina of the supraorbital or ophthalmic nerves (FIG. 1A, Foramen 1) since unilateral stimulation or bilateral stimulation of the trigeminal nerve is achievable by placing single or separate electrodes on the right and/or left sides. In one embodiment, the electrode assembly is configured for unilateral stimulation. In one embodiment, the electrode assembly is configured for bilateral stimulation. In some embodiments, bilateral stimulation may offer similar or better efficacy than unilateral stimulation because the function of different brain structures may not be the same on right and left. There may also be synergistic effects that arise with bilateral stimulation. FIG. 4A shows an example of a patient 10 who has been implanted with two separate electrodes 20 in the soft tissues of the forehead, one over each eyebrow, corresponding to the foramina of the ophthalmic nerves. In alternative embodiments, the implanted/implantable electrode(s) can be positioned adjacent to or in proximity to the infraorbital foramen (infraorbital nerves) (FIG. 1A, Foramen 2) or the mentalis foramen (mentalis nerves) (FIG. 1B, Foramen 3). In other embodiments, electrodes may be placed adjacent to, in proximity to, or in contact with the supratrochlear nerve, infratrochlear nerve, zygomaticotemporal, zygomaticofacial, zygomaticoorbital, nasal, and/or auriculotemporal nerves and/or their respective foramina. In yet other embodiments, the stimulation can be unilaterally applied near one superficial foramen of the trigeminal nerves. Unilateral stimulation or bilateral stimulation of the trigeminal nerve is achievable by placing single or separate electrodes on the right and/or left sides of the face to unilaterally apply stimulation near one superficial foramen of the trigeminal nerves. In other embodiments, the method of treating fatigue and other medical disorders includes implanting electrodes over a plurality of superficial foramina in the face and simultaneously or asynchronously stimulating different trigeminal nerves. In other embodiments, the stimulation may take place in the cutaneous territories of branches of the trigeminal nerves, without attachment to the nerves.

In one embodiment, electrodes may penetrate percutaneously, i.e., through the surface of the skin, in order to be placed in proximity to the intended branch(es) of the trigeminal nerve, while the pulse generator remains external to the body. In this embodiment (percutaneous TNS or pTNS), some elements of the system are implanted in the tissues of the skin, while other elements are not implanted.

In one embodiment, as can be understood from FIGS. 4A-7, a system 200 for treatment of medical disorders via TNS includes an electrode assembly 20, electrical cable or wire 40 and a neurostimulator or pulse generator 30.

The pulse generator may be any type of appropriate stimulating, signal generating device. In some embodiments, the pulse generator 30 may include electronic circuitry for receiving data and/or power from outside the body by inductive, radio-frequency (RF), or other electromagnetic coupling. In some embodiments, electronic circuitry includes an inductive coil for receiving and transmitting RF data and/or power, an integrated circuit (IC) chip for decoding and storing stimulation parameters and generating stimulation pulses, and additional discrete electronic components required to complete the electronic circuit functions, e.g. capacitor(s), resistor(s), transistor(s), coil(s), and the like.

In other embodiments, neurostimulator 30 may include a programmable memory for storing a set(s) of data, stimulation, and control parameters. Among other things, memory may allow stimulation and control parameters to be adjusted to settings that are safe and efficacious with minimal discomfort for each individual. Specific parameters may provide therapeutic advantages for various medical disorders. For instance, some patients may respond favorably to intermittent stimulation, while others may require continuous stimulation to treat their symptoms.

In some embodiments, the neurostimulator 30 may include a power source and/or power storage device. Possible options for providing power to the system include but are not limited to: an external power source coupled to neurostimulator 30, e.g., via an RF link, a self-contained power source utilizing any suitable means of generation or storage of energy (e.g., a primary battery, a replenishable or rechargeable battery such as a lithium ion battery, an electrolytic capacitor, a super-capacitor, a kinetic generator, or the like), and if the self-contained power source is replenishable or rechargeable, means of replenishing or recharging the power source (e.g., an RF link, an optical link, a thermal link, an inductive link, or other energy-coupling link).

In some embodiments, neurostimulator 30 operates independently. In other embodiments, neurostimulator 30 operates in coordination with other implanted device(s) or other device(s) external to the patient's body. For example, a neurostimulator may communicate with other implanted neurostimulators, other implanted devices, and/or devices external to a patient's body via, e.g., an RF link, an ultrasonic link, a thermal link, an optical link, or the like. Specifically, a neurostimulator may communicate with an external remote control (e.g., patient and/or physician programmer) that is capable of sending commands and/or data to a neurostimulator and that may also be capable of receiving commands and/or data from a neurostimulator.

In one embodiment, the electrical cable or wire 40 is configured to provide a physical and electrical link between the pulse generator 30 and the electrode assembly 20. In other embodiments, the pulse generator 30 and the electrode assembly 20 communicate wirelessly (i.e. the wire 40 is not used). The system 200 and/or the electrode assembly 20 may be part of a kit. In some embodiments, the kit may also include instructions for treatment of various medical disorder according to a method disclosed herein. In some embodiments, the kit may also include instructions for monitoring the clinical effects of the stimulation to achieve proper adjustment of stimulation parameters and system configuration. The instructions may be provided in any readable format or as a link to a website.

In some embodiments, the system may include a regulation device. The regulation device is configured to be attached to the neurostimulator 30 and, in some embodiments, is configured to govern the maximum charge balanced output current below approximately 1-25 mA to minimize current penetration to the brain and increase patient tolerance. The regulation device may be internally programmed to range from 0.25-5.0 mA, 0-10 mA, 0-15 mA, depending on the surface area, placement, and orientation of the electrode, and whether the electrode is stimulating near or adjacent to the skull, or away from the skull, where current ranges may be higher or lower.

In some embodiments, the system may utilize a closed loop design and may include a closed loop device or sensing device. In such a system, the closed loop device may include the stimulating electrode or additional set of electrodes, indwelling catheters, or cutaneous or implantable physiologic monitors. The device may be configured to detect heart rate, pulse oximetry, cerebral blood flow, systolic, diastolic blood pressure, or mean arterial pressure, transcranial Doppler, cardiac parameters (ejection fraction, pulmonary, atrial, or ventricular pressures), heart rate variability (using time, frequency, or non-linear or other measures of heart rate variability), the presence of molecules that could signify a potentially-dangerous condition (e.g., tropinin in the bloodstream, a biomaker that may indicate injury to the heart muscle tissue, as might be treated in an ambulance, an emergency room, and/or an intensive care unit) or the achievement of a desired clinical effect (e.g., levels of pro-inflammatory cytokines), or other physiologic parameters to provide self-tuning adaptive feedback control for the neurostimulator including, but not limited to, fuzzy controllers, LQG controllers and artificial neural networks (ANN). Adaptive learning controllers can learn from the previous response of a particular patient or similar patients to stimulation settings which helped alleviate conditions being treated. In some embodiments, this qualitative and/or quantitative feedback may be used by the system to automatically or otherwise adjust the stimulation parameters in a closed-loop fashion to optimize the clinical effects of the stimulation.

Figure 4B:
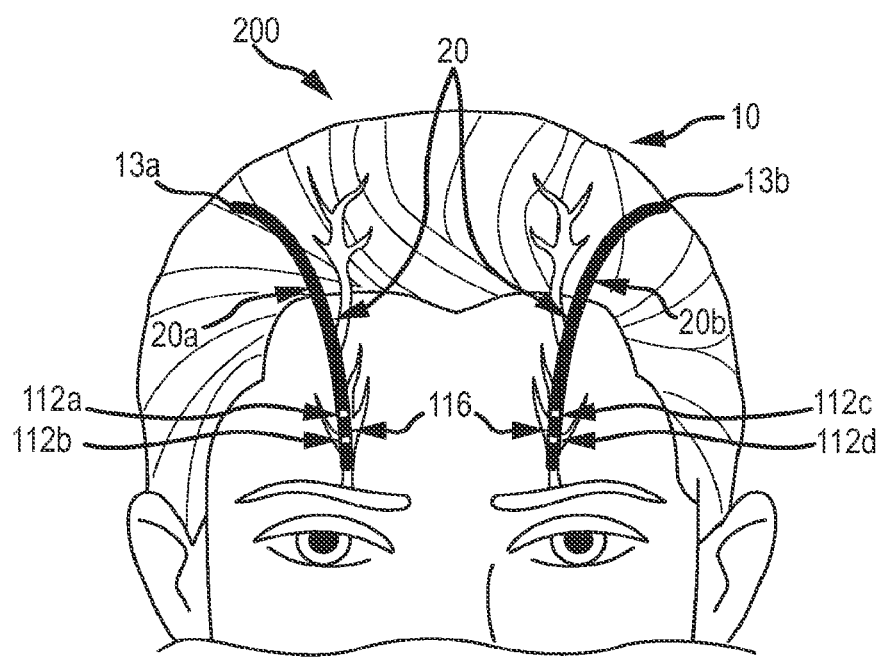
FIG. 4B is the subcutaneous electrode assembly of FIG. 4A, wherein a multicontact electrode is shown.

In one embodiment, as shown in FIGS. 4A-4B, the electrode assembly 20 is also referred to as a bilateral supraorbital electrode. The electrode assembly 20 is connectable to an implanted/implantable neurostimulator by electrical cables 40. Alternatively, the electrodes may be connectable to an external neurostimulator wirelessly, with transfer of energy across the skin by inductive coupling between a coil implanted in the patient and a coil in the external neurostimulator. As an additional alternative, the electrode assembly 20 may be placed percutaneously while the neurostimulator is located externally, and the electrical cables 40 connect the implanted electrodes with the external neurostimulator.

In one embodiment, as illustrated in FIG. 4B, an electrode assembly 20 may include electrodes 20a, 20b configured for the bilateral simultaneous and asynchronous stimulation of the ophthalmic nerves and other nerves as described herein. The electrodes 20a, 20b of the electrode assembly 20 comprise a first pair of contacts 112a, 112b configured for implantation in a first region of the patient's face, such as the patient's right forehead, and a second pair of contacts 112c, 112d configured for implantation in a second region of the patient's face, such as in the patient's left forehead. In other embodiments, the first and second regions of the patient's face may be on the same side of the face, e.g. the right or left side, but may be at different locations, e.g. the right forehead or the right upper face area, the right cheek area or middle face area or the right lower face area or mouth/jaw area. The electrode assembly 20 may also include an insulated region 116 or a plurality of insulated regions 116 configured to separate the individual electrode contacts. The first pair of contacts comprises a first upper contact 112a and a first lower contact 112b, while the second pair of contacts comprises a second upper contact 112c and a second lower contact 112d. The electrode assembly 20 comprises four electrodes that deliver the stimulation pulses to the nerves bilaterally. While the electrode assembly 20 is shown in FIG. 4B with only pairs of electrical contacts (112a/b, 112c/d), in other embodiments, there may be a greater or lesser number of contacts on each of the assemblies 20a and 20b.

Figure 5:
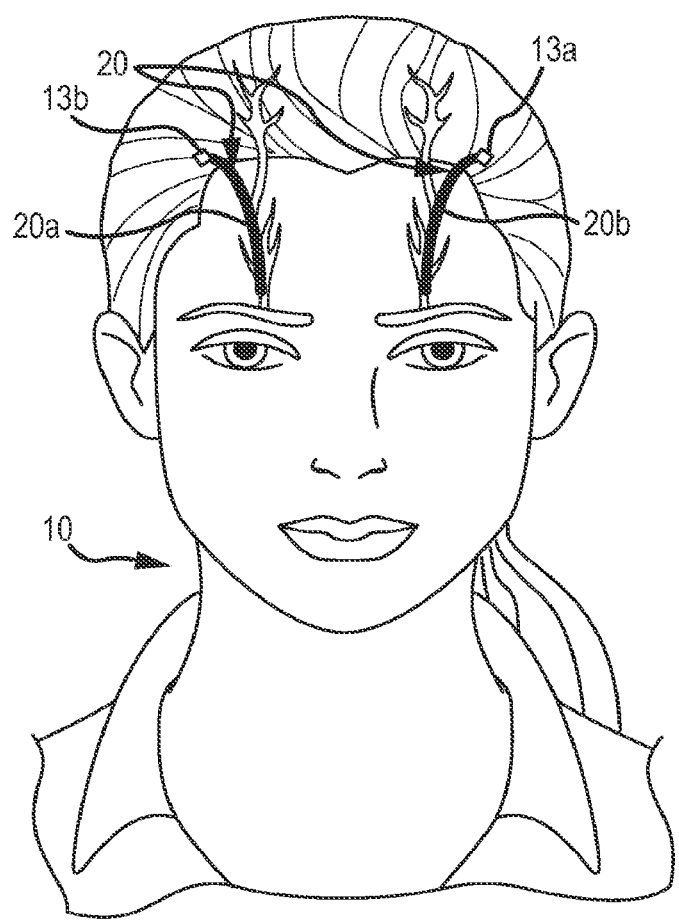
FIG. 5 depicts another embodiment of a subcutaneous electrode assembly which may be used with the system of FIG. 4A.

FIG. 5 shows another embodiment of an electrode assembly 20 that may be used in the system 200. FIG. 5 shows an example of a patient 10 who has been implanted with the electrode assembly 20, provided in accordance with the present disclosure. In one embodiment, as shown in FIG. 5, the electrode assembly may comprise two implanted electrodes 20a, 20b which are placed adjacent to the supraorbital foramina, located over the orbital ridge approximately 2.1 to 2.6 cm lateral to the nasal midline. As shown in FIG. 5, the superior ends 13a, 13b of the electrodes 20a, 20b indicate the place at which the electrodes 20 connect to leads (see FIG. 4A) for conveying the electrical stimuli from the neurostimulator (see FIG. 4A). The neurostimulator itself may be placed in a variety of locations under the skin, such as pectorally, and the leads placed under the skin of the patient to connect them.

In some embodiments, such as the embodiments shown in FIGS. 4A-5, the neurostimulation may be provided using an electrical neurostimulator at the following exemplary settings: frequency between approximately 1-150 Hz, current between approximately 1-25 mA, pulse duration of between approximately 50-250 microseconds, a duty cycle of up to 50%, for at least one hour per day. In some embodiments for treatment of fatigue, the neurostimulation may be provided using an electrical neurostimulator at the following exemplary settings: frequency 120 Hz, current up to 25 mA, pulse duration (pulse width) of 250 microseconds, a duty cycle of 30 seconds on/30 seconds off, for at least eight hours per day. In some embodiments, the current amplitudes are less than 7 mA, or less than 6 mA, depending on the size, impedance, resistance, or configuration of the electrode(s). In some embodiments, the current amplitude is between about 2.5 mA and about 5 mA. In still another embodiment, the output current may be limited to an exact current, e.g. 5 mA, up to a maximum of a fixed current of 7 mA, depending on the size, resistance, or impedance of the electrode. In another embodiment, the output current is limited to a range not to exceed 10 mA, or 7 mA, or 5 mA. For patient comfort and low power consumption, stimulation parameters at the lower end of these ranges may be used, but this may be balanced with differences in clinical effect which may vary over the range of stimulation parameters. In other embodiments, different values of the operational parameters may be used.

In alternative embodiments, a single external electrode can be used. For patient comfort and low power consumption, stimulation parameters at the lower end of these ranges may be preferred. In other embodiments, different values of the operational parameters may be used, but the values are balanced with differences in clinical effect which may vary over the range of stimulation parameters. In alternative embodiments, a single implanted electrode with one or more contacts can be used.

Figure 6:
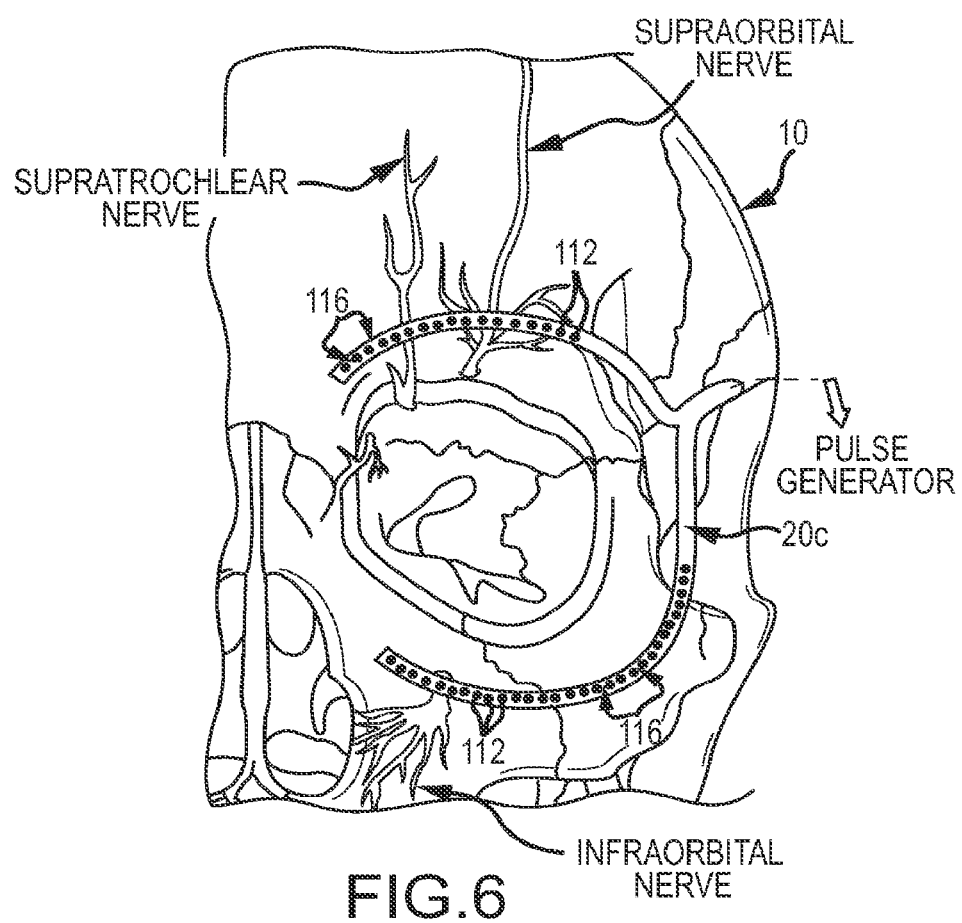
FIG. 6 depicts another embodiment of a subcutaneous electrode assembly configured for stimulation of a plurality of nerve branches which may be used with the system of FIG. 4A.

FIG. 6 depicts still another embodiment of an electrode assembly 20 that may be used in the system 200. In some embodiments, as shown in FIG. 6, the electrode assembly 20 may comprise a multicontact electrode 20c with a plurality of contacts 112 and a plurality of insulated regions 116. The electrode assembly of FIG. 6 is configured to unilaterally stimulate both the supraorbital nerve and the infraorbital nerve. In other embodiments, the electrode assembly may comprise a plurality of multicontact electrodes which may include a plurality of contacts and a plurality of insulated regions. In various embodiments, the geometry or layout of the electrode assembly may be a linear electrode with a single contact or a series or plurality of conductive contacts and insulating spaces, or a flatter, "ribbon" or "strip" electrode, also with the possibility of one or more conductive area(s) and insulated area(s) on the surface(s). Those of skill in the art will recognize that other related geometries are also contemplated to be within the scope of the present disclosure.

As can be understood from FIG. 6, in one embodiment, the electrode assembly may be implanted unilaterally. The electrode assembly may also be configured to stimulate more than one nerve. For example, as shown in FIG. 6, the electrode assembly is configured to be placed at, near or over a plurality of superficial foramina in the face and simultaneously or asynchronously stimulate different trigeminal nerves (e.g. the supraorbital nerve and the infraorbital nerve).

Those skilled in the art will appreciate that various adaptations and modifications of the above-described embodiments of the electrode assembly 20 are within the scope and spirit of the present disclosure. For example, one embodiment of the present device comprises a unilateral electrode assembly configured for the unilateral stimulation of the ophthalmic nerve, supraorbital nerve and the infraorbital nerve (see FIG. 6). In other embodiments, the implantable electrode assembly may be configured for the stimulation of the infraorbital nerves or the mentalis nerves (individually or in combination with other nerves). In other embodiments, an electrode assembly may be configured for the simultaneous or asynchronous stimulation of a plurality of branches of the trigeminal nerve, either unilaterally or bilaterally. In other embodiments, both external, transcutaneous electrodes and implanted subcutaneous and/or percutaneous electrodes are used to simultaneously or asynchronously stimulate one or more branches of the trigeminal nerves. One example of the external, transcutaneous electrode assemblies which may be used are described in U.S. Patent Application Publication No. 2014/0135886, entitled "Devices, Systems, and Methods for the Treatment of Medical Disorders," filed on even date herewith and which is hereby incorporated by reference.

For ease of the reader, the remaining discussion is made with respect to FIG. 4B. However, it is understood that the disclosure also applies to embodiments which include a single multicontact electrode with a plurality of contacts, a single contact electrode, and embodiments which include a plurality of multicontact electrodes with a plurality of contacts and embodiments configured for unilateral or bilateral stimulation and other embodiments within the spirit and scope of the present disclosure.

As can be understood from FIG. 4B, the electrode assembly 20 is configured to stimulate both the right and left ophthalmic nerves either simultaneously or asynchronously. The placement of the first implanted electrode with contact pair 112a, 112b and the second electrode with contact pair 112c, 112d on opposite sides of the nasal midline assures that stimulation current moves orthodromically or in the direction of the afferent ophthalmic or supraorbital nerve. Furthermore, this configuration of the electrode assembly 20 allows the electrode contact points 112a/112b and 112c/112d to be stimulated independently and/or unilaterally, as the response to stimulus may be localized and thus varied from one side of the midline to the other side. Depending on the location of the pulse generator, in some embodiments, the electrodes and/or their connectors (e.g. the wires 40) are longer than 150 mm where the supraorbital, infraorbital and/or the mentalis branch is the desired target. For other branches, a shorter electrode/connector length may be desired depending on the placement of the pulse generator (neurostimulator).

For stimulations where electrical pulses of a single polarity are generated, the upper electrode contact points 112a, 112c and lower contact points 112b, 112d have fixed polarities. For stimulations where electrical pulses of alternating polarities are generated, the upper contact points 112a, 112c and lower contact points 112b, 112d have alternating polarities.

Each of the contacts 112a, 112b, 112c, 112d is configured to deliver an electrical pulse with minimal scalp tissue injury due to excess charge accumulation, and, in some embodiments, with minimal potential for current penetration beyond the inner surface of the skull bone. In one embodiment, the distance between the first implanted electrode contact pair 112a, 112b and the second electrode contact pair 112c, 112d is configured to stimulate the ophthalmic nerves while minimizing any current delivery to the surface of the brain. The electrode size and the inter-electrode distance of electrode placement may vary for children and adults, males and females, depending upon the dimensions of an individual person's anatomy.

Electrode assembly 20, and in particular the contact points 112a, 112b, 112c, 112d, may be made of a noble or refractory metal or compound, such as titanium, titanium nitride, platinum, iridium, tantalum, niobium, rhenium, palladium, gold, nichrome, stainless steel, or alloys of any of these, in order to avoid corrosion or electrolysis which could damage the surrounding tissues and the device. Other compounds for implantable electrodes will be apparent to one skilled in the art.

In various embodiments, the distance between contacts 112a and 112b and the distance between contacts 112c and 112d can be in a range greater than, equal to, and/or less than one or more of 0.1 cm, 0.5 cm, 1 cm, 2 cm, 3 cm, 4 cm, 5 cm, 6 cm, 7 cm, 8 cm, 9 cm, or 10 cm. Those of skill in the art will recognize that one or more of the above distances can be used as a border of a range of distances.

Those skilled in the art will appreciate that various adaptations and modifications of the above-described embodiments of the electrode assembly 20 are within the scope and spirit of the present disclosure. For example, one embodiment of the present device comprises a unilateral electrode assembly configured for the unilateral stimulation of ophthalmic nerves (e.g. supraorbital nerve). In other embodiments, the implantable electrode assembly may be configured for the stimulation of the infraorbital nerves or the mentalis nerves. In other embodiments, an electrode assembly may be configured for the simultaneous stimulation of a plurality of branches of the trigeminal nerve.

In some embodiments, both external, transcutaneous electrodes and implanted electrodes are used to simultaneously or asynchronously stimulate one or more branches of the trigeminal nerves.

In some embodiments, sensing electrodes are included in the electrode array to monitor physiological parameters, such as electrocardiographic data, or other relevant physiologic data such as oxygen saturation, carbon dioxide, blood pressure, basal metabolic rate, or other measures, and permit a feedback system that can adaptively adjust the stimulation parameters to optimize therapeutic benefit and safety. In some embodiments, the sensing electrode is one of the stimulating electrodes and is used for sensing during the 'off' part of the duty cycle. In some embodiments, the sensing electrode is an additional electrode and is dedicated to sensing only.

As can be best understood from FIGS. 4A-4B, the electrode assembly 20 is implanted in the soft tissues of the forehead of the patient 20. The electrode 20 is then connected to an implanted neurostimulator 30 via the implanted electrical cables 40, which are placed under the patient's skin. In the illustrated embodiment, the stimulation via the neurostimulator 30 is via electrical cables 40. In alternative embodiments, the electrical stimulation can be performed wirelessly, with an external, non-implanted neurostimulator, which uses inductive coupling to deliver energy to the implanted electrode assembly 20. The stimulation is carried out at the above-described values of the operational parameters. The values of the operational parameters are advantageously selected such that a patient will experience a stimulation sensation, such as mild tingling over the forehead and scalp, without causing the patient significant discomfort or pain and with minimal current penetration to the brain. These values may vary according to the treatment of interest. In other alternative, percutaneous TNS embodiments, the electrode assembly 20 is placed in the patient's skin, while the non-implanted neurostimulator is placed externally, and the two are connected via electrical cables 40.

In another aspect of the present disclosure, embodiments in which stimulation is applied to fibers of multiple cranial nerves ("polycranial nerve stimulation") are disclosed. In such embodiments, and with respect to FIG. 7, stimulation can be applied to aspects of the trigeminal nerve which innervate portions of the ear, particularly the auricle (external ear) 317 and the ear canal 315, 316. In addition, in this area of the body, more than one nerve may supply adjacent and/or overlapping areas of a single anatomical structure. Sensory signals from these skin areas may be conveyed to centers in the brain by nerves including the auriculotemporal nerve, a branch of the trigeminal nerve, and also by other nerves (e.g., posterior auricular nerve, from the facial nerve, or the auricular branch of the vagus nerve). To achieve stimulation of the trigeminal nerve and other nerves in this manner, electrodes may be placed under the skin of the auricle and/or of the ear canal. Such embodiments are less noticeable when worn by a patient and may increase patient use and/or compliance.

Figure 7:
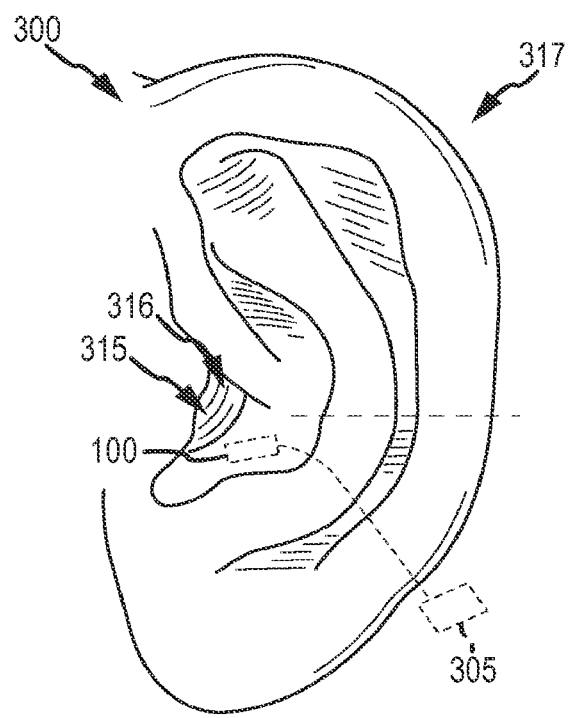
FIG. 7 illustrates an ear and another embodiment of a system according to aspects of the present disclosure.

In one embodiment, as illustrated in FIG. 7, an implantable polycranial nerve stimulation system 300 may include electrode(s) or an electrode assembly 100 configured to be implanted under the surface of the skin within the ear canal 315, at the opening of the ear canal 316 or at/about another surface of the external ear 317. In some embodiments, the electrode(s) or electrode assembly 100 may be an assembly as disclosed elsewhere herein.

The system 300 may also include a pulse generator 305. In some embodiments, the pulse generator 305 may be implanted under the skin in an area at or near the ear. The electrode(s) or electrode assembly 100 and the pulse generator 305 may be connected via a wire or similar connection, or may communicate wirelessly. Such communication may employ radio frequency, ultrasound, or other methods as may be apparent to one skilled in the art.

In one embodiment, a generator is implanted under the skin near the ear, and the electrode assembly (e.g. micro electrodes) are placed on or in the ear. In this way, the wires do not cross a joint or any location exhibiting significant movement; motion across a joint predisposes to problems with the leads migrating or penetrating through the skin (from the inside to the outside). The motion around the ears is generally very small.

The stimulation is carried out at the operational parameters as described herein. In some embodiments, the values of the operational parameters may be selected such that a patient will experience a stimulation sensation, such as mild tingling over the forehead, scalp, or teeth, without causing the patient significant discomfort or pain. These values may vary according to the treatment of interest.

According to one aspect of the present disclosure, there is provided a method of treatment of fatigue or other medical disorders using the electrode assembly 20, as described above. In one embodiment, the method of treating fatigue or other medical disorders includes implanting the electrode assembly 20 to the forehead of a patient, connecting the electrode assembly 20 to a neurostimulator 30, and stimulating the electrode assembly 20 at defined values of the operational parameters. In one embodiment, the bilateral supraorbital electrode 20 as disclosed herein is stimulated at a stimulus frequency between about 1 and about 150 Hz, at a pulse duration between 50 microseconds (μsec) to 250 μsec, at an output current of between approximately 1 and 25 mA for at least one-half to one hour per day. In some embodiments for treatment of fatigue, the neurostimulation may be provided using an electrical neurostimulator at the following exemplary settings: frequency 120 Hz, current up to 25 mA, pulse duration (pulse width) of 250 microseconds, a duty cycle of 30 seconds on/30 seconds off, for up to eight hours per day. In some cases, stimulation can be provided for less than one-half hour per day or may be provided for up to 24 hours per day.

Accepted standards of safe stimulation may be incorporated for chronic stimulation. Parameters may be selected or calculated to deliver no stimulation or negligible stimulation to the surface of the brain. The currently accepted safe parameters for chronic stimulation are less than a charge per phase of <20 $\mu C/cm^2$/phase at the surface of the brain (Exp Neurol 1983; 79:397-41). In general, for any region of the surface of the brain, the cumulative charge per phase resulting from all the electrode contacts should not exceed this threshold. It is recognized that these guidelines are subject to change, and that parameters should be selected which deliver no current or negligible current to the surface of the brain, while still being sufficient to stimulate the nerves disclosed herein.

According to one aspect of the present disclosure, the method of treating medical disorders by TNS includes selecting optimal values for the operational parameters for the stimulation of each individual patient. In one embodiment, the values of the operational parameters are selected such that a patient will experience a stimulation sensation, such as a mild tingling over the forehead, scalp, or face, without being in discomfort or in pain. In some embodiments, lower currents (e.g. 0.05-5 mA) and careful electrode placement may be selected to avoid recruitment of nerves supplying pain sensation to the teeth. In some embodiments, lower currents (e.g. 0.05-5 mA) may also be selected to avoid penetration of the current into the skull and brain, especially in supraorbital locations. In some embodiments, the output current density is less than 7 mA, or less than 6 mA, depending on the size, impedance, resistance, or configuration of the electrode(s). In some embodiments, the output current density is between about 2.5 mA and about 5 mA. In still another embodiment, the output current may be limited to an exact current, e.g. 5 mA, up to a maximum of a fixed current of 7 mA, depending on the size, resistance, or impedance of the electrode. In another embodiment, the output current is limited to a range not to exceed 10 mA, or 7 mA, or 5 mA. In general, the stimulation would yield no or negligible charge densities at the cerebral cortex. In some cases, stimulation can be provided for less than one-half hour per day.

In some embodiments, the electrodes are arrayed in pairs, arranged as two pairs (4-contact), three pairs (six contact), or four pairs (eight contact), with current moving orthodromically (toward the proximal trigeminal ganglion). The electrodes are ≤than 50 mm$^2$ and <450 mm$^2$. In some embodiments, the electrodes are between approximately 50 mm$^2$ and 450 mm$^2$. The current amplitude provided by the system/electrode assembly is <2.5 mA, <5.0 mA, <7.5 mA, or not greater than 10 mA's). Such low current may reduce or minimize pain felt by the patient. In some embodiments, the specific limits to output current may be a function of physician programming, or automatically adjusted or programmed to the type, number of contacts, surface area, or impedance/resistance of the device.

In one embodiment, the method of selecting operational parameters includes evaluating variables such as the pulse duration, the electrode current, the duty cycle and the stimulation frequency; the parameters are selected to ensure that the total charge, the charge density, and charge per phase are well within accepted safety limits for the scalp or facial tissue, nerve and brain. Additionally, in some embodiments, selection of the electrical stimulation parameters, electrode design, and inter-electrode distance is made such that the electrical stimulation zone includes the superficial elements of the trigeminal nerves (approximately 3-4 mm deep), while preventing or minimizing current penetration beneath the bone tissue of the skull.

In various embodiments, the stimulation parameters delivered by the implanted pulse generator (neurostimulator) may be determined (programmed) at the time the device is surgically implanted. In other embodiments, these parameters may be modified, controlled, or otherwise programmed by an external device. This external programming element communicates with the implanted components wirelessly. This may take place, for example, by radiofrequency signals, by inductive coupling, or other means apparent to one skilled in the art.

In various embodiments, the stimulation is delivered at a specific pulse width or range of pulse widths. The stimulation can be set to deliver pulse widths in the range greater than and/or less than one or more of 10 μs, 20 μs, 30 μs, 40 μs, 50 μs, 60 μs, 70 μs, 80 μs, 90 μs, 100 μs, 120 μs, 125 μs, 150 μs, 175 μs, 200 μs, 225 μs, 250 μs, 300 μs, up to 500 μs. Those of skill in the art will recognized that one or more of the above times can be used as a border of a range of pulse widths.

In some embodiments, the stimulation amplitude is delivered as a voltage or current controlled stimulation. In other embodiments it can be delivered as a capacitive discharge. In various embodiments, the current amplitude can be in any range within a lower limit of about 300 μA and an upper limit of about 25 mA, depending on the surface area of the electrodes, inter-electrode distance, the branch(es) stimulated, and the modeling data as described above. In some embodiments, the current used will range from 1 mA to 25 mA. In other embodiments, the current used will range from 5-25 mA. In various embodiments, the amplitude can be in a range greater than and/or less than one or more of 50 μA, 75 μA, 100 μA, 125 μA, 150 μA, 175 μA, 200 μA, 225 μA, 250 μA, 275 μA, 300 μA, 325 μA, 350 μA, 375 μA, 400 μA, 425 μA, 450 μA, 475 μA, 500 μA, 525 μA, 550 μA, 575 μA, 600 μA, 625 μA, 650 μA, 675 μA, 700 μA, 725 μA, 850 μA, 875 μA, 900 μA, 925 μA, 950 μA, 975 μA, 1 mA, 2 mA, 3 mA, 4 mA, 5 mA, 6 mA, 7 mA, 8 mA, 9 mA, 10 mA, 20 mA and 25 mA. In some embodiments, the current amplitudes are less than 7 mA, or less than 6 mA, depending on the size, impedance, resistance, or configuration of the electrode(s). In some embodiments, the current amplitude is between about 2.5 mA and about 5 mA. In still another embodiment, the output current may be limited to an exact current, e.g. 5 mA, up to a maximum of a fixed current of 7 mA, depending on the size, resistance, or impedance of the electrode. In another embodiment, the output current is limited to a range not to exceed 10 mA, 7 mA, or 5 mA. Those of skill in the art will recognize that one or more of the above amplitudes can be used as a border of a range of amplitudes, and that devices which use a voltage-based output can deliver a voltage output which at a range of electrode impedances would yield similar currents. The current may be delivered constantly or intermittently.

In some embodiments, treatment at a given current amplitude is delivered so as to minimize or eliminate any spread of current to the cerebral cortex, while ensuring that accepted limits of charge density and charge per phase at the brain surface (e.g., generally <20 μC/cm$^2$/phase, Exp Neurol 1983; 79:397-411) are adhered to, for the safety of the patient. Without wishing to be bound by any particular theory, it is believed that with the use of multicontact electrodes as described herein, even lower charge densities may be employed because more fibers within the nerves may be engaged in the neurostimulation process.

In various embodiments, the stimulation can be delivered at one or more frequencies, or within a range of frequencies. In some embodiments, the frequency used will range from 1 Hz to 150 Hz. The stimulation can be set to be delivered at frequencies less than, and/or greater than one or more of 50 Hz, 45 Hz, 40 Hz, 35 Hz, 30 Hz, 25 Hz, 20 Hz, 15 Hz, 10 Hz, 5 Hz or 1 Hz. In various embodiments, the stimulation can be set to be delivered at frequencies greater than, and/or less than, one or more of 20 Hz, 30 Hz, 40 Hz, 50 Hz, 60 Hz, 70 Hz, 80 Hz, 90 Hz, 100 Hz, 120 Hz, 125 Hz, 150 Hz, up to 300 Hz. In some embodiments, where a higher frequency may be desired or required for treatment (such as tinnitus), the upper bound of the frequency may be 10,000 Hz (10 kHz). Those of skill in the art will recognize that one or more of the above frequencies can be used as a border of a range of frequencies.

In various embodiments, the stimulation is delivered at a specific duty cycle or range of duty cycles. The stimulation can be set to be delivered at a duty cycle in the range greater than and/or less than one or more of 5%, 10%, 15%, 20%, 25%, 30%, 35%, 40%, 45%, 50%, 55%, 60%, 65%, 70%, 75%, 80%, 85%, 90%, 95%, or 100%. In some embodiments, to ensure preservation of the nerve, a duty cycle of 10% to 50% may be preferable. In some embodiments, duty cycles up to 100% may be useful in particular circumstances. Those of skill in the art will recognized that one or more of the above percentages can be used as a border of a range of duty cycles.

In addition to the direct application of an electrical signal of the desired characteristics (e.g., pulse width and shape, repetition frequency, amplitude), it will be apparent to one skilled in the art that the presence of such a signal in the target tissue (i.e., in the trigeminal nerve) can be effected through the use of interferential stimulation. In interferential stimulation, two (or more) signals are applied to the tissue of the body, and these signals are designed to differ from each other in such a way that when they combine ("heterodyne" or "interfere") within the tissue, they produce the desired signal (interference signal). This approach to creating a desired signal within nerve tissue may be advantageous in some clinical circumstances because the impedance of skin and adjacent tissue depends upon frequency, and this approach may allow for application of lower amounts of energy of the tissue to accomplish a clinically-effective level of nerve stimulation.

As discussed in more detail below with respect to FIGS. 14A-14B, when nerves are stimulated with a constant signal, at times they may accommodate to the presence of that stimulation and their response to the stimulation may decline over time. To avoid this issue of accommodation, it may be desirable in some circumstances to vary the specific details of the stimulus within ranges, though such means as sweeping the frequency of stimulation within a range of frequencies (e.g., rather than stimulate only at 120 Hz, by a specific range or frequencies over a programmable, pre-determined or random amount, for example a protocol as follows: 20 Hz for 10-60 minutes, 30 Hz for 10-60 minutes, 60 Hz for 10-60 minutes, 120 Hz for 10-60 minutes, 240 Hz for 10-60 minutes) or hopping from one discrete frequency of stimulation to another from time to time, or varying the width a stimulus pulse either continuously (swept within a range) or discretely (selected from a set of discrete pulse widths). As will be apparent to one skilled in the art, the varying may take on a variety of patterns, such as a triangular or trapezoidal ramp or a sinusoidal or similar modulation pattern. Also, varying the duty cycle or on-off times, for example ranging the duty cycle from 10% to 50% over 1-24 hours, 50% to 10% over 1-24 hours, than 50% to 100%, or other intervals and time periods so as to prevent or respond to accommodation of the nerve or its related target brainstem, brain structures, and associated brain regions.

In some embodiments, an external device may be used to identify the location of the branch or branches of the trigeminal nerve that will be targeted in an individual patient for stimulation by the implanted electrode assembly disclosed herein. The external device may be used for mapping and targeting the desired branch or branches of the trigeminal nerve and for identifying the individual stimulation parameters that are optimal for efficacy and safety. In one embodiment, the device may include a plurality of external (transcutaneous) TNS electrodes. The practitioner approximates the location of the target branch and affixes the electrodes to the patient's skin above the target location. Stimulation may be applied and the actual location or preferred (optimal) stimulation location of the target branch or branches may be determined. Stimulation parameters may also be established. Once the location and/or stimulation parameters have been established via the external device, that data may be used to help guide the placement of the implanted electrodes for an individual patient and to establish the customized stimulation parameters for that patient.

In addition, the use of external electrodes for stimulation of the trigeminal nerve may identify individuals who are likely to derive therapeutic benefit from this minimally invasive system in addition to the optimal specific locations and parameters of stimulation based on person-to-person variability. Various neurodiagnostic, imaging, or cutaneous nerve mapping methods may be able to delineate differences in individual anatomy to optimize stimulation for efficacy and/or safety. Furthermore, the use of this minimally invasive system may allow screening and identification of those individuals who are likely to derive benefit from implantable systems. This can be conceptualized as linking the two approaches as stage I (external TNS of the trigeminal nerve), and stage II (implanted TNS of the superficial trigeminal nerve), such that stage I can screen for stage II. By monitoring a patient for evidence of useful therapeutic effect, such as by reduction in the severity of symptoms or reductions in heart rate, the results of treatment at one stage may be used to judge the likely effect of treatment with a more invasive treatment from a higher stage.

A method of evaluating the use of deep brain stimulation for treatment of fatigue or other medical disorder in a patient is disclosed herein. The method may include applying a transcutaneous system for stimulation of the trigeminal nerve to the patient and monitoring the patient for at least one of evidence of a useful therapeutic response or evidence of tolerability of TNS treatment thereby generating external measurement criteria, providing a subcutaneous or implantable electrode assembly or system as disclosed herein, implanting the subcutaneous electrode assembly or system as disclosed herein in the patient for treatment of fatigue or other medical disorder, monitoring the patient for at least one of a useful therapeutic response or tolerability of the implanted device, thereby generating extracranial measurement criteria, and analyzing the external measurement criteria and extracranial measurement criteria to determine whether the patient will benefit from deep brain stimulation.

Personalized and Varying Stimulation Parameters

In some embodiments, electrodes are placed in proximity to the trigeminal nerve branches (e.g., in the forehead), either implanted subcutaneously or placed percutaneously, and gentle electrical signals are used to stimulate the nerve, typically for 8 hours (while sleeping), using stimulation parameters such as a pulse width of 250 microsec, repetition rate of 120 Hz, duty cycle of 30 s on then 30 s off, and current of up to 25 mA. The electrical signals have been shown to lead to selective activation or inhibition of a set of brain structures, such as the locus coeruleus and the anterior cingulate.

Data indicates that stimulation at other parameters may have clinical effects as well, such as a frequency in the range of 1 to 10 Hz, a cycle of 2 seconds on and 90 seconds off, and pulse widths between 100 to 500 microseconds. In one embodiment, the system may deliver stimulation at one set of parameters (e.g., 120 Hz, 250 microsec) for a first period of time (e.g., several minutes) followed by a different set of parameters (such as 60 Hz, 200 microsec) for a second period of time, then other additional parameter sets (e.g. 2 Hz, 250 microsec) for a third period of time before cycling back to the first set.

Figure 8:
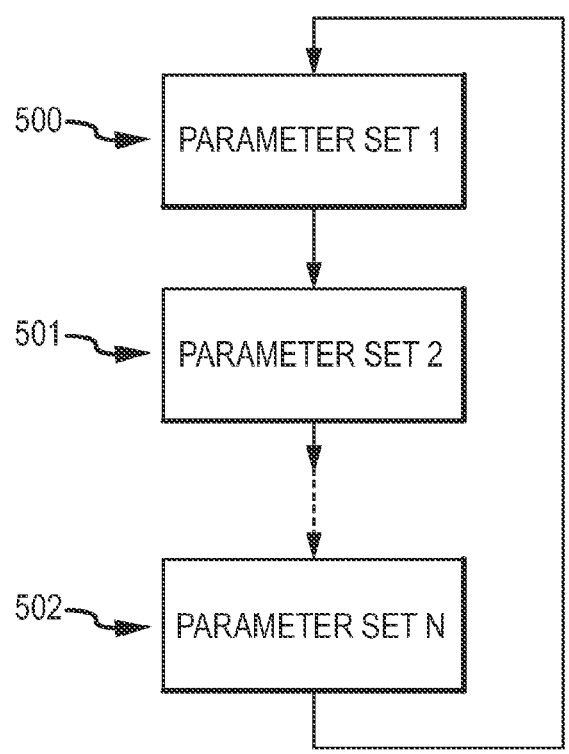
FIG. 8 depicts one embodiment of the sequential employment of N sets of stimulation parameters in accordance with aspects of the present disclosure.

FIG. 8 illustrates the sequential employment of N sets of parameters, with Parameter Set 1 500, Parameter Set 2 501, on through the final, Nth set 502 Parameter Set N. In one embodiment, the first parameter set 500 (Parameter Set 1) is employed by the stimulation generator for the duration specified in the parameter set. Once those stimuli have been produced, a second parameter set 501 (Parameter Set 2) is employed, and this sequential utilization of different parameter sets continues until the final (Nth) parameter set 502 (Parameter Set N) is employed, after which the sequence may begin again. This cycling through the N different parameter sets may occur repeatedly during the treatment administration.

In some embodiments, a plurality of stimulation parameters may be used to improve the clinical treatment effects. In such a system, several sets of parameters are utilized and the system may automatically vary the stimulation among the sets of parameters. This plurality of sets is intended to avoid any adaptation of the patient's nervous system to repeated exposure to the same unvarying stimulation pattern. In some embodiments, the stimulation pattern is selected to prevent or minimize current penetration into the brain.

In some embodiments, a system and method in which measurement of a biological feature (e.g., activity in a brain region) is used to detect an acute biological change which may be used to select a personalized set of parameters (such as repetition frequency, pulse width, or duty cycle) which are predicted to produce an intended clinical effect (or the absence of that effect for use as a sham (placebo) control condition).

Use of imaging or other biological measures to personalize the stimulation parameters to be used in trigeminal nerve stimulation may improve the clinical treatment effects. In some embodiments, instead of delivering the stimulation at a set or sets of parameters selected based on prior studies of groups of individuals with the same clinical condition (e.g., epilepsy or depression), the treating physician may monitor the individual patient's biological response to stimulation, such as with a PET neuroimaging scan (see description related to FIGS. 2 and 3 above), an EEG-derived value of current density in the brain, a fMRI scan, measures of heart activity or blood pressure, or other such measure, to select personalized parameters that produce an acute change in a biological measure which is linked to and may be predictive of later clinical outcomes. Additionally, parameters may be selected for use in a clinical research study in order to have a set of parameters which is unlikely to produce the desired clinical effect (i.e., for use as a sham (placebo) control condition). Additionally, this approach may be used to determine if there is penetration of current into the brain tissue directly from the stimulating electrodes.

Figure 9:
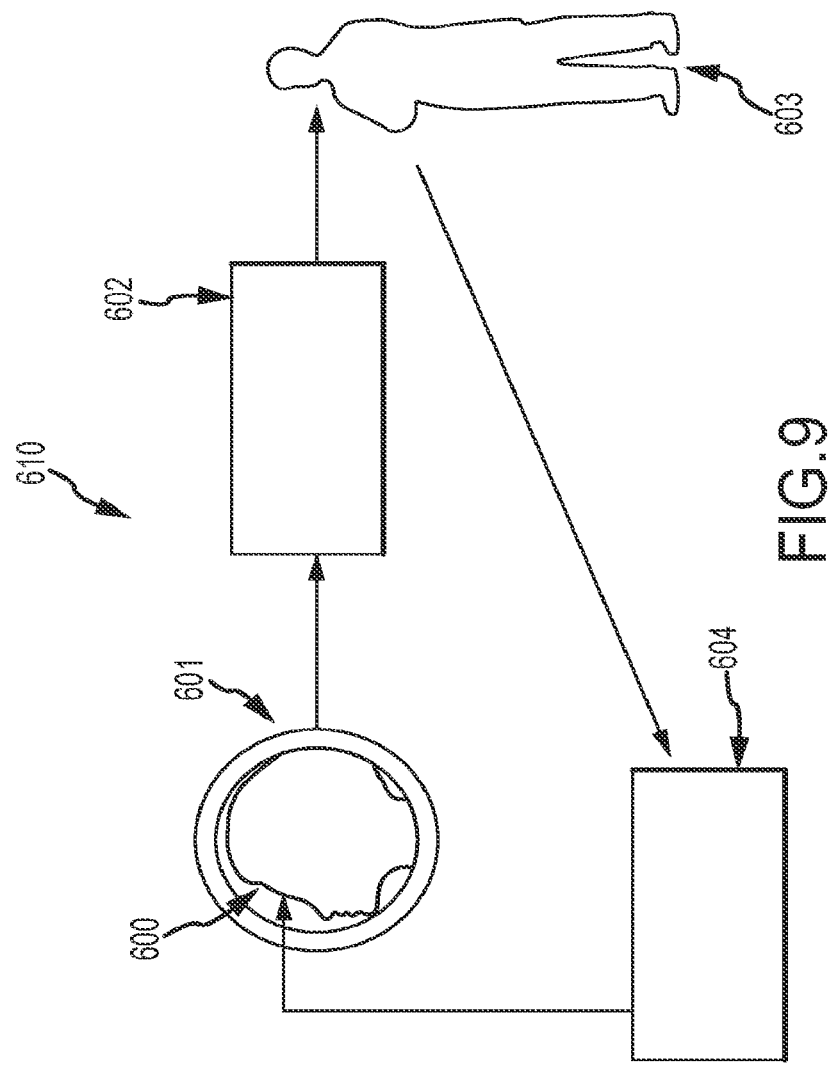
FIG. 9 depicts one embodiment of a system for determining patient specific stimulation parameters according to aspects of the present disclosure.

FIG. 9 depicts a system 610 for determining patient specific stimulation parameters. In one embodiment, the system 610 includes a biological sensing device 601, a measurement or measuring device 602 and a stimulation generator 604. The biological sensing device may be a neuroimaging device, such as a magnetic resonance imaging (MRI) scanner, a positron emission tomography (PET) scanner, or similar device; or a physiologic device, such as an electroencephalograph (EEG), an electrocardiograph (ECG or EKG), a blood pressure sensory, pulse oximeter, or other similar device. The data from the sensing device is provided to a measurement or measuring device 602 such as an imaging workstation, a computer to perform quantitative analysis of EEG signals, a graphical display of electrocardiographic data, or similar system. The information from the measurements is interpreted by the prescribing physician 603 or other clinician, and is used to make adjustments to the stimulation parameters of the generator 604 to achieve a personalized setting which may lead to a desired clinical effect. As will be apparent to one skilled in the art, aspects of the adjustments may be made through an automated device in lieu of the person 603.

In use, a patient 600 is placed in proximity to a biological sensing device 601, which is coupled, either directly or indirectly to a measurement or measuring device 602. Output from the measuring device 602 is observed by the prescribing physician or other clinician 603 and adjustments may be made to the stimulation parameters as disclosed elsewhere herein that are supplied by the stimulation generator 604 to the trigeminal nerve of patient 600.

EXAMPLES

The following examples are presented to set forth more clearly the subject matter of this disclosure without imposing any limits on the scope thereof and to illustrate the clinical benefits of trigeminal nerve stimulation for the treatment of medical disorders, including but not limited to, neuropsychiatric disorders, cardiac related disorders and fatigue or other medical disorders. In the first example, patients with major depressive disorder were treated by TNS with external cutaneous electrodes. In the second example, a patient was treated using cutaneous electrodes for bilateral supraorbital stimulation. In the third example, patients were treated using cutaneous electrodes for bilateral supraorbital and/or infraorbital stimulation and the group average data is presented. In the fourth example, patients were treated using cutaneous electrodes for bilateral supraorbital stimulation. In the fifth example, a sample protocol for mitigating potential accommodation is presented.

Example 1

Figures 10A, 10B:
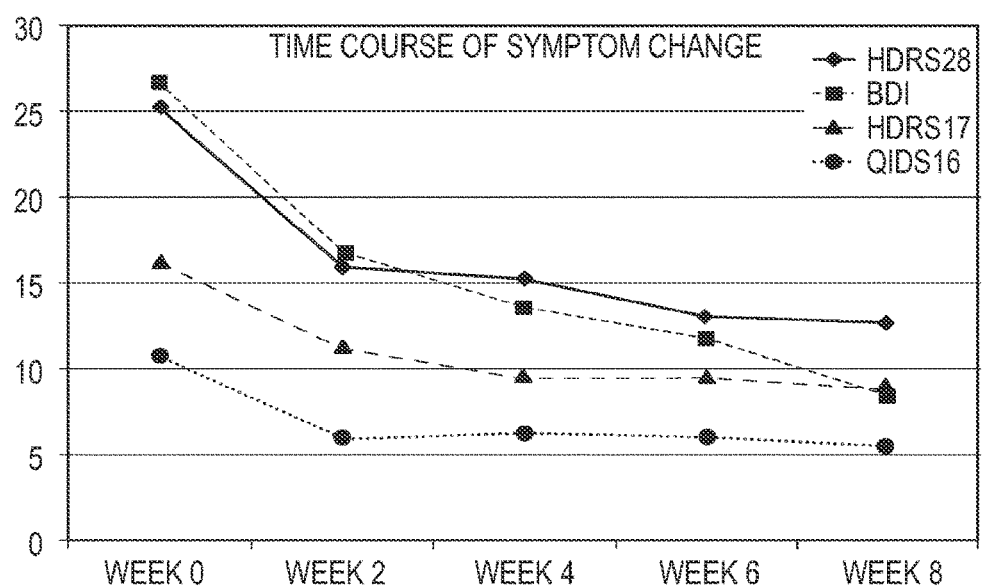
FIG. 10A is a table showing an average of the results of four assessment tests pretreatment and post treatment of a treatment study for psychiatric disorders using aspects of the present disclosure.
FIG. 10B is a bar graph of the data shown in FIG. 10A.
Figure 10C:
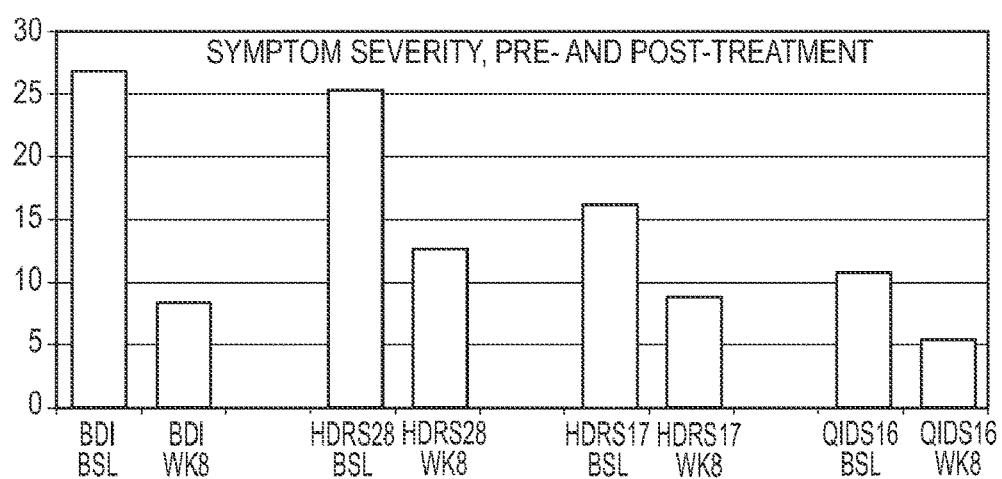
FIG. 10C is a graph illustrating the change over time of the data shown in FIG. 10A.

FIGS. 10A-10C illustrate the results from a pilot study of external trigeminal nerve stimulation for the treatment of depression. Subjects with major depression who met inclusion and exclusion criteria were followed for 8-weeks in an open label (unblinded) study conducted at UCLA.

Inclusion Criteria were: Age 18-65 years old who met DSM-IV criteria for an acute, recurrent episode of Major Depressive Disorder (MDD) and were in a major depressive episode (MDE) of moderate severity. Other inclusion criteria were: the current MDE must be ≥4 months in duration, no response to at least one antidepressant over at least six weeks during the current MDE, and concomitant use of at least one antidepressant. All had prominent residual symptoms, with mean Hamilton Depression Rating Scale (HDRS-28) scores at study entry of 25.4 (3.9 s.d.), range 19 to 29. Subjects placed stimulating electrodes over the supraorbital branches of the trigeminal nerve for at least 8 hours per day (primarily while asleep), with current adjusted to maintain comfortable levels. Five subjects completed the trial. Primary outcome was change in HDRS at 8 weeks.

Exclusion criteria were: current pregnancy; meeting DSM-IV criteria for atypical or psychotic or bipolar depression; a history of schizophrenia, schizoaffective disorder, or other non-mood disorder psychosis; a current secondary DSM-IV diagnosis (or signs) of delirium, dementia, amnestic disorder or other cognitive disorder; clinically significant current suicidal intent; significant cardiac, medical or progressive neurological or medical illness; facial pain or trigeminal neuralgia; a VNS or other implantable electrical device such as a pacemaker; current use of a TENS or VNS unit, or history of non-compliance.

All subjects received unblinded TNS augmentation (adjunctive) treatment for at least 8-hours each day. Assessments were made at study intake, and at weeks 2, 4, 6, and 8 in the acute treatment phase. Subjects who wished to continue the treatment were allowed to participate in an optional 6-month long-term extension phase with monthly monitoring visits.

Subjects underwent stimulation using an electrical stimulator, such as for example the EMS Model 7500 commercially available from TENS Products, Inc. (www.tensproducts.com) operated at a frequency of 120 Hertz, a current less than 20 mA, a pulse duration of 250 µec, and a duty cycle at 30 seconds on and 30 seconds off, for a minimum of 8 hours per day.

Prior to initiating treatment and at subsequent follow-up assessment visits, the symptom severity of each subject was quantified using the Hamilton Depression Rating Scale (HDRS, scored using both 17- and 28-item versions), the Beck Depression Inventory (BDI), and the Quick Inventory of Depressive Symptomatology (QIDS), with the group average values on each of these scales being tabulated in the table shown in FIG. 6A. All three are assessment instruments designed to measure the severity of depression. The HDRS is a well-established rating scale instrument which is filled out by a clinician after interviewing and observing the individual subject in order to measure the severity of depression; in this study, ratings on all 28 items (questions) were made, and the scale was scored according to standard methods using all items ($HDRS_{28}$) and the standard subset of 17 items ($HDRS_{17}$). The BDI is a 21-question multiple choice self-report survey that is used to measure the severity of depression. The $QIDS-C_{16}$ is a 16-question clinician-rated survey that is used to measure the severity of depression. Each of these scales affords different strengths and limitations in assessing a patient's symptom severity (e.g. BDI emphasizes cognitive symptoms of depression, while the HDRS weights neurovegetative symptoms prominently), and all are commonly used in clinical trials in major depression; the use of multiple scales allowed a more comprehensive assessment of the effects of trigeminal nerve stimulation than any single scale in this initial study of this treatment for major depression.

As shown in FIG. 10A, and graphically illustrated in FIGS. 10B and 10C, decreases in $HDRS_{28}$ were significant, from 25.4 (3.9 s.d.) at entry to 13.6 (6.3 s.d.) at week 8 (2-tail t-test p<0.01, Cohen's d 2.4). Responses on the BDI similarly declined, from 26.8 (8.1) to 10.6 (4.9) (p<0.01, d 2.3). Decreases on the 16-item clinician-rated QIDS were also significant, decreasing from 10.8 (3.4) to 5.5 (4.4) (p<0.05, d 1.3). Thus, significant decreases in symptom severity were achieved in the 8 weeks of acute TNS treatment. Furthermore, changes in symptoms occurred across all symptom areas, such as depressed mood, anxiety, sleep, and energy. These findings support the use of TNS treatment which may also have use as an adjunct to pharmacotherapy when medications have failed to produce remission of symptoms.

Example 2

FIG. 11 summarizes current, charge, current density and charge density recorded in a subject during exposure to cutaneous stimulation of the supraorbital nerve. FIG. 7 illustrates representative parameters for bilateral supraorbital stimulation recorded in a subject using an EMS 7500 stimulator, 120 HZ, 150-250 usec, Tyco superior silver electrodes 1.25", placed one inch from the midline above the eyebrows. Data recorded with Fluke Oscilloscope, 50 mV/div, resistor=10.1Ω. In general, these findings show that, as the pulse width increased, the maximum tolerable current decreased.

Cutaneous electrical stimulation of the supraorbital branch of the trigeminal nerve with round 1.25-inch TENS patch electrodes results in current densities and charge density/phase that are well within the limits of safety. In general, the maximum current comfortably tolerated by TNS patients studied previously is approximately 25 mA, and patients typically are stimulated at an amplitude setting well below 25 mA (6-10 mA).

The 1.25-inch TENS electrodes are circular electrodes with a radius of 1.59 cm. The surface area can be calculated as $A=\Pi r^2=[\Pi]\times[1.59\ cm]^2=7.92\ cm^2$. Using these electrodes, typical stimulation current ranges from 6-10 mA at pulse durations of 150-250 usec.

Current Density: In a typical subject, stimulation currents of 6-10 mA result in current densities ranging from 0.76 to 1.3 $mA/cm^2$. McCreery et al have established a maximum safe current density of 25 mA/cm at the stimulating electrode for transcranial electrical stimulation. Assuming even higher currents of up to 25 mA with electrodes of surface area 7.92 $cm^2$, current densities may range to a maximum of 3.16 $mA/cm^2$. From 0.76 $mA/cm^2$ to 3.16 $mA/cm^2$, TNS delivers a current density 8-33 times less than the maximum safe allowable current density. Charge Density (Charge density/phase): Yuen et al have identified a safe limit for charge density/phase delivered at the cerebral cortex of 40 $uC/cm^2$. [Yuen et al 1981] and more recently McCreery et al. (McCreery et al 1990) have identified 10 $uC/cm^2$ as the safe limit. Assuming 10 mA at 250 usec, the charge density/phase is $[0.010\ A]\times[250\ usec]/7.92=0.32\ uC/cm^2$ at the stimulating electrode. Assuming even higher levels of stimulation, 25 mA at 250 usec, the maximum charge density per phase is 0.79 $uC/cm^2$. At these levels, the charge density is generally 12 to 120 fold less at the stimulating electrode than the maximum allowed at the cerebral cortex. Since the cortex is a minimum of 10-13 mm from the stimulating electrodes, and given the interposed layers of skin, fat, bone, dura, and CSF, the actual charge densities will be significantly lower. This is of importance in avoiding the undesired passage of current directly through brain tissue as a bulk conductor.

As shown in FIG. 11, stimulation intensity responses in a subject with electrodes of surface area 7.92 cm2, at pulse durations between 150-250 usec, results in current densities at the scalp well below currently recommended current densities for transcranial stimulation, which are 25 $mA/cm^2$, and charge densities at the scalp significantly lower than safe charge densities at the cerebral cortex (0.15-0.18 $uC/cm^2$).

Example 3

Figure 12:
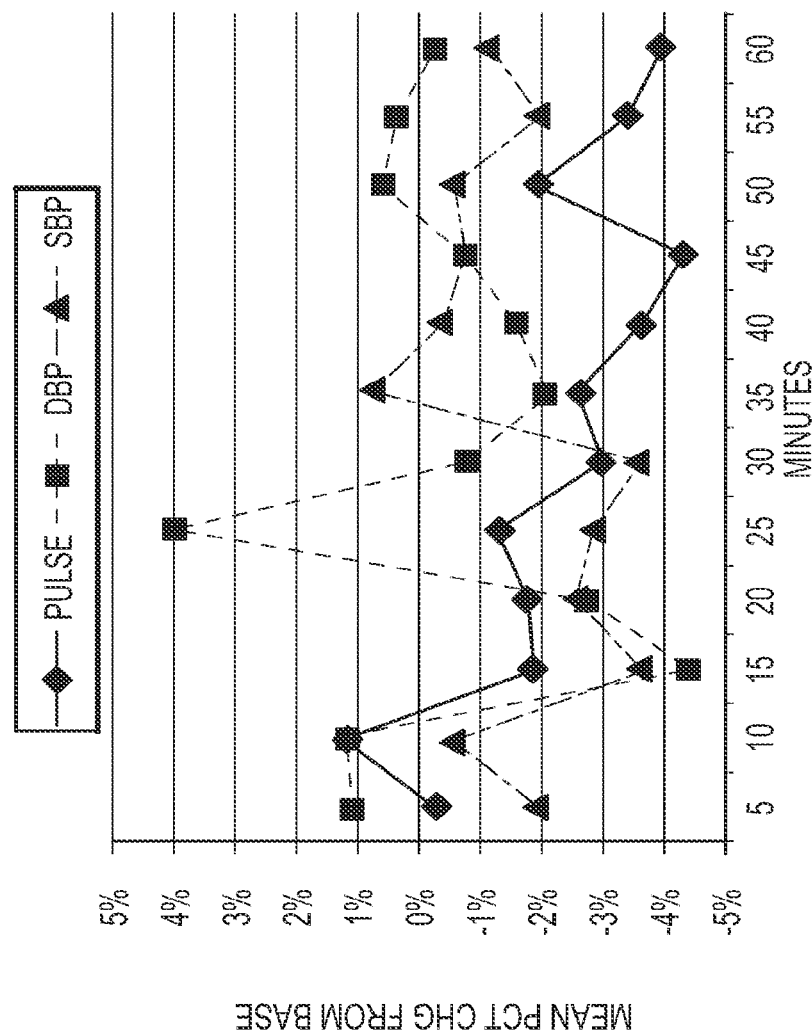
FIG. 12 illustrates patient response to cutaneous stimulation of the supraorbital and infraorbital nerve according to one aspect of the present disclosure.

FIG. 12 illustrates the response to TNS at 120 Hz, 10-30 seconds on/30 seconds off, infraorbital or supraorbital stimulation in patients with epilepsy. Note the measured and mild reductions in heart rate, consistent with activation of the Trigeminal Cardiac Reflex. This reflects the effects of vagus nerve stimulation from Trigeminal Nerve Stimulation. Mild reductions in heart rate occur without significant changes in systolic or diastolic blood pressure. The reduction in heart rate is protective in the setting of myocardial infarction, heart failure, tachyarrhythmia's, and conditions associated with the risk of sudden death.

Example 4

Figure 13:
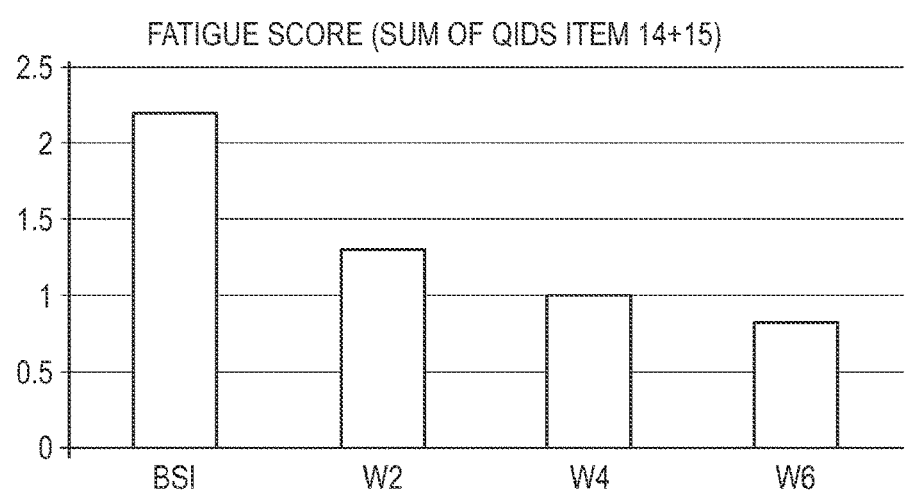
FIG. 13 illustrates patient response to cutaneous stimulation of the trigeminal nerve according to one aspect of the present disclosure.

FIG. 13 illustrates the changes in fatigue scores with trigeminal nerve stimulation. Data was collected from 10 adults who received TNS nightly. The level of fatigue was assessed using the sum of items 14 ("energy level") and 15 ("feeling slowed down") on the Quick Inventory of Depressive Symptomology (ids-qids.org). Mean scores declined from a level of 2.2 (s.d.1.3) at pretreatment baseline (bsl), to 0.8 (s.d. 0.9) at six weeks of treatment (w6), a statistically significant improvement (2-tailed paired t-test p=0.001).

Example 5

Figure 14B:
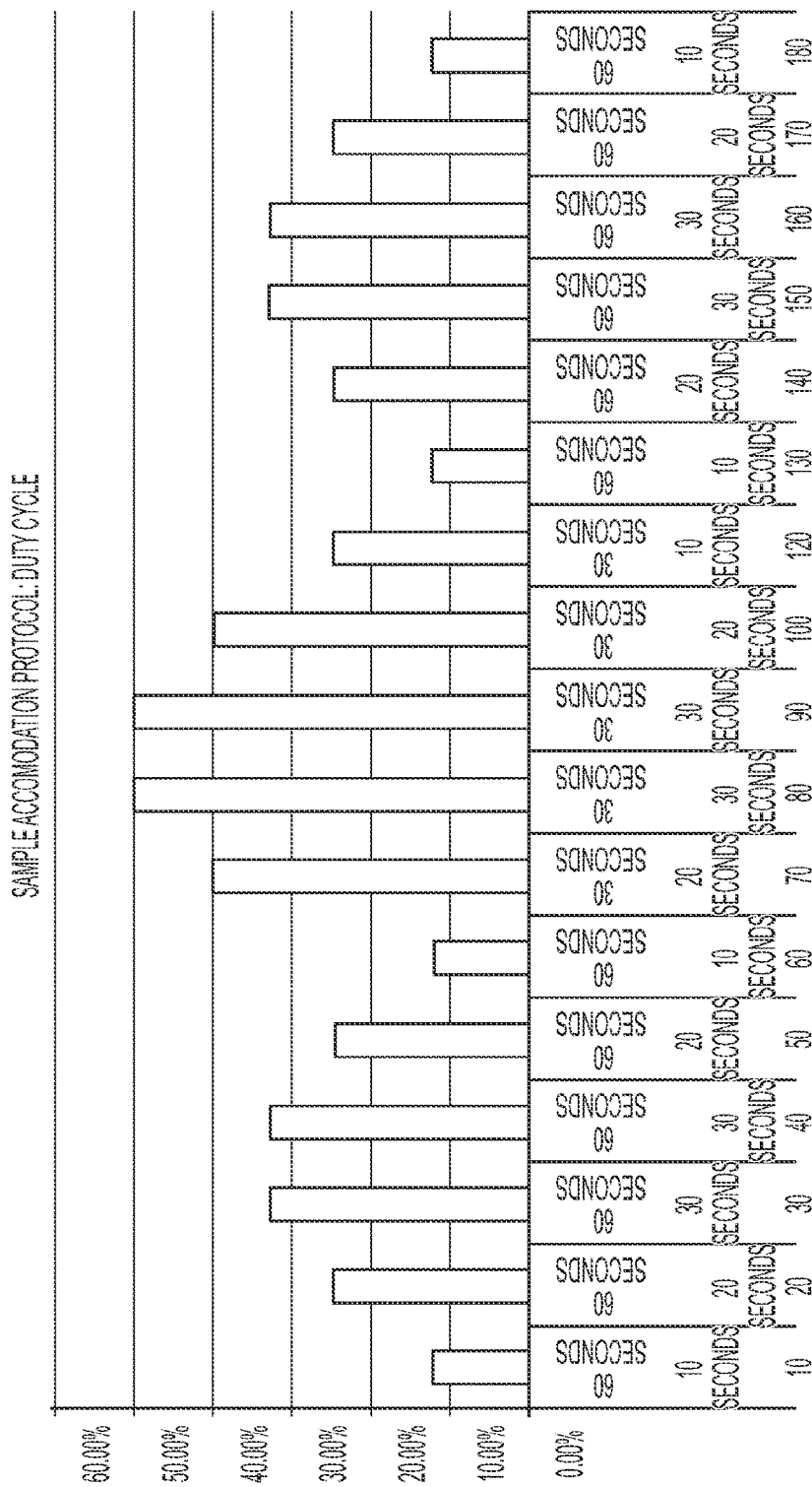

FIGS. 14A-14B illustrate a sample protocol for mitigating the potential effects of accommodation.

All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification and examples provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the spirit or scope of this invention. Other embodiments are therefore contemplated. For example, stimulation of the target nerve may be accomplished by cutaneous application of energy in many forms, such as magnetic or ultrasonic. It is intended that all matter contained in the above description and shown in the accompanying drawings shall be interpreted as illustrative only of particular embodiments and not limiting. Changes in detail or structure may be made without departing from the basic elements of the invention as defined in the following claims.

The invention claimed is:

1. A method for treatment of a medical disorder by trigeminal nerve stimulation, comprising:

implanting an implantable electrode assembly including a first contact and a second contact above a pericranium and below an epidermis at a patient's forehead such that the first contact is in contact with a supraorbital nerve and the second contact is in contact with an adjacent supratrochlear nerve; and applying electrical signals to the electrode assembly to stimulate the supraorbital nerve and the adjacent supratrochlear nerve at the patient's forehead to modulate a body system of the patient to treat the medical disorder selected from the group consisting of attention deficit disorder (ADD) and attention deficit hyperactivity disorder (ADHD).

2. The method of claim 1, wherein the implanting comprises implanting the implantable electrode assembly including a third contact.

3. The method of claim 1, wherein the applying of the electrical signals comprises applying electrical signals at a frequency between 20 and 300 Hertz, at a current of 0.1 to 3 milliamperes (mA), and at a pulse duration of less than or equal to 500 microseconds.

4. The method of claim 1, wherein the applying of the electrical signals comprises applying electrical signals at a frequency between 20 and 300 Hertz, at a pulse duration between 50 and 500 microseconds, at an output current density of not greater than 10 $mA/cm^2$, and a charge density of not greater than 10 $microCoulomb/cm^2$ at the patient's cerebral cortex.

5. The method of claim 1, wherein the applying of the electrical signals comprises applying electrical signals at an output current density of not greater than 10 $mA/cm^2$.

6. The method of claim 1, wherein the applying of the electrical signals comprises applying electrical signals at an output current density of between 2.5 and 5 $mA/cm^2$.

7. The method of claim 1, wherein the applying of the electrical signals comprises applying electrical signals at an output current density of not greater than 7 $mA/cm^2$.

8. The method of claim 1, wherein the implanting comprises implanting the implantable electrode assembly including a third contact and a fourth contact such that the third contact is in contact with a remaining supraorbital nerve and the fourth contact is in contact with an adjacent remaining supratrochlear nerve, wherein the applying of the electrical signals to the electrode assembly is further to stimulate the remaining supraorbital nerve and the adjacent remaining supratrochlear nerve at the patient's forehead to modulate the body system to treat the medical disorder.

* * * * *